US006429360B1

(12) United States Patent
Estruch et al.

(10) Patent No.: US 6,429,360 B1
(45) Date of Patent: *Aug. 6, 2002

(54) PLANT PEST CONTROL

(75) Inventors: Juan Jose Estruch, Durham; Gregory Wayne Warren, Cary; Nalini Manoj Desai, Chapel Hill, all of NC (US); Michael Gene Koziel, Clive, IA (US); Gordon James Nye, Raleigh, NC (US)

(73) Assignee: Syngenta Investment Corporation, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/904,226

(22) Filed: Jul. 12, 2001

Related U.S. Application Data

(63) Continuation of application No. 09/402,036, filed as application No. PCT/EP98/01952 on Apr. 2, 1998, now Pat. No. 6,291,156, which is a continuation-in-part of application No. 08/838,219, filed on Apr. 3, 1997, now Pat. No. 5,877,012, and a continuation-in-part of application No. 08/832,263, filed on Apr. 3, 1997, now abandoned, and a continuation-in-part of application No. 08/832,265, filed on Apr. 3, 1997, now abandoned, said application No. 08/838,219, is a continuation-in-part of application No. 08/463,483, filed on Jun. 5, 1995, now Pat. No. 5,849,870, which is a continuation-in-part of application No. 08/314,594, filed on Sep. 28, 1994, now abandoned, which is a continuation-in-part of application No. 08/218,018, filed on Mar. 28, 1994, now abandoned, which is a continuation-in-part of application No. 08/037,057, filed on Mar. 25, 1993, now abandoned.

(51) Int. Cl.[7] .................. A01H 5/00; A61K 38/00
(52) U.S. Cl. ............. 800/302; 435/410; 435/252.3; 435/252.31; 435/252.33; 514/12; 530/350; 536/23.71
(58) Field of Search .............. 800/302; 514/12; 435/252.3, 252.31, 252.33, 410; 536/23.71; 530/350

(56) References Cited

U.S. PATENT DOCUMENTS

| 3,632,747 A | 1/1972 | Satohiro et al. ............... 424/93 |
| 3,651,215 A | 3/1972 | Satohiro et al. ............... 424/93 |
| 4,996,155 A | 2/1991 | Sick et al. ................ 435/252.3 |
| 5,262,323 A | 11/1993 | Baird et al. ............... 435/252.5 |

FOREIGN PATENT DOCUMENTS

| EP | 0498537 A2 | 1/1992 |
| EP | 0501650 A2 | 2/1992 |
| WO | WO88/08880 | 11/1988 |
| WO | WO90/13651 | 11/1990 |
| WO | WO91/16432 | 10/1991 |
| WO | WO91/16434 | 10/1991 |
| WO | 94/03131 | 7/1994 |
| WO | WO 94/21795 | 9/1994 |
| WO | WO 96/00783 | 1/1996 |
| WO | WO 96/09398 | 3/1996 |
| WO | WO 96/10083 | 7/1996 |
| WO | WO 97/26339 | 7/1997 |
| WO | WO 98/00546 | 1/1998 |
| WO | WO 98/18932 | 5/1998 |

OTHER PUBLICATIONS

Arellano, A., et al., Evidence of a New *Bacillus thuringiensis* Toxin Active Against the Australian Sheep Blowfly *Lucilla cuprina Proceedings and Abstracts of the 5th International Colloquium on Invertebrate Pathology and Microbial Control*, Adelaide, Austrailia, 20–24 (Aug., 1990) pp. 291.

Beecher, D. J., et al., A Novel Bicomponent Hemolysin from *Bacillus cereus, Inspection and Immunity*, 58(7): (1990), pp. 2220–2227.

Bernier et al., *Bacillus thuringiensis* strains a20 and a29 and insecticidal compounds therefrom, and compositions containing these compounds Abstract No. 227249, *New Zealand Patent Office Journal*, 80(6): (1998) pp. 798.

Chambers et al., Isolation and Characterization of a Novel Insecticidal Crystal Protein Gene from *Bacillus thuringiensis* subsp. *aizawai Journal of Bacteriology*, (Jul. 1991), pp. 3966–3976.

Estruch, J., et al, VipA, a novel *Bacillus thuringiensis* vegetative insecticidal protein with a wide spectrum of activities against lepidopteran insects *Proceedings of the National Academy of Sciences*, 93 (1996) pp. 5389–5394.

Estruch, J., et al. Transgenic plants: an emerging approach to pest control *Nature Biotechnology* 15, (1997) pp. 137–141.

European International Search Report PCT/EP95/03826 dated May 3, 1996.

Faust, R.M., et al., "Bacteria and Their Toxins as Insecticides", in E. Kurstak, Ed., Marcel Dekker., *Microbial and Viral Pesticides*, (New York, 1982), pp. 84–89, 108–120.

Faust, R.M., "Bacterial Diseases" in G. Cantwell, ed., Marcel Dekker, *Insect Diseases*, (New York 1974), pp. 90–102.

Gilmore, Michael S., et al., A *Bacillus cereus* Cytolytic Determinant, Cereolysin AB, Which Comprises the Phospholipase C and Sphingomyelinase Genes: Nucleotide Sequence and Genetic Linkage *Journal of Bacteriology*, 171(2) (1989) pp. 744–753.

(List continued on next page.)

*Primary Examiner*—Nashaat T. Nashed
(74) *Attorney, Agent, or Firm*—Gregory Warren; J. Timothy Meigs; Gary Pace

(57) ABSTRACT

The genes encoding a novel class of insecticidal proteins have been isolated and characterized from a strain of *Bacillus thuringiensis*. Both the nucleic and amino acid sequences for the proteins are disclosed. The nucleic acid molecules are utilized in the transformation of host microorganisms and production of transgenic plants which are resistant to insects. Also, the gene encoding for the insect's receptor of the insecticidal protein has been isolated and characterized. Novel processes and methods for controlling plants pests are provided.

8 Claims, 1 Drawing Sheet

OTHER PUBLICATIONS

Gleave, et al., Screening by Poymerase Chain Reaction of *Bacillus thuringiensis* Serotypes for the Presence of cryV–like Insecticidal Protein Genes and Characterization of a cryV Gene Cloned from *B. thuringiensis* subsp. *Kurstaki Applied and Environmental Microbiology* 59(5) (1993) pp. 1683–1687.

Heimpel, A.M., The pH in the Gut and Blood of the Larch Sawfly, *Pristiphora erichsonii* (HTG.), and Other Insects with Reference to the Pathogenicity of *Bacillus cereus* FR. and FR *Canadanian Journal of Zoology,* 33 (1955) pp. 99–106.

Heimpel, A.M., Investigations of the Mode of Action of Strains of *Bacillus cereus* FR. and FR. Pathogenic for the Larch Sawfly, *Pristiphora erichsonii* (HTG.) *Canadian Journal of Zoology,* 33, (1995) pp. 311–326.

Hofte, H., et al., Insecticidal Crystal Proteins of *Bacillus thuringiensis Microbiological Reviews,* 53(2) (1989) pp. 242–255.

Jellis et al., *Bacillus thuringiensis* δ–endotoxin variants and Insecticidal compositions, Abstract No. 228108, *New Zealand Patent Office Journal,* 81(3) (1992) pp. 359.

Kostichka, et al. Cloning of a cryV–type Isecticidal Protein Gene from *Bacillus thuringiensis:* the cry–V encoded Protein is Expressed Early in Stationary Phase *Journal of Bacteriology* 178 (7) (1996) pp. 2141–2144.

Koziel, M.G., et al., Field Performance of Elite Tansgenic Maize Plants Expressing an Insecticidal Protein Derived from *Bacillus thuringiensis Bio/Technology,* 11 (1993) pp. 194–200.

Krieg, A., Thuricin, a Bacteriocin Produced by *Bacillus thuringiensis Journal of Invertebrate Pathology* (1970) pp. 15:291.

Krieg, A., Concerning Alpha–exotoxin Produced by Vegetative Cells of *Bacillus thuringiensis* and *Bacillus cereus Journal of Invertebrate Pathology* 17 (1971) pp. 134–135.

Kushner, D.J., et al., Lecithinase Production by Strains of *Bacillus cereus* FR. and FR. Pathogenic for the Larch Sawfly, *Pristiphora erichsonii* (HTG.) *Canadian Journal of Microbiology* 3 (1957) pp. 547–551.

Luthy, P., et al., *Bacillus thuringiensis* as a Bacterial Insecticide: Basic Consideration and Application, In E. Kurstak, Ed., Marcel Dekker *Microbial and Viral Pesticides,* (New York, 1982), pp. 37–39, 54–56.

Myers, P.S., et al., Localization of a Mosquito–Larval Toxin of *Bacillus sphaericus* 1593 *Applied and Environmental Microbiology* 39(1) (1980) pp. 1205–1211.

Porter, A.G., et al., Mosquitocidal Toxins of Bacilli and Their Genetic Manipulation for Effective Biological Control of Mosquitoes *Microbiological Reviews,* 57(4) (1993) pp. 838–861.

Schurter et al., Genetic manipulation of *B.thuringiensis* and *B.cereus* vectors and insecticidal composition Abstract No. 229191, *New Zealand Patent Office Journal,* 81(3) (1992) pp. 363.

Sekar, V., The Insecticidal Crystal Protein Gene is Expressed in Vegetative Cells of *Bacillus thuringiensis* var. *temebropmos Current Microbiology,* 17pp. 347–349 (1988).

Shlvakumar, A.G., et al., Abstract: Cloned Crystal Protein Genes Express Vegetatively in *Bacillus subtilis Plasmid,* 16(3) (1986) pp. 230.

Tayabali et al., Semiautomated Quantification of Cytotoxic Damage Induced in Cultured Insect Cells Exposed to Commercial *Bacillus thuringiensis* Biopesticides *Journal of Applied Toxicology,* 15(5) (1995) pp. 365–373.

Thanabalu, T., et al., Proteolytic Processing of the Mosquitocidal Toxin from *Bacillus sphaericus* SSII–1 *Journal of Bacteriology,* 174(15) (1992) pp. 5051–5056.

Thanabalu et al., Cytotoxicity and ADP–Ribosylating Activity of the Mosquitocidal Toxin from *Bacillus sphaericus* SSII–1: Possible Roles of the 27– and 70–Kilodalton Peptides *Journal of Bacteriology,* 175(8) (1993) pp. 2314–2320.

Vaithlingam et al., "Anti–coleopteran toxin and gene", Abstract No. 226442, *New Zealand Patent Office Journal,* 80(7) (1991), pp. 931.

Wahiaska et al., "*Bacillus thuringiensis* mutant and bacterial insecticide", Abstract No. 199725, *New Zealand Patent Office Journal,* (1982).

Walther et al., Analysis of Mosquito Larvicidal Potential Exhibited by Vegetative Cells of *Bacillus thuringiensis* subsp. *israelensis Applied and Environmental Microbiology,* 52(4) (1986) pp. 650–653.

Ward et al., *Bacillus thuringiensis* var. *israelensis* δ–Endotoxin Cloning and Expression of the Toxin in Sporogenic and Asporogenic Strains of *Bacillus subtilis Journal of Molecular Biology,* 191(1) (1986) pp. 13–22.

Yoshisue, H., et al., Effects of *Bacillus thuringiensis* var. *israelensis* 20 kDa Protein on Production of the Bti 130–kDa Crystal Protein in *Escherichia coli Bioscience, Biotechnology, and Biochemistry,* 56(9) (1992) pp. 429–1433.

Yu, C.G The *Bacillus thuringiensis* vegetative insecticidal protein Vip3A lyses midgut epithelium cells of susceptible insects. *Applied and Environmental Microbiology* 63, (1997) pp. 532–536.

Figure 1

```
1                              20
SGSPGLQEFAAASTMYSRIFFLLVIVCAVKASLFTVN
  40                           60
VYDDNPETEIASSLKGCNPQECDQRCRRLKFPGGA
      80                      100
CVNGRCKCDNFLSVKDDVSVEEPAILKDLVSLEAEQ
            120                    140
AAKSRCRNRVCDAVCRALHNTSGACVDGQCKCTN
                 160
KISAGDIVSDPAESLRTCNPIRCDEQCRRNGHEFGV
 180                        200
CFKGQCKCDYFLKEEVDEPEVTSLPKNCNPQECDQ
           220                    240
RCRRLKFPGGACVNGRCKCDNFFSAGDIVSDPAES
                260                       280
LRSCNPIRCDEQCRRNGHEFGVCFKGQCKCDYFL
                 300
NSEVDAVNEFPQAGSKRYCNLTQCNQTCANRRFD
       320                      340
SARVIHGWCKCYSKMERQDASPLNDVTEDENEVS
                 360               380
NDILRTVAEELSDVSPRACKSASCNQACRAFYFKG
                396
GWCRFGRCQCF
```

PLANT PEST CONTROL

This is a continuation of Ser. No. 09/402,036, now U.S. Pat. No. 6,291,156 which is a national stage application of PCT/EP/98/01952, filed Apr. 2, 1998, and published Oct. 8, 1998 as WO 98/44137, which is a continuation-in-part of each of the following U.S. patent applications Ser. No. 08/838,219, filed Apr. 3, 1997, now U.S. Pat. No. 5,877,012; Ser. No. 08/832,263, filed Apr. 3, 1997, abandoned; and Ser. No.08/832,265, filed Apr. 3, 1997, abandoned. Said U.S. patent application Ser. No. 08/838,219, now U.S. Pat. No. 5,877,012 is a continuation-in-part of U.S. application Ser. No. 08/463,483, filed Jun. 5, 1995 now U.S. Pat. No. 5,849,870, which is a continuation-in-part of U.S. application Ser. No. 08/314,594, filed Sep. 28, 1994, abandoned, which is a continuation-in-part of U.S. patent application Ser. No. 08/218,018, filed Mar. 23, 1994, abandoned, which is a continuation-in-part of U.S. patent application Ser. No. 08/037,057, filed Mar. 25, 1993, abandoned.

The present invention relates to a novel class of proteins for the control of plant pests. Plant pests are a major factor in the loss of the world's commercially important agricultural crops resulting both in economic hardship to farmers and nutritional deprivation for local populations in many parts of the world. Broad spectrum chemical pesticides have been used extensively to control or eradicate pests of agricultural importance. There is, however, substantial interest in developing effective alternative pesticides.

Control of various pests through the use of biological molecules has been possible in only a limited number of cases. The best known examples of biological molecules with pesticidal uses are the δ-endotoxins from *Bacillus thuringiensis* (Bt), which is a gram-positive spore forming microorganism. Varieties of Bt are known that produce more than 25 different but related δ-endotoxins. Bt strains produce δ-endotoxins during sporulation the use of which is limited because they are active against only a very few of the many insect pests.

The limited specificity of the Bt endotoxins is dependent, at least in part, on both the activation of the toxin in the insect gut (Haider, M. Z et al., 1986, Eur. J. Biochem. 156:531–540) and its ability to bind to specific receptors present on the insects midgut epithelial cells (Hofmann, C. P. et al., 1988, PNAS 85.7844–7848). Therefore, the ability to control a specific insect pest using δ-endotoxins at present depends on the ability to find an appropriate δ-endotoxin with the desired range of activity. In many cases, no such δ-endotoxin is known, and It is not certain that one even exists.

Plants also routinely become infected by fungi and bacteria, and many microbial species have evolved to utilize the different niches provided by the growing plant. In addition to infection by fungi and bacteria, many plant diseases are caused by nematodes which are soil-borne and infect roots, typically causing serious damage when the same crop species is cultivated for successive years on the same area of ground.

The severity of the destructive process of disease depends on the aggressiveness of the phytopathogen and the response of the host, and one aim of most plant breeding programs is to increase the resistance of host plants to disease. Novel gene sources and combinations developed for resistance to disease have typically only had a limited period of successful use in many crop-pathogen systems due to the rapid evolution of phytopathogens to overcome resistance genes.

It is apparent, therefore, that scientists must constantly be in search of new methods with which to protect crops against plant pests. It has been found in the present invention a novel class of proteins which can be used to control plant pests.

Programmed cell death is a process whereby developmental or environmental stimuli activate a genetic program that culminate in the death of the cell (Jacobson, M. D. et al., 1997, Cell 8B: 347–354). This genetic potential exists in most, if not all, multicellular organisms. In the case of invertebrates, programmed cell death appears to play a dual role by being an integral part of both the insect development process and a response mechanism to infections particularly of viral nature (Clem, R. J. et al., 1991, Science 254: 1388–1390). Programmed cell death appears to be executed in several different manners leading to either apoptosis, atrophy or differentiation. Apoptosis is one of the best characterized types of programmed cell death encompassing cytological changes including membrane-bound apoptotic bodies and cytoplasmic blebbing as well as molecular changes such as endonucleolysis typified by the generation of oligosomal length fragments (Vaux, D. L and Strasser, A., 1996, PNAS 93:2239–2244). Although the overall apoptotic phenomenology is rather conserved among the different organisms, It is interesting to point out that, for many insect cells, cytoplasmic vacuolization and swelling rather than condensation seem to be the cytological features associated with apoptotic processes (Bowen, I. D., et al., 1996, Micros. Res. Techniq.34:202–217). The novel class of proteins disclosed within the present invention are shown to induce programmed cell death and exert a pesticidal effect.

The present invention is drawn to VIP3A(c) proteins including homologues thereof. Also provided by the invention are domains of proteins of the VIP3 class, including the toxic domain and the stabilizing domain. A preferred embodiment of the invention is the toxic domain of the VIP3A(a) protein and homologues thereof. Another preferred embodiment are antibodies to proteins of the VIP3 class, but preferably to the VIP3A(c) protein.

The invention also provides hybrid toxins comprising a toxic domain of a protein of the VIP3 class. In a preferred embodiment, the hybrid toxin is a chimeric proteins having a toxic core domain operably linked to a heterologous stabilizing domain. In another preferred embodiment, the hybrid toxin comprises an antibody, or immunologically-active fragment thereof, which immunologically recognizes the VIP3 receptor operably linked to a toxic domain from other proteins, wherein the toxin domain is obtained from a number of cytotoxic proteins including but not limited to Bacilus toxins, including endotoxins and vegetative insecticidal proteins.

Also encompassed by the invention are plants comprising a DNA sequence which encodes a protein of the VIP3 class, but preferably a VIP3A(c) protein. Preferred embodiments include plants selected from the group consisting of maize, sorghum, wheat, sunflower, tomato, cole crops, cotton, rice, soybean, sugarbeet, sugarcane, tobacco, barley, and oilseed rape. In a particularly preferred embodiment, the plant is a maize plant.

The invention also provides microorganisms comprising a heterologous DNA sequence which encodes a protein of the VIP3 class, but preferably a VIP3A(c) protein. In a preferred embodiment, the microorganism is selected from the group consisting of bacteria, baculovirus, algae and fungi. In another preferred embodiment, the microorganism is selected from the group consisting of Bacillus, Pseudomonas, Clavibacter, and Rhizobium. Further encompassed by the invention are entomocidal compositions comprising microorganisms comprising a heterologous DNA sequence which encodes a protein of the VIP3 class, but preferably a VIP3A(c) protein.

The invention further relates to plants and microorganisms further comprising a second DNA sequence which encodes a second insecticidal protein. Particularly preferred second DNA sequences are those which encode a δ-endotoxin, those which encode another protein of the VIP3 class, or those which encode a protein of the VIP1 or VIP2 classes. In a more preferred embodiment, the δ-endotoxin is active against an insect selected from the group consisting of Lepidoptera and Coleoptera. In a more particularly preferred embodiment the δ-endotoxin is active against Ostrinia, or Diabrotica. In another particularly preferred is a second DNA sequence which encodes a δ-endotoxin protein selected from the group consisting of Cry1, Cry3, Cry5 and Cry9. In a more particularly preferred embodiment, the δ-endotoxin is selected from the group consisting of Cry1Aa, Cry1Ab, Cry1Ac, Cry1B, Cry1C, Cry1D, Cry1Ea, Cry1Fa, Cry3A, Cry9A, Cry9C and Cry9B. Most particularly preferred are Sendotoxins selected from the group consisting of Cry1Ab, Cry1Ba and Cry9C proteins.

The invention further provides a method of controlling insects by contacting the insects with an insecticidal amount of a protein of the VIP3 class, but preferably a VIP3A(c) protein, or an insecticidal amount of a chemical ligand to a receptor of the VIP3 class of proteins. In one preferred embodiment, the insects are contacted with a transgenic plant comprising a DNA sequence which expresses a protein of the VIP3 class, but preferably a VIP3A(c) protein in another preferred embodiment, the insects are contacted with a an entomocidal composition comprising a protein of the VIP3 class, but preferably a VIP3A(c) protein, or comprising a DNA sequence which expresses a protein of the VIP3 class, but preferably a VIP3A(c) protein. In another preferred embodiment, the transgenic plant comprises a DNA sequence which expresses the VIP3A(a) protein. In another preferred embodiment the insect is selected from the group consisting of Coleoptera, Diptera, Hymenoptera, Lepidoptera, Mallophaga, Homoptera, Hemiptera, Orthroptera, Thysanoptera, Dernaptera, Isoptera, Anoplura, Siphonaptera, Trichoptera, and Acari. In a particularly preferred embodiment, the insect is a Coleoptera or Lepidoptera. In another particularly preferred embodiment, the insect is selected from the group consisting of black cutworm (*Agrotis ipsilon*), fall armyworm (*Spodoptera frugiperda*), beet armyworm (*S. exigua*), yellow striped armyworm (*S. omithogalli*), southwestern corn borer (*Diatraea grandiosella*), sugarcane borer (*D. saccharalis*), corn earworm (*Helicoverpa zea*), Mediterranean corn borer (*Sesamia nonagroides*), cabbage looper (*Trichoplusia ni*), velvetbean caterpillar (*Anticarsia gemmatalis*), diamondback moth (*Plutella xylostella*) and tobacco budworm (*Heliothis virescens*).

Also provided by the invention is a method of controlling insects wherein the transgenic plant or microorganism further comprises a second DNA sequence which encodes a second insecticidal protein such as those mentioned hereinbefore.

The invention further provides recombinant DNA sequences which encode a VIP3A(c) protein including homologues thereof. In another preferred embodiment, the DNA sequence is a synthetic sequence which has been altered for optimum expression in a plant, particularly where the DNA sequence has been optimized for expression in a maize plant. Also preferred are DNA sequences which comprise both a synthetic portion and a native portion. In a particularly preferred embodiment, the DNA sequence encoding the VIP3A(c) protein has been optimized for expression in a maize plant. Another preferred embodiment are DNA sequences which are homologous to a DNA sequence which encodes a VIP3A(c) protein. Particularly preferred are DNA sequences which hybridize under moderately stringent conditions to the vip3A(c) coding sequence. Yet another embodiment of the invention is a recombinant DNA sequence which expresses a protein of the VIP3 class, preferably a VIP3A(c) protein, under the control of a heterologous promoter, or wherein the coding regions is incorporated into the genome of an organism where it is not naturally expressed or is expressed at higher levels than that occuring naturally.

The invention is further drawn to a method of identifying and isolating homologues of a VIP3A(c) protein. or of a DNA sequence which encodes said protein.

Also provided by the invention are expression cassettes comprising a promoter operably linked to a DNA sequence encoding a protein of the VIP3 class, but preferably a VIP3A(c) protein. In one preferred embodiment the promoter is selected from the group consisting of constitutive, tissue-preferred and tissue-specific promoters for expression in plants. In a particularly preferred embodiment, the promoter is selected from the group consisting of the ubiquitin, PEP carboxylase, LPT and MTL promoters. In another preferred embodiment, the promoter is functional in a microorganism.

The invention further provides a receptor to a protein of the VIP3 class and DNA sequences which. In one embodiment of the invention, the receptor comprises a death domain and a repeated EGF-motif. A more preferred embodiment of the invention comprises a receptor to the VIP3A(a). A more particularly preferred embodiment is the receptor protein sequence set forth in SEQ ID NO:9, and homologues thereto. Also encompassed by the invention are DNA sequences which encode these receptor proteins, e.g., the DNA sequence set forth in SEQ ID NO:8 and homologues thereto. The cDMA for the VIP3 receptor is contained in plasmid pCIB7113, which was deposited under the Budapest Treaty with the NRRL [Agricultural Research Service, Patent Culture Collection (NRRL), Northern Regional Research Center, 1815 North University Street, Peoria, Ill. 61604, USA] on Mar. 29, 1997 and has accession number B-21676. Antibodies to a receptor of the VIP3 class of proteins are also encompassed by the invention.

Also provided by the invention is a method of identifying a compound as a VIP3 receptor chemical ligand having pesticidal activity comprising exposing a cell, preferably an insect cell, to a test compound, and assaying said cell for apoptotic activity. In another embodiment of the invention, the method comprises measuring specific binding between VIP3 receptor and a test compound. A preferred embodiment are VIP3 receptor ligands identified by the method.

DEFINITIONS

"Plant pest" means any organism known to associate with plants and which, as a result of that association, causes a detrimental effect on the plant's health and vigor. Plant pests include but are not limited to fungi, bacteria, insects, and nematodes. The term plant as used herein encompasses whole plants and parts of plants such as roots, stems, leaves and seed, as well as cells and tissues within the plants or plant parts.

The "VIP3 class of proteins" comprises VIP3A(a), VIP3A(b) VIP3A(c) and their homologues. "Homologue" is used throughout to mean that the indicated protein or polypeptide bears a defined relationship to other members of the VIP3 class of proteins. This defined relationship includes but is not limited to, 1) proteins which are at least 70%, more preferably 80% and most preferably 90% identical at the sequence level to another member of the VIP3 class of proteins while also retaining pesticidal activity, 2) proteins which are cross-reactive to antibodies which immunologically recognize another member of the VIP3 class of proteins, 3) proteins which are cross-reactive with a receptor to another member of the VIP3 class of proteins and retain the ability to induce programmed cell death, and 4) proteins which are at least 70%, more preferably 80% and most preferably 90% identical at the sequence level to the toxic core region of another member of the VIP3 class of proteins while also retaining pesticidal activity.

A "hybrid toxin " is used to indicate a genetic fusion, having domains operably linked so that, when translated, a functional chimeric protein is formed having, in the aggregate, the properties of the individual domains. "Domain" is used to indicate a region or portion of a protein or confers a recognizable function or structure which contributes to the overall functionality of the protein. It is recognized that a DNA sequence which encodes a protein domain is also encompassed by this definition.

"Heterologous" is used to indicate that a protein, polypeptide or nucleotide sequence has a different natural origin with respect to its current host. For example, if a vip3A(a) gene from a *Bacillus thuringiensis* is genetically transformed into a plant cell, then the gene is described as being heterologous with respect to its current host, which is the plant cell. Furthermore, if a vip3A(a) gene from *Bacillus thuringiensis* is genetically transformed into a Pseudomonas bacterium, then the gene is also described as being heterologous with respect to the Pseudomonas. "Heterologous" is also used to indicate that one or more of the domains present in a chimeric protein, polypeptide or nucleotide sequence differ in their natural origin with respect to other domains present. For example, if the toxic domain from VIP3A(a) protein is fused to the binding domain from the VIP1A(a) protein to make a functional insecticidal protein, then the chimeric fusion would have domains that are heterologous to each other. In addition, a heterologous chimeric protein or polypeptide comprising the fusion of a toxic domain from VIP3A(a) protein to the binding domain from the VIP1A(a) protein, when expressed in a plant, would also be considered heterologous with respect to the plant host.

The term "chimeric" is used to indicate that the protein, polypeptide, or nucleotide sequence is comprised of domains at least one of which has an origin that is heterologous with respect to the other domains present. These chimeric proteins or polypeptide are encoded by chimeric nucleotide sequences which have been fused or ligated together resulting in a coding sequence which does not occur naturally. Such chimeric constructions may also be designated as "recombinant."

"Expression cassette" as used herein means a DNA sequence capable of directing expression of a gene in plant cells, comprising a promoter operably linked to an amino acid coding region which is operably linked to a termination region. The gene may be chimeric, meaning that at least one component of the gene is heterologous with respect to at least one other component of the gene. The gene may also be naturally occurring, but which has been obtained in a recombinant form useful for genetic transformation of a plant or microorganism.

FIGURES

FIG. 1: Amino acid sequence of the receptor for VIP3A(a) translated from the cDNA. Several features of the protein are shown: doffed line—signal peptide (amino acid 13 to 35); italic—domain spanning the putative death domain (amino acid 81–205); double underline—sequences with strong homology to sequences found in consensus death domains; bold—CKC motif repeated six times spanning the EGF-motifs; underline—sequences repeated within the EGF-motifs.

ARTHROPOD PESTS

For purposes of the present invention, pests include insects and arachnids selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, and Acari, particularly Coleoptera and Lepidoptera.

A list of pests associated with major crop plants are provided; for example, in Tables 1–10 on pages 13 to 20 of WO 96/10083, which is incorporated herein by reference. Further pests are provided in the following Tables 1–8. Such pests are included within the scope of the present invention.

TABLE 1

| Lepidoptera (Butterflies and Moths) | |
|---|---|
| Maize | Crucifers (broccoli, cabbage, cauliflower, collards) |
| *Sesamia nonagroides*, Mediterranean corn borer | *Artogeia rapae*, imported cabbageworm |
| | *Pieris brassicae*, cabbage butterfly |
| *Ostrinia tumacails*, Asian corn borer | *Trichoplusia ni*, cabbage looper |
| Cotton | *Plutella xylostella*, diamondback moth |
| *Helicoverpa armigera*, cotton bollworm | *Spodoptera exigua*, beet armyworm |
| Rice | *Agrotis ipsilon*, black cutworm |
| *Chilo suppressalis*, asiatic rice borer | *Agrotis segetum*, common cutworm |
| *Scirpophaga* sp. | *Mamestra configura*, bertha army worm |
| Tomato | Grapes |
| *Heilcoverpa zea*, tomato fruitworm | *Endopiza*, grape berry moth |
| *Spodpptera exigua*, beet armyworm | Deciduous Fruits and Nuts |
| *Spodoptera frugiperda*, fall armyworm | *Cydia pomoneia*, codling moth |
| *Spodoptera omithogalli*, yellowstriped armyworm | *Platynota idaeusalis*, tufted apple bud moth |
| | Peppers |
| *Spodoptera praefica*, western yellowstriped armyworm | *Ostrinia nubilalis*, European corn borer |
| | *Spodoptera exigua*, beet armyworm |
| *Spodoptera eridania*, southern armyworm | *Spodoptera eridania*, southern armyworm |
| | Potato |
| *Agrotis ipsilon*, black cutworm | *Ostrinia nubilalis*, European corn borer |

TABLE 1-continued

Lepidoptera (Butterflies and Moths)

| | |
|---|---|
| *Peridroma saucia*, variegated cutworm | *Phthorimaea operculella*, potato tubeworm |
| *Papaipema nebris*, stalk borer | Canola |
| *Trichoplusia ni*, cabbage looper | *Plutella xylostella*, diamondback moth |
| *Kefferia lycopersicella*, tomato pinworm | Sugarcane |
| *Manduca sexta*, tobacco hornworm | *Diatraea saccharalis*, sugarcane borer |
| *Manduca quinquemaculata*, tomato hornworm | |

TABLE 2

Coleoptera (Beetles)

| | |
|---|---|
| Rice | Potato |
| *Oulema oryzae*, rice beetle | *Leptinotarsa decemlineata*, Colorado potato beetle |
| Tomato | *Epitrix cucumeris*, potato flea beetle |
| *Leptinotarsa decemlineata*, Colorado potato beetle | *Hemicrepidus memnonius*, wire-worms |
| *Epitrix hirtipennis*, tobacco flea beetle | Melanpotus spp., wireworms |
| Crucifers (broccoli, cabbage, cauliflower, collards) | Canola |
| *Phyllotreta cruciferae*, crucifer flea beetle | *Ceutorhychus assimillis*, cabbage seedpod weevil |
| *Phyllotreta puslilla*, western black flea beetle | *Phylloterta cruciferae*, crucifer flea beetle |
| Peppers | |
| *Anthonomus eugenii*, pepper weevil | |

TABLE 3

Homoptera (whiteflies, Aphids etc . . . )

| | |
|---|---|
| Rice | Melon |
| *Nilaparvata lugens* | *Bemisia argentifolii*, silverleaf whitefly |
| *Sogatella furcifera* | *Bemisia tabaci*, sweetpotato whitefly |
| *Laodelphaax striatellus* | |
| Tomato | Carrot |
| *Myzus persicae*, green peach aphid | *Cavariella aegopodii*, carrot aphid |
| *Macrosiphum euphorbiae*, potato aphid | Canola |
| *Trileurodes vaporariorum*, greenhouse whitefly | *Brevicoryne brassicae*, cabbage aphid |
| *Bemisia tabaci*, sweetpotato whitefly | Vegetables |
| *Bemisia argentifolii*, silverleaf whitefly | *Aphis fabae*, bean aphid |
| Crucifers (broccoli, cabbage, cauliflower, collards) | Sugar Beet |
| *Brevicoryne brassicae*, cabbage aphid | *Pemphigus pullivenae*, sugar beet root aphid |
| *Myzus persicae*, green peach aphid | Deciduous Fruits and Nuts |
| Peppers | *Dysaphis plantaginea*, rosy apple aphid |
| *Myzus persicae*, green peach aphid | Sugarcane |
| Potato | *Saccharosydne saccharivora*, West Indian canefly |
| *Empoasca fabae*, potato leafhopper | *Sipha flava*, yellow sugarcane aphid |
| *Myzus persicae*, green peach aphid | |
| *Macrosiphum euphorbiae*, potato aphid | |
| *Paratrioza cockerelli*, potato psyllid | |

TABLE 4

Hemiptera (Bugs)

Tomato
lygus bug
*Acrosternum hilare*, green stink bug
*Euschistus servus*, brown stick bug

TABLE 5

Orthoptera (Grasshoppers, Crickets, and Cockroaches)

Wheat
*Melanoplus sanguinipes*, migratory grasshopper

TABLE 6

Diptera (Flies and Mosquitoes)

| | |
|---|---|
| Tomato | Carrot |
| *Liriomyza trifolii*, leafminer | *Psilia rosae*, carrot rust fly |
| *Liriomyza sativae*, vegetable leafminer | Sugarbeet |
| *Scrobipalpula absoluta*, tomato leafminer | *Tetanops myopaeformis*, sugar-beet root maggot |
| Crucifers (broccoli, cabbage, cauliflower, collards) | Vegetables |
| *Delia brassicae*, cabbage maggot | *Liviomyza sativae*, vegetable leaf miner |
| *Delia radicum*, cabbage root fly | |

TABLE 7

Thysanoptera (Thrips)

| | |
|---|---|
| Tomato | Peppers |
| *Frankliniella occidentakis*, western flower thrips | *Thrips palmi*, melon thrips |
| *Frankliniella fusca*, tobacco thrips | Potato |
| *Thdps tabaci*, onion thrips | *Thrips palmi*, melon thrips |
| Crucifers (broccoli, cabbage, cauliflower, collards) | |
| *Thrips tabaci*, onion thrips | |

TABLE 8

Acari (Mites and Ticks)

Tomato
*Tetranychus urticae*, two-spotted spider mite
*Aculops lycopersici*, tomato russet mite
*Steneotarsonemus pallidus*, cyclamen mite
Citrus
*Panonychus citri*, citrus red mite
*Brevipalpus lewisi*, citrus flat mite
*Phyllocoptrutra oleivora*, citrus rust mite
Deciduous Fruits and Nuts
*Panonychus ulmi*, European red mite
*Tetrancnus sp*, spider mite For purposes of the present invention, pests also include fungal phytopathogens of plants. A list of fungal pests associated with major crop plants is provided in Table 9. Such pests are included within the scope of the present invention.

TABLE 9

Fungal Diseases of Plants

| | |
|---|---|
| Ear Molds | |
| Gibberella ear mold | *Gibberella zeae* |
| | *G. saubinetti* |
| Aspergillus ear rot | *Aspergillus flavus* |
| | *A. parasiticus* |
| Diplodia ear rot | *Diplodia maydis* |
| | *D. macrospora* |
| Fusarium ear rot | *Fusarium moniliforme* |
| | *F. monilif.* var. subglutinans |
| Stalk Rots | |
| Pythium stalk rot | *Pythium aphanidermata* |
| Anthracnose stalk rot | *Colletotrichum graminicola* |
| | *C. tucumanensis* |
| | *Glomerella graminicola* |
| Diplodia stalk rot | *Diplodia maydis* |
| | *D. zeae-maydis* |
| | *Stenocarpella maydis* |
| | *Macrodiplodia zeae* |
| | *Sphaeria maydis* |
| | *S. zeae* |
| | *D. macrospora* |
| Fusarium stalk rot | *Fusarium moniliforme* |
| Gibberella stalk rot | *G. zeae* |
| | *G. saubinetti* |
| Stewart's wilt & leaf blight | *Erwinia stewartii* |
| Leaf Diseases | |
| Northern corn leaf blight | *Exserohilum turcicum* |
| Southern corn leaf blight | *Bipolaris maydis* |
| Gray leaf spot | *Cercospora zeae-maydis* |
| | *C. sorghi* var. maydis |
| Anthracnose leaf blight | *Colletotrichum graminicola* |
| Common rust | *Puccinia sorghi* |
| | *P. maydis* |
| Southern rust | *Puccinia polysora* |
| | *Dicaeoma polysorum* |
| Head smut | *Sphacelotheca reiliana* |
| Common smut | *Ustilago maydis* |
| Carbonum leaf spot | *Helminthosprium carbonum* |
| Eye spot | *Kabatiella zeae* |
| Downy Mildews | |
| Sorghum downy mildew | *Peronosclerospora sorghi* |
| Brown stripe downy mildew | *Sclerophthora rayssiae* |
| Sugarcane downy mildew | *Peronosclerospora sacchari* |
| Phillipine downy mildew | *Peronoscler. philippinensis* |
| Java downy mildew | *Peronosclerospora maydis* |
| Spontaneum downy mildew | *Peronoscierospora spontanea* |
| Rajasthan downy mildew | *Peronosclerospora heteropogoni* |
| Graminicola downy mildew | *Sclerospora graminicola* |
| Rusts | *Puccinia graminis* f.sp. tritici |
| | *Puccinia recondita* f.sp. tritici |
| | *Puccinia striformis* |
| Smuts | *Tilletia tritici* |
| | *Tilletia controversa* |
| | *Tilletia indica* |
| | *Ustilago tritici* |
| | *Urocystis tritici* |
| Root rots, Foot rots and Blights | *Gaeumannomyces graminis* |
| | Pythium spp. |
| | *Fusarium culmorum* |
| | *Fusarium graminaerum* |
| | *Fusarium avenaceum* |

TABLE 9-continued

Fungal Diseases of Plants

| | |
|---|---|
| | *Drechslere tritici-repentis* |
| | Rhizoctonia spp. |
| | *Colletotrichum graminicola* |
| | Helminthosporium spp. |
| | *Microdochium nivale* |
| | *Pseudocercosporella herpotrichoides* |
| Mildews | *Erysiphe graminis* f.sp. tritici |
| | *Sclerophthora macrospora* |
| Miscellaneous Fungal Diseases | *Septoria tritici* |
| | *Septoria nodorum* |

The proteins of the VIP3 class are secreted to the media by Bacillus spp. in vegetative stages of growth. VIP3A(a) is a member of a newly discovered class of proteins displaying insecticidal activity against a broad spectrum of lepidopteran insects including black cutworm (*Agrotis ipsilon*), fall armyworm (*Spodoptera frugiperda*), beet armyworm (*S. exigua*), yellow striped armyworm (*S. omithogalli*), southwestern corn borer (*Diatraea grandioselia*), sugarcane borer (*D. saccharalis*), corn earworm (*Helicoverpa zea*), Mediterranean corn borer (*Sesamia nonagroides*), cabbage looper (*Trichoplusia ni*), velvetbean caterpillar (*Anticarsia gemmatalis*), diamondback moth (*Plutella xylostella*) and tobacco budworm (*Heliothis virescens*). Some of these lepidopteran insects have been shown to be very resistant to other insecticidal proteins such as δ-endotoxin. For example, the reported $LC_{50}$ for Cry1A(c), which is one of the most effective δ-endotoxin against black cutworm, is greater than 6000 ng/cm$^2$ (Macintosh et al., J. Invertebr. Pathol. 56:258–266 (1990)). in contrast, it takes 260-fold less of VIP3A(a) protein to kill 50% of the black cutworm larvae. Thus, the VIP3A(a) protein displays a unique spectrum of insecticidal activities.

The present invention provides a new member of the VIP3 class of proteins, the VIP3A(c) protein isolated from strain AB51 (pCIB7112 deposited on Mar. 28, 1997 as Accession No. NRRL B-21675; all deposits were made in accordance with the Budapest Treaty by submission to the Agricultural Research Service, Patent Culture Collection (NRRL), Northern Regional Research Center, 1815 North University Street, Peoria, Ill. 61604, USA) as disclosed in SEQ ID NO:5–6.

The VIP3A(c) protein encoding DNA sequence was identified and isolated s through the use of PCR technology. In particular, primer sequences can be made which recognize either conserved or variable regions of the coding sequence, and are then used to screen DNA samples obtained from either known or unknown strains. It is recognized that there are multiple approaches to identifying and isolating homologues within the VIP3 class of proteins and the DNA sequences which encode them, which approaches are well known to those skilled in the art.

The DNA and protein sequences for the VIP3A(a) and VIP3A(c) proteins are aligned in Table 12.

TABLE 12

Alignment of VIP3A(a) (Upper Line) against VIP3A(c) (Lower Line)

```
1 MNKNNTKLSTRALPSFIDYFNGIYGFATGIKDIMNMIFKTDTGGDLTLDE   50 SEQ ID NO:2
  |||||·||||||||||||||||||||||||||||||||||||||||||·|||
1 MNKNNAKLSTRALPSFIDYFNGIYGFATGIKDIMNMIFKTDTGGDLALDE   50 SEQ ID NO:6
```

TABLE 12-continued

Alignment of VIP3A(a) (Upper Line) against VIP3A(c) (Lower Line)

```
 51 ILKNQQLLNDISGKLDGVNGSLNDLIAQGNLNTELSKEILKIANEQNQVL 100
    ||.|||||||||||||||||||||||||||||||||||||||||||||||
 51 ILENQQLLNDISGKLDGVNGSLNDLIAQGNLNTELSKEILKIANEQNQVL 100

101 NDVNNKLDAINTMLRVYLPKITSMLSDVMKQNYALSLQIEYLSKQLQEIS 150
    ||||||||||||||||||||||||||||||||||||||||||||||||||
101 NDVNNKLDAINTMLRVYLPKITSMLSDVMKQNYALSLQIEYLSKQLQEIS 150

151 DKLDIINVNVLINSTLTEITPAYQRIKYVNEKFEELTFATETSSKVKKDG 200
    ||||||||||||||||||||||||||||||||||||||||||||||||||
151 DKLDIINVNVLINSTLTEITPAYQRIKYVNEKFEELTFATETSSKVKKDG 200

201 SPADILDELTELTELAKSVTKNDVDGFEFYLNTFHDVMVGNNLFGRSALK 250
    |||||/|||.|||||||||||||.||||||||||||||||||||||||||
201 SPADIRDELSELTELAKSVTQNDVDGFEFYLNTFHDVMVGNNLFGRSALK 250

251 TASELITKENVKTSGSEVGNVYNFLIVLTALQAQAFLTLTTCRKLLGLAD 300
    |||||||||||||||||||||||||||||||||||||||||.||||||||
251 TASELITKENVKTSGSEVGNVYNFLIVLTALQAQAFLTLTPCRKLLGLAD 300

301 IDYTSIMNEHLNKEKEEFRVNILPTLSNTFSNPNYAKVKGSDEDAKMIVE 350
    ||||||||||||||||||||||||||||||||||||||||||||||||||
301 IDYTSIMNEHLNKEKEEFRVNILPTLSNTFSNPNYAKVKGSDEDAKMIVE 350

351 AKPGHALIGFEISNDSITVLKVYEAKLKQNYQVDKDSLSEVIYGDMDKLL 400
    ||||||||||||||||||||||||||||||||||||||||||||||||||
351 AKPGHALIGFEISNDSITVLKVYEAKLKQNYQVDKDSLSEVIYGDMDKLL 400

401 CPDQSEQIYYTNNIVFPNEYVITKIDFTKKMKTLRYEVTANFYDSSTGEI 450
    |||||:||||||||||||||||||||||||||||||||||||||||||||
401 CPDQSGQIYYTNNIVFPNEYVITKIDFTKKMKTLRYEVTANFYDSSTGEI 450

451 DLNKKKVESSEAEYRTLSANDDGVYMPLGVISETFLTPINGFGLQADENS 500
    ||||||||||||||||||||||||||||||||||||||||||||||||||
451 DLNKKKVESSEAEYRTLSANDDGVYMPLGVISETFLTPINGFGLQADENS 500

501 RLITLTCKSYLRELLLATDLSNKETKLIVPPSGFISNIVENGSIEEDNLE 550
    ||||||||||||||||||||||||||||||||||||||||||||||||||
501 RLITLTCKSYLRELLLATDLSNKETKLIVPPSGFISNIVENGSIEEDNLE 550

551 PWKANNKNAYVDHTGGVNGTKALYVHKDGGISQFIGDKLKPKTEYVIQYT 600
    ||||||||||||||||||||||||||||||||||||||||||||||||||
551 PWKANNKNAYVDHTGGVNGTKALYVHKDGGISQFIGDKLKPKTEYVIQYT 600

601 VKGKPSIHLKDENTGYIHYEDTNNNLEDYQTINKRFTTGTDLKGVYLILK 650
    ||||||||||||||||||||||||||||||||||||||||||||||||||
601 VKGKPSIHLKDENTGYIHYEDTNNNLEDYQTINKRFTTGTDLKGVYLILK 650

651 SQNGDEAWGDNFIILEISPSEKLLSPELINTNNWTSTGSTNISGNTLTLY 700
    ||||||||||||||||||||||||||||||||||||||||||||||||||
651 SQNGDEAWGDNFIILEISPSEKLLSPELINTNNWTSTGSTNISGNTLTLY 700

701 QGGRGILKQNLQLDSFSTYRVYFSVSGDANVRIRNSREVLFEKRYM     746
    |||||||||||||||||||||||||||||||||||||||||||:  :
701 QGGRGILKQNLQLDSFSTYRVYFSVSGDANVRIRNSREVLFEKKDI     746
```

Polypeptide Domains of the VIP3 Class of Proteins

It has been shown that the VIP3A(a) protein undergoes proteolytic processing when mixed with the gut fluids of insect larvae. When gut fluids isolated from black cutworm are mixed with purified VIP3A(a), four major proteolytic products derived from VIP3A(a) can be identified having a molecular weight of approximately 66, 45, 33 and 22 kDa. The 22 kDa band comprises the N-terminal portion of the VIP3A(a) protein from amino acid 1 to amino acid 198 of SEQ ID NO:2. The 66 kDa band comprises the rest of the VIP3A(a) protein from amino acid 200 to amino acid 789 of SEQ ID NO:2. Both the 45 and 33 kDa bands are derived by proteolysis from the 66 kDa band and constitute amino acid 412 to amino acid 789, and from amino acid 200 to amino acid 455, respectively, of SEQ ID NO:2. The 33 kDa band is the main component of the VIP3A(a) protein that remains after an incubation period of more than two hours. This 33 kDa "toxic core" domain (amino acids 200 to 455 of SEQ ID NO:2) of the VIP3A(a) protein retains full insecticidal properties against a broad spectrum of lepidopteran insects. Similar results are obtained when VIP3A(a) is incubated with gut fluids isolated from fall armyworm, another insect sensitive to VIP3A(a).

In addition to the toxic core domain, the VIP3A(a) protein also possesses a stabilizing domain at the C-terminus. The role of the stabilizing domain was explored using mutants of the VIP3A(a) protein and the VIP3A(c) protein, neither of which display insecticidal properties when ingested by insects known to be sensitive to VIP3A(a). When similar studies addressing the stability in black cutworm gut fluid was conducted with VIP3A(a)-mutants, in particular with a mutant of the VIP3A(a) protein that contains three point mutations located at the carboxy-terminal domain (amino acid 742 (E→D); amino acid 770 (S→P); and amino acid 784 (Y→H)), it was found that the protein was completely hydrolyzed. Similar results were obtained for the VIP3A(c) (SEQ ID NO:6) protein isolated from AB51, which shares an overall identity of 96% with the VIP3A(a) protein but lacks the carboxy-terminal domain of VIP3A(a). Both the mutant and VIP3A(c) protein, however, are active against the insect cell line Sf-9. These results indicate that the function of the carboxy-terminal domain of proteins of the VIP3 class is to provide stability to the protein in the gut environment of susceptible insects.

Hybrid Toxins Comprising a VIP3 Region and a Heterologous Region

Toxins, enzymes, transcription factors, antibodies, cell binding moieties or other protein domains can be operably linked to the novel proteins of the present invention by producing in frame genetic fusions which, when translated by ribosomes, would produce a fusion protein with the combined attributes of the VIP and the other component used in the fusion. Furthermore, if the protein domain fused to the VIP has an affinity for another protein, nucleic acid, carbohydrate, lipid, or other chemical or factor, then a three-component complex can be formed. This complex will have the attributes of all of its components. A similar rationale can be used for producing four or more component complexes. These complexes are useful as insecticidal toxins, pharmaceuticals, laboratory reagents, and diagnostic reagents, etc. Examples where such complexes are currently used are fusion toxins for potential cancer therapies, reagents in ELISA assays and immunoblot analysis.

The hybrid toxins of the invention include chimeric proteins having a toxic core domain which is heterologous to the stabilizing domain. Hybrid toxins are also created by combining an antibody, or immunologically-active fragment thereof, which immunologically recognizes the VIP3 receptor with a toxic domain from other proteins. The toxin domain is obtained from a number of cytotoxic proteins. These include but am not limited to Bacillus toxins, including endotoxins and vegetative insecticidal proteins. See for example U.S. application Ser. No. 08/037,057, filed Mar. 25, 1993 and U.S. application Ser. No. 07/951,715 filed Sep. 25, 1992, herein incorporated by reference. Other toxins include catalytic ribosome inactivators such as gelonin, Pseudomonas exotoxin A or phytolaccin, (the structure of Pseudomonas exotoxin has been well characterized in Chaudhary et al., J. Biol. Chem. 265:16303–16310 (1990)); cell metabolism disrupters, such as ribonucleases, (see, for example, Mariani et al. Nature 347:737–741 (1990)); Bamase toxin (or PE-Bar), a chimeric toxin derived from Pseudomonas exotoxin A and a ribonuclease, (see, Prior et al. Cell 64:1017–1023 (1991)); hydrophilic peptides that create pores in membranes (see, Frohlich and Wells, Int. J. Peptide Protein Res. 37:2–6 (1991)).

Mode of Action of VIP3A(a)

The VIP3A(a) protein has been shown to be active against a broad spectrum of plant pests. For example, histopathological observations indicate that VIP3A(a) ingestion by susceptible insects such as black cutworm (*Agmtis ipsilon*) and fall armyworm (*Spodoptera frugiperda*) causes gut paralysis at concentrations as low as 4 ng/cm$^2$ of diet, with complete lysis of the gut epithelial cells resulting in larval death at concentrations above 40 ng/cm$^2$. Less susceptible insects like European corn borer (*Ostrinia nubilalis*) do not develop any pathology upon ingesting VIP3A(a). While the proteolytic processing of the VIP3A(a) protein by midgut fluids obtained from susceptible and non-susceptible insects is comparable, in vivo immuno-localization studies show that VIP3A(a) binding is restricted to gut cells of susceptible Insects. Therefore, the insect host range for VIP3A(a) seems to be determined by its binding ability to gut cells. Histopathological observations indicate that midgut epithelial cells of susceptible insects are the primary target for the VIP3A(a) insecticidal protein and their subsequent lysis is the primary mechanism of lethality.

Programmed cell death is an active process of self-destruction that seems to be important for development and maintenance of multicellular organisms (Clem, R. J. et al. Science 254: 1388–1390 (1991)). Cells undergoing apoptosis, which is a form of programmed cell death, generate membrane-bound apoptotic bodies and activate endogenous nucleases that cleaves the chromatin into discrete fragments. SF-9 insect cells derived from *S. frugiperda* exposed to the VIP3A(a) protein undergo a series of cytological and molecular changes including membrane protrusions, profuse vacuolization and endonucleolysis which are Indicative of an apoptotic-type of programmed cell death. Histological studies have shown that the VIP3A (a) protein targets midgut epithelial cells of susceptible insects initiating a series of cytological changes comprising profuse vacuolization and swelling prior to cell lysis and larval death. These midgut cells also experienced an endonucleolysis process when exposed to the VIP3A(a) protein as revealed by in situ detection of DNA fragmentation. These results indicate that VIP3A(a) exerts its insecticidal properties on susceptible insect cells by triggering an apoptotic-type of programmed cell death.

The Receptor for VIP3A(a) has been Isolated

The immunohistochemistry results provided above indicate that VIP3A(a) has the ability to bind to the apical membranes of midgut epithelial cells and that this binding triggers the process that will eventually end with cell lysis. This indicates that there exists one or more proteins located in the apical membrane that recognize and bind to VIP3A(a) acting as a receptor. This receptor signals the interaction with VIP3A(a) and triggers the process of apoptosis. Thus, the receptor will mediate the response of the insect cell to VIP3A(a).

To isolate this receptor, a cDNA library was screened which was made from mRNA isolated from midgut tissue of black cutworm. The objective of the screen was to identify and isolate cDNA sequences which encode proteins that will interact with VIP3A(a) in the two hybrid system (see Fields, S. and Song, O.-K. Nature 340:245–246 (1989)). This approach resulted in the identification and isolation of one cDNA whose encoded protein strongly interacted with the VIP3A(a) protein. This 1.75 Kb-long cDNA (SEQ ID NO:8) encodes a protein of approximately 48 kDa (396 amino acids; see SEQ ID NO:9). The cloned cDNA is similar in size to the mRNA encoding the cDNA as analyzed by Northern. A portion of the DNA sequence which encodes the first 5 to 20 amino acids may be missing. The following features can be identified in the cDNA encoded protein (see FIG. 1): 1) it contains a signal peptide; 2) it contains a domain with homology to the so-called death domain (Feinstein, E. et al Trends in Biochem. 20:342–344 (1995)); and 3) it contains EGF-like motifs or repeats (Fantl, W. J. et al. Annu. Rev. Biochem. 62:453–481 (1993)). A search of protein databases using the receptor of VIP3A(a) showed homology with a family of extracellular glycoproteins known as Tenascins (Pearson, C. A. et al. EMBO J.

7:2677–2681 (1988)) or Hexabrachion (Nies, D. E. et al J. Biol. Chem. 266:2818–2823 (1991)). This family of proteins contains EGF-like repeats, interacts with multiple ligands, and performs a role in cell adhesion and/or signaling. The combination of a death domain and repeated EGF-motifs as observed in the VIP3 receptor is unique among programmed cell death receptors.

In addition, a portion of the VIP3A(a) receptor shares homology with the so-called "death domain." The death domain is a 60 to 70 amino acid long motif which is involved in protein to protein interaction and is shared by proteins with diverse cellular functions (Feinstein, E. et al. Trends in Biochem. 20:342–344 (1995)). Some of the protein members containing death domain motifs include receptors known to be associated with apoptotic processes. Some examples include the Fas receptor (Brakebush, C. et al. EMBO J. 11:943–950 (1992)) and the tumor necrosis factor (TNF) (Tartaglia, L. A. et al. Cell 74:845–853 (1993)).

Homologues to the VIP3A(a) receptor can be identified and isolated by various means, for example, by nucleic acid hybridization. Southern blot analysis can be performed on DNA samples taken from insect cells or fungal cells that has been enzyme restricted, run in agarose and blotted onto nitrocellulose and/or nylon filters. The Southern blot can be probed with the full-or partial length of the nucleic acid encoding the receptor of the VIP3A(a) protein under low stringency hybridization and washing conditions. The genes can be readily cloned and sequenced from a cDNA or genomic library. A size-selected genomic library can also be obtained to facilitate cloning of the gene(s) of interests. The technical protocols to perform the experiments outlined above are readily available (see for instance Molecular Cloning, A Laboratory Manual, Second Edition, Vols. 1–3, Sambrook et al. (eds.) Cold Spring Harbor Laboratory Press, Cold Spring Harbor, N.Y. (1989) and reference therein).

Antibodies to VIP3A(a) and its Receptor

Polyclonal and monoclonal antibodies to a VIP3 protein or its receptor, including fragments thereof which immunologically recognize a portion of either protein, are provided. The antibody and monoclonal antibodies of the present invention can be prepared by utilizing a VIP3 protein or its receptor as the antigen.

The antibodies of the invention include polyclonal and monoclonal antibodies as well as fragments thereof which retain their ability to bind a VIP3 protein or its receptor. An antibody, monoclonal antibody, or fragment thereof is said to be capable of binding a molecule if it is capable of specifically reacting with the molecule to thereby bind the molecule to the antibody, monoclonal antibody, or fragment thereof. The term "antibody" (Ab) or "monoclonal antibody" (Mab) is meant to Include intact molecules as well as fragments or binding regions or domains thereof (such as, for example, Fab and F(ab)$_2$ fragments) which are capable of binding hapten. Such fragments are typically produced by proteolytic cleavage, such as papain or pepsin. Alternatively, hapten-binding fragments can be produced through the application of recombinant DNA technology or through synthetic chemistry.

Methods for the preparation of the antibodies of the present invention are generally known in the art. For example, see Antibodies, A Laboratory Manual, Ed Harlow and David Lane (eds.) Cold Spring Harbor Laboratory, N.Y. (1988), as well as the references cited therein. Standard reference works setting forth the general principles of immunology include: Klein, J. Immunology: The Science of Cell-Noncell Discrimination, John Wiley & Sons, N.Y. (1982); Dennet, R., et at Monoclonal Antibodies, Mybridoma: A New Dimension in Biological Analyses, Plenum Press, N.Y. (1980); and Campbell, A. "Monoclonal Antibody Technology," In Laboratory Techniques in Biochemistry and Molecular Biology, Vol. 13, Burdon et al. (eds.), Elsevier, Amsterdam (1984). See also, U.S. Pat. Nos: 4,609, 893; 4,713,325; 4,714,681; 4,716,111; 4,716,117; and 4,720, 459.

It is recognized that following the methods described herein, antibodies specific for a particular VIP3 protein or its receptor can be generated. The subset of MAb lines which possess the desired binding specificity can be used as a source of messenger RNA for cloning of the cDNA for the particular monoclonal antibody.

The cloned DNA can then be sequenced by methods known in the art. See, for example, Sambrook et al., Molecular Cloning: A Laboratory Manual, 2nd. Edition, Cold Spring Harbor Laboratory Press, N.Y. (1989) vol. 1–3, and the references cited therein. From the nucleic acid sequence, the protein sequence of the binding region from the selected MAb can be deduced.

One use of the antibodies and monoclonal antibodies of the invention includes but is not limited to the production of hybrid toxin molecules. That is, when linked, the monoclonal antibody or antibody fragment retains its binding properties and the toxin moiety retains its cytotoxic properties.

Various methods are known for obtaining antibody genes. One method is to clone a random library of antibody genes in a phage and screen the library for ability to bind to a VIP3 protein or its receptor. Another available approach is to generate monoclonal antibodies which bind to a VIP3 protein or its receptor and then clone the antibody genes from such lines. For the present example, the second method is used. Antibody genes can be cloned from hybridoma cells using primers to conserved DNA sequences within the constant regions and the framework regions of the variable regions and amplified for cloning using the polymerase chain reaction (PCR). See generally, Mullis et al., Meth. Enzymol., 155:335–350 (1987); Erlich, (ed.), PCR Technology, Stockton Press (New York 1989). A database of mouse heavy chain and light chain sequences compiled by Kabat et al., U.S. Dept Health and Human Services, U.S. Government Printing Offices (1991) has been successfully used to generate both isotype specific and degenerate primers for cloning antibody genes. (Jones et al. Bio/technology 9:88–89 (1991)). Additionally, techniques are well known for cloning of smaller fragments of antibodies (Fab) which possess the binding properties of the original antibody. Complete antibodies are large molecules (150 kDa), but much smaller Fab and Fv antigen-binding fragments (12 kDa-50 kDa) have been shown to retain full binding affinity. Single chain Fv fragments (scFv) in which Vh and Vl domains are linked by a hydrophilic and flexible peptide have been used successfully to target enzymes and toxins to specific cells (Bird, Science 423:423–426 (1988); Huston, PNAS 85:5879–5883 (1988)). Single Vh domains (Dabs) and single complementary determining regions as small as 20 amino acids in length, called minimal recognition units (m.r.u.), have also been used for antigen binding (Ward, Nature 341:544–546 (1989); Taub, J. Biol. Chem 264:259–265 (1989); Williams, PNAS 86:5537–5541 (1989)). Thus, it is possible to reduce the binding domain specific for a VIP3 or its receptor to a very small size.

Polymerase chain reaction technology and specific oligonucleotide primers are used to clone immunoglobulin genes or regions from immunoglobin genes. PCR primers specific for both the heavy and light chains of IgM and the three IgG isotypes were selected from the Kabat database described above. Primers for the region encoding the $NH_2$-terminal end of the mature variable region were designed to initiate at the first framework region and were made with some degeneracy to allow these to be used as "universal primers". The 3' primers used for the specific PCR amplification of the variable regions were designed from conserved sequences of the first constant domain (CH1) of both the light and heavy chains. A different 3' primer is used for immunoglobulin isotypes IgG1, IgG3, and IgM. Isotypes IgG2A and IgG2B can be amplified with the same primers used for IgG1. Antibody variable regions are cloned into a light and heavy chain expression vector containing an endoplasmic reticulum signal peptide and the constant regions of IgG1 light and heavy chains, respectively.

Primer sequences used for the PCR cloning of the mouse immunoglobulin light and heavy variable regions are available in the published literature (Coloma et al. Bio/Techniques 11: 152–156 (1991); Jones et al. Bio/Technology 9:88–89 (1991)). Oligonucleotides were made on an Applied Biosystems DNA synthesizer 380B (Applied Biosystems, Foster City, Calif.) using standard conditions as described below. The PCR primers incorporate restriction sites and, after amplification and digestion, can be cloned into a plant expression vector under the control of a plant-expressible promoter. Restriction sites were chosen that were known to be absent in sequenced antibody genes.

Another use of the polyclonal and/or monoclonal antibodies of the invention includes the stimulation of apoptosis by targeting the receptor to Vip3A with antibodies. The interaction of antibodies raised against cell surface-located proteins that are involved in controlling the cell growth result in the induction of apoptosis by means of preventing the said receptor from binding to its natural ligand(s). For instance, the anti-APO-1 antibody completely blocks proliferation of leukemia cells bearing the APO-1 protein and triggers apoptosis in these cells (Trauth, B. C. et al. Science 245:301–305 (1989)). Also, the activity resulting from the interaction between a given receptor and a ligand is mimicked by substituting the ligand for antibodies raised against the receptor. For instance, the addition of certain anti-Fas antibodies to cells bearing the Fas receptor in their cell surfaces will mediate apoptosis in a similar fashion as when the ligand of the Fas receptor is added (Itoh, N. et al. Cell 66:233–243 (1991)).

The receptor to Vip3A(a) isolated from black cutworm shares homology with a family of extracelular glycoproteins known as Tenascins, and in particular with Tenascin-X (Bristow, J. et al. J. Cell Biol. 122:265–278 (1993)). Tenascin-Xs are known to be involved in cell-to-cell adhesion and signaling. Lack of functionality of Tenascin-X either by mutation or by removal of the gene leads to lethality. Therefore, antibodies raised against different domains of the receptor to Vip3A(a) either effectively block the receptor from binding to its ligand(s) or mimic the interaction of the Vip3A(a) protein triggering apoptosis. This approach is extended to different receptors with similar biological functions. In this sense, antibodies raised against insect cell receptors Involved in crucial cell growth and interaction processes lead to induction of apoptosis and are used as an strategy to control insects.

Screening for Novel Insecticidal Activities whose Mode of Action is Apoptosis

The materials described in this invention are used to screen for chemical ligands that have pesticidal properties triggering apoptotic responses. Chemical ligands include small organic molecules, peptides, and proteins. In one embodiment of the invention, insect cell lines are used as model organisms for insects to screen for compounds that are insecticidal as a consequence of their ability to induce apoptosis. These cell lines are handled in a high-throughput screening format where the cells are grown in multi-well plates and are exposed to a variety of compounds. Yeast is also used as a model organism. Using procedures described herein or known in the art, determining whether a compound is pesticidal as a consequence of inducing apoptosis is accomplished.

One means by which to identify compounds that trigger apoptotic responses through interaction with a known receptor is to resort to identified receptors involved in the signal transduction pathway triggered in apoptotic insect cell lines. These receptors are transformed into heterologous cell lines creating isogenic lines with one of them containing a gene for expression of a specific receptor and another one which does not either possess, or express, such a gene. These cell lines are handled in a high-throughput screening format whereby the transformed cell lines expressing the receptor have a differential response against compounds that trigger apoptosis through their specific interaction with said receptor.

Also encompassed by the present invention is the characterization of biochemical and/or molecular markers that specifically identify an insect cell line undergoing apoptosis. For example, it is possible to isolate specific cDNAs induced during an apoptotic process in specific insect cell lines. Although the death core pathway seems to be phylogenetically conserved (Nagata, S. Cell 88:355–365 (1997)), the signal transduction pathway from the receptor to the death core pathway is subject to variation across organisms. Messenger RNAs differentially expressed in insect cells undergoing apoptosis are identified by a number of techniques readily available such as differential display (Bauer, D. et al. Nucleic Acid Res. 21:4272–4280 (1993)) or subtractive libraries (Sommer, H. et al. EMBO J. 9:605–613 (1990)). The differentially expressed cDNA-encoded proteins are used as markers for apoptosis in specific insect cell lines.

Transgenic Plants Comprising a DNA Sequence Encoding a Protein of the VIP3 Class A host plant expressing at least one of the sequences of the invention has enhanced resistance to attack by plant pests and is thus better equipped to withstand crop losses associated with such attack. By plant is meant any plant species which can be genetically transformed by methods known in the art. Methods known in the art for plant transformation are discussed below. Host plants include, but are not limited to, those species previously listed as target crops.

PLANT EXPRESSION CASSETTES

Methodologies for the construction of plant expression cassettes as well as the introduction of foreign DNA into plants are described in the art. Such expression cassettes may include promoters, terminators, enhancers, leader sequences, introns and other regulatory sequences operably linked to the pesticidal protein coding sequence. It is further recognized that promoters or terminators of the VIP3 genes can be used in expression cassettes.

Toxin genes derived from microorganisms may also differ from plant genes. Plant genes differ from genes found in microorganisms in that their transcribed RNA does not possess defined ribosome binding site sequence adjacent to the initiating methionine. Consequently, microbial genes can be enhanced by the inclusion of a eukaryotic consensus translation initiator at the ATG (Kozak, Cell 44:283–292 (1986)). Clontech (1993/1994 catalog, page 210) has suggested the sequence GTCGACCATGGTC (SEQ ID NO:-) as a consensus translation initiator for the expression of the *E. coli* uidA gene in plants. Further, Joshi (Nucleic Acids Res. 15: 6643–6653 (1987)) has compared many plant sequences adjacent to the ATG and suggests the consensus TAAACAAMGCT (SEQ ID NO:-). In situations where difficulties are encountered in the expression of microbial ORFs in plants, inclusion of one of these sequences at the initiating ATG may improve translation. In such cases the last three nucleotides of the consensus may not be appropriate for inclusion in the modified sequence due to their modification of the second AA residue. Preferred sequences adjacent to the initiating methionine may differ between different plant species. By surveying the sequence of maize genes present in the GenBank/EMBL database It can be discerned which nucleotides adjacent to the ATG should be modified to enhance translation of the toxin gene introduced into maize.

In addition, it has been shown that removal of illegitimate splice sites can enhance expression and stability of introduced genes. Genes cloned from skilled in the art will appreciate that the choice of method might depend on the type of plant, i.e. monocot or dicot, targeted for transformation. Suitable methods of transforming plant cells are described, for example, in WO 96/10083 and WO 97/46105, respectively, including microinjection, electroporation, Agrobactedurn-mediated transformation, direct gene transfer, and ballistic particle acceleration using devices available from Agracetus, Inc., Madison, Wis. and Dupont, Inc., Wilmington, Del.

An preferred embodiment is the protoplast transformation method for maize as disclosed in European Patent Application EP 0 292 435, as well as in U.S. Pat. No. 5,350,689, hereby incorporated by reference in its entirety. One particularly preferred set of embodiments for the introduction of the expression cassettes of the present invention into wheat by microprojectile bombardment can be found in U.S. Pat. No. 5,610,042 herein incorporated by reference in its entirety.

Transformation of plants can be undertaken with a single DNA molecule or multiple DNA molecules (i.e. co-transformation), and both these techniques are suitable for use with the expression cassettes of the present invention. Numerous transformation vectors are available for plant transformation, and the expression cassettes of this invention can be used in conjunction with any such vectors. The selection of vector will depend upon the preferred transformation technique and the target species for transformation.

Many vectors are available for transformation using *Agrobactedium tumefaciens*. These typically carry at least one T-DNA border sequence and include vectors such as pBIN19 (Bevan, Nucl. Acids Res. (1984)). In one preferred embodiment, the novel toxin gene of the present invention may be inserted into either of the binary vectors pCIB200 and pCIB2001 for use with Agrobadterium, the construction of which is disclosed, for example, in WO 95133818 (example 35) (see also EP 0 332 104, example 19).

An additional vector useful for Agrobadterium-mediated transformation is the binary vector pCIB10 contains a gene encoding kanamycin resistance for selection In plants, T-DNA right and left border sequences and incorporates sequences from the wide host-range plasmid pRK252 allowing it to replicate in both *E. coli* and Agmbactedum. Its construction is described by Rothstein et al. (Gene 53: 153–161 (1987)). Various derivatives of pCIB10 have been constructed which incorporate the gene for hygromycin B phosphotransferase described by Gritzret al. (Gene 25:179–188 (1983)). These derivatives enable selection of transgenic plant cells on hygromycin only (pCIB743), or hygromycin and kanamycin (pCIB715, pCIB717).

Methods using either a form of direct gene transfer or Agrobacterium-mediated transfer usually, but not necessarily, are undertaken with a selectable marker which may provide resistance to an antibiotic (e.g., kanamycin, hygromycin or methotrexate) or a herbicide (e.g., phosphinothricin). The choice of selectable marker for plant transformation is not, however, critical to the invention unless the expression of this resistance and its biochemical activity interferes with the choice of protoxin to toxin conversion chosen for use in creating conditional fertility.

For certain plant species, different antibiotic or herbicide selection markers may be preferred. Selection markers used routinely in transformation include the nptll gene which confers resistance to kanamycin and related antibiotics (Messing & Vierra, Gene 19: 259–268 (1982); Bevan et al., *Nature* 304:184–187 (1983)), the bar gene which confers resistance to the herbicide phosphinothricin (White et al., *Nuc Acids Res* 18:1062 (1990), Spencer et al., *Theor Appl Genet* 79:625–631(1990)), the hph gene which confers resistance to the antibiotic hygromycin (Blochinger & Diggelmann, *Mol Cell Biol* 4: 2929–2931), the dhfr gene, which confers resistance to methotrexate (Bourouis et al., *EMBO J*. 2: 1099–1104 (1983)), the mannose phosphate isomerase gene, which allows selection on mannose as a carbon source (EP 530 129,WO 94/20627).

One such vector useful for direct gene transfer techniques in combination with selection by the herbicide Basta (or phosphinothricin) is pCIB3064. This vector is based on the plasmid pCIB246, which comprises the CaMV 35S promoter in operational fusion to the *E. coli* GUS gene and the CaMV 35S transcriptional terminator and is described in the PCT published application WO 93/07278, herein incorporated by reference. Another useful selectable marker is obtained by operably linking a ubiquitin promoter, a synthetic PAT gene and a nos terminator. Once example of a vector comprising this marker is the plasmid pCIB9804.

An additional transformation vector is pSOG35 which utilizes the *E. coli* gene dihydrofolate reductase (DHFR) as a selectable marker conferring resistance to methotrexate and the construction of which is described, for example, in WO 95/33818 (example 35)

Another transformation vector is the vector pGL2 (Shimamoto et al. Nature 338, 274–276 (1989)) which contains the Streptomyces hygromycin phosphotransferase gene (hpt) operably linked to the 35S promoter and 35S terminator sequences.

Transgenic plants can also be identified through the use of a scorable marker. Examples of scorable markers useful in the invention are β-glucuronidase, green fluorescent protein, and the C1 and B-peru regulatory genes of the maize anthocyanin pathway. In addition, transgenic plants expressing a VIP3 protein can be identified by screening them for insecticidal activity without the need for either scorable or selectable markers.

Transformation of maize with a DNA sequence encoding a protein of the VIP3 class, but preferably a VIP3A(c) protein according to any of the above methods can be readily achieved by microprojectile bombardment of either immature zygotic embryos or serially-propagatable Type I embryogenic callus.

For transformation using immature zygotic embryos, ears are self-pollinated and immature zygotic embryos are obtained approximately 10 days later. Approximately eight hundred immature zygotic embryos are divided among different target plates containing a medium capable of inducing and supporting the formation of embryogenic callus. The immature zygotic embryos are transferred immediately to the same medium but containing 12% sucrose. After 5 hours, the immature zygotic embryos are bombarded with a plasmid or plasmids using the PDS-1000/He device from Bio-Rad. The plasmid or plasmids comprise a selectable marker, such as a gene conferring resistance to phosphinothricin, or a scorable marker, such as green fluorescent protein, and a gene encoding a protein of the VIP3 class prepared for delivery to and expression in maize according to the above description. The plasmid or plasmids are precipitated onto 1 μm gold particles essentially according to the published procedure from BioRad. The particles are delivered using a burst pressure of 1550 psi of helium. Each target plate is shot twice with the plasmid and gold particle preparation. Since in one embodiment of the invention the plasmid or plasmids comprise a chimeric gene coding for resistance to phosphinothricin this substance could be used to select transformed cells in vitro. If used, the selection agent is applied at 10 mg/L on the day of gene delivery and increased to 40 mg/L after approximately one month. The embryogenic callus so obtained may be regenerated in the presence of the selection agent phosphinothricin if the selectable marker is used. Plants are obtained from the selected embryogenic callus lines. The regenerated plants are assayed for resistance to a susceptible insect. All the plants that are resistant to the insect also express the introduced chimeric gene encoding a protein or proteins of the VIP3 class as evidenced by the detection of VIP3 protein in the plant using an ELISA assay. Plants resistant to the insect and expressing the VIP3 protein are transformed.

For transformation of maize using Type I embryogenic callus, the callus is obtained from immature zygotic embryos using standard culture techniques. For gene delivery, approximately 300 mg of the Type I callus is prepared by either chopping with a scalpel blade or by subculturing 3–5 days prior to gene delivery. Prior to gene delivery, the prepared callus is placed onto semi-solid culture medium again containing 12% sucrose. After approximately 4 hours, the tissue is bombarded using the PDS-1000/He Biolistic device from BioRad. The plasmid or plasmids comprise a selectable marker, such as a gene conferring resistance to phosphinothricin, or a scorable marker, such as green fluorescent protein, and a gene encoding a protein of the VIP3 class prepared for delivery to and expression in maize according to the above description. The plasmids are precipitated onto 1 $\mu$m gold particles using essentially the standard protocol from BioRad. Approximately 16 hours after gene delivery the callus is transferred to standard culture medium containing 2% sucrose and, if the selectable marker is used, to 1 mg/L phosphinothricin. The callus is subcultured on selection for 8 weeks, after which surviving and growing callus is transferred to standard regeneration medium for the production of plants. The regenerated plants are assayed for resistance to a susceptible insect. All the plants that are resistant to the insect also express the introduced chimeric gene encoding a protein of the VIP3 class as evidenced by the detection of VIP3 protein in the plant using an ELISA assay. Plants resistant to the insect and expressing a protein of the VIP3 class are transformed.

SUPPLEMENTAL INSECT CONTROL PRINCIPLES

The pesticidal proteins of the invention can be used in combination with Bt $\delta$-endotoxins or other insecticidal proteins to increase Insect target range. Furthermore, the use of the VIPs of the present invention, but preferably of the VIP3A(c) protein, in combination with Bt $\delta$-endotoxins or other insecticidal principles of a distinct nature has particular utility for the prevention and/or management of insect resistance.

The various insecticidal crystal proteins from *Bacillus thuringiensis* have been classified based upon their spectrum of activity and sequence similarity. The classification put forth by Hafte and Whiteley, Microbiol. Rev. 53: 242–255 (1989) placed the then known insecticidal crystal proteins into four major classes. Generally, the major classes are defined by the spectrum of activity, with the Cry1 proteins active against Lepidoptera, Cry2 proteins active against both Lepidoptera and Diptera, Cry3 proteins active against Coleoptera, and Cry4 proteins active against Diptera.

Within each major class, the $\delta$-endotoxins are grouped according to sequence similarity. The Cry1 proteins are typically produced as 130–140 kDa protoxin proteins which are proteolytically cleaved to produce active toxin proteins about 60–70 kDa. The active portion of the $\delta$-endotoxin resides in the $NH_2$-terminal portion of the full-length molecule. Höfte and Whiteley, supra, classified the then known Cry1 proteins into six groups, 1Aa, 1Ab, 1Ac, 1B, 1C, and 1D. Since then, proteins classified as Cry1Ea, Cry1Fa, Cry9A, Cry9C and Cry9B have also been characterized.

The spectrum of insecticidal activity of an individual $\delta$-endotoxin from *Bacillus thuringiensis* tends to be quite narrow, with a given $\delta$-endotoxin being active against only a few insects. Specificity is the result of the efficiency of the various steps involved in producing an active toxin protein and its subsequent ability to interact with the epithelial cells in the insect digestive tract. In one preferred embodiment, expression of VIPs in a transgenic plant is accompanied by the expression of one or more Bt $\delta$-endotoxins. Particularly preferred Bt $\delta$-endotoxins are those disclosed in U.S. application Ser. No. 07/951,715, herein incorporated by reference.

It is well known that many $\delta$-endotoxin proteins from *Bacillus thuringionsis* are actually expressed as protoxins. These protoxins are solubilized in the alkaline environment of the insect gut and are proteolytically converted by proteases into a toxic core fragment (Höfte and Whiteley, Microbiol. Rev. 53: 242–255 (1989)). For $\delta$-endotoxin proteins of the Cry1 class, the toxic core fragment is localized in the N-terminal half of the protoxin. It is within the scope of the present invention that genes encoding either the full-length protoxin form or the truncated toxic cord fragment of the novel toxin proteins can be used in plant transformation vectors to confer insecticidal properties upon the host plant.

Other insecticidal principles include protease Inhibitors (both serine and cysteine types), lectins, $\alpha$-amylase, peroxidase and cholesterol oxidase. Other VIP genes, such as vip1A(a) and vip2A(a) as disclosed in U.S. Ser. No. 08/463,483 and herein incorporated by reference, are also useful in the present invention.

This co-expression of more than one insecticidal principle in the same transgenic plant can be achieved by genetically engineering a plant to contain and express all the genes necessary. Alternatively, a plant, Parent 1, can be genetically engineered for the expression of VIPs. A second plant, Parent 2, can be genetically engineered for the expression of a supplemental insect control principle. By crossing Parent 1 with Parent 2, progeny plants are obtained which express all the genes introduced into Parents 1 and 2.

Recombinant Microorganisms Comprising Genes and Proteins of the VIP3 Class

It is recognized that the isolated genes of the present invention which encode a protein of the VIP3 class, but preferably a VIP3A(c) protein, can be transferred into any microbial host and confer their insecticidal properties upon that host. Alternate hosts for the novel genes of the present invention can be selected as suitable for cloning purposes, for purposes of characterizing the form and function of the gene or encoded protein, for use as a fermentation host to increase production of the toxin protein, for purposes of delivering at least one of the toxin proteins more effectively to the target insect pest, or introduction of the novel toxin gene into insect pathogens such as baculovirus (a nuclear polyhedrosis virus, e.g. *Autographica califomica*) to improve their effectiveness.

It is envisioned that said alternate host would be applied to the environment or plants or animals for insect control. Microorganism hosts may be selected which are known to occupy the "phytosphere" (phylloplane, phyllosphere, rhizosphere, and/or rhizoplana) of one or more crops of interest. These microorganisms are selected so as to be capable of successfully competing in the particular environment with the wild-type microorganisms, provide for stable maintenance and expression of the gene expressing the polypeptide pesticide, and, desirably, provide for improved protection of the pesticide from environmental degradation and inactivation.

Such microorganisms include bacteria, algae, and fungi. Of particular interest are microorganisms, such as bacteria, e.g., Bacillus, Caulobacter, Agmenellum, Pseudomonas, Erwinia, Serratia, Klebsiella, Xanthomonas, Streptomyces, Rhizobium, Rhodopseudoionas, Methylius, Agrobacterium, Acetobacter, Lactobacillus, Arthrobacter, Azotobacter, Leuconostoc, and Alcaligenes, fungi, particularly yeast, e.g., Saccharomyces, Cryptocoacus, Kluyveromyces, Sporobolomyces, Rhodotorula, and Aurlobasidium. Of particular interest are such phytosphere bacterial species as Bacillus spp., *Pseudomonas syringae, Pseudomonas fluotescens, Senatia marcescens, Acetobacter xylinum,* Agrobacteria, *Rhodopseudomonas spheroides, Xanthomonas campestris, Rhizobium melioti, Acaligenes entrophus, Clavibacter xyli* and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces rosues, S. odorus, Kluyveromyces veronae,* and *Aureobasidium pollulans*. Of particular interest are the pigmented microorganisms.

Suitable host cells, where the pesticide-containing cells will be treated to prolong the activity of the toxin in the cell when the then treated cell is applied to the environment of the target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and -positive, include Enterobacteriaceae, such as Escherichia, Erwinia, Shigella, Salmonella, and Proteus; Bacillaceae; Rhizobiceae, such as Rhizobium; Spirillaceae, such as photobacterium, Zymomonas, Serratia, Aeromonas, Vibrio, Desulfovibrio, Spirillum; Lactobacillaceae; Pseudomonadaceae, such as Pseudomonas and Acetobacter, Azotobacteraceae and Nitrobacteraceae. Among eukaryotes are fungi, such as Phycomycetes and Ascomycetes, which includes yeast, such a Saccharomyces and Schizosaccharromyces; and Basidiomycetes yeast, such as Rhodotorula, Aureobasidium, Sporobolomyces, and the like.

Characteristics of particular interest in selecting a host cell for purposes of production include ease of introducing the protein gene into the host, availability of expression systems, efficiency of expression, stability of the protein in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as Rhodotorula sp., Aureobasidium sp., Saccharomyces sp., and Sporobolomyces sp.; phylloplane organisms such as Pseudomonas sp., Erwinia sp. and Flavobacterium sp.; or such other organisms as Escherichia, LactoBacillus sp., Bacillus sp., and the like. Specific organisms include *Pseudomonas aeurginosa, Pseudomonas fluorescens, Saccharomyces cerevisiae, Bacillus thuringiensis, Escherichia coli, Bacillus subtilis*, and the like.

A number of ways are available for introducing a gene expressing the pesticidal protein into the microorganism host under conditions which allow for stable maintenance and expression of the gene. For example, expression cassettes can be constructed which include the DNA constructs of interest operably linked with the transcriptional and translational regulatory signals for expression of the DNA constructs, and a DNA sequence homologous with a sequence in the host organism, whereby integration will occur, and/or a replication system which is functional in the host, whereby integration or stable maintenance will occur.

Transcriptional and translational regulatory signals include but are not limited to promoter, transcriptional initiation start site, operators, activators, enhancers, other regulatory elements, ribosomal binding sites, an initiation codon, termination signals, and the like. See, for example, U.S. Pat. No. 5,039,523; U.S. Pat. No. 4,853,331; EPO 0480762A2; Sambrook et al. supra; Molecular Cloning, a Laboratory Manual, Maniatis et al. (eds) Cold Spring Harbor Laboratory, Cold Spring Harbor, N.Y. (1982); Advanced Bacterial Genetics, Davis et al. (eds.) Cold Spring Harbor Laboratory, Cold Spring Harbor, N.Y. (1980); and the references cited therein.

The novel genes or recombinant forms thereof can be transformed into such alternate hosts using a variety of art recognized methods. One such preferred method is electroporatlon of microbial cells, as described, for example, by the method of Dower (U.S. Pat. No. 5,186,600). Another preferred method is that of Schurter et al. (Mol. Gen. Genet. 218: 177–181 (1989)), which is also disclosed in U.S. Ser. No. 07/353,565 which is incorporated herein in its entirety.

Genes encoding the VIP3 class of proteins can be introduced into microorganisms that multiply on plants (epiphytes) or in plants (endophytes) to deliver proteins of the VIP3 class to potential target pests. Many bacterial species are capable of living In the vascular tissues of plants. Most of these endophytes and epiphytes appear to have little physiological impact on plant growth and productivity.

Root colonizing bacteria, for example, can be isolated from the plant of interest by methods known in the art. Specifically, a Bacillus cerous strain which colonizes roots could be isolated from roots of a plant (for example see J. Handelsman, S. Raffel, E. Mester, L. Wunderlich and C. Grau, Appl. Environ. Microbiol. 56:713–718, (1990)). Vip3 genes can also be introduced into a root colonizing Bacillus cereus by standard methods known in the art. Specifically, agene encoding a protein of the VIP3 class derived from strain AB88 can be introduced into a root colonizing Bacillus ceisus by means of conjugation using standard methods (J. Gonzalez, B. Brown and B. Cariton, Proc. Natl. Acad. Sci. 79:6951–6955, (1982)).

Also, the novel genes of the invention can be introduced into the root colonizing Bacillus by means of electrotransformation. For example, vip3A(a) can be cloned into a shuttle vector, for example, pHT3101 (D. Lereclus et al., FEMS Microbiol. Letts., 60:211–218 (1989)). The shuttle vector pHT3101 containing the coding sequence can then be transformed into the root colonizing Bacillus by means of electroporation (D. Lereclus et al. 1989, FEMS Microbiol. Letts. 60:211–218). It is also possible to use the cotton colonizing *Bacillus megaterium.*

Another example is afforded by the endophyte *Clavibacter xyli*, which is from a genus/species known contain phytopathogenic bacteria which cause plant stunting. This bacterium can grow to very high levels in the vascular system of plants. A δ-endotoxin was introduced into this endophyte, which when inoculated into a plant, provided good control of corn borer. Other endophytes are also known.

Expression systems can be designed so that VIP3 proteins are secreted outside the cytoplasm of gram negative bacteria, *E. coli*, for example. Advantages of having VIP3 proteins secreted are (1) it can increase the level of VIP3 protein expressed and (2) can aid in efficient purification of VIP3 protein.

VIP3 proteins can be made to be secreted in *E. coli*, for example, by fusing an appropriate *E. coli* signal peptide to the amino-terminal end of the VIP3 signal peptide or replacing the VIP3 signal peptide with the *E. coli* signal peptide. Signal peptides recognized by *E. coli* can be found in proteins already known to be secreted in *E. coli*, for example the OmpA protein (J. Ghrayeb, H. Kimura, M. Takahara, Y. Masui and M. Inouye, EMBO J., 3:2437–2442 (1984)). OmpA is a major protein of the *E. coli* outer membrane and thus its signal peptide is thought to be efficient in the translocation process. Also, the OmpA signal peptide does not need to be modified before processing as may be the case for other signal peptides, for example lipoprotein signal peptide (G. Duffaud, P. March and M. Inouye, Methods in Enzymology, 153:492 (1987)).

Specifically, unique BamHI restriction sites can be introduced at the amino-terminal and carboxy-terminal ends of the VIP coding sequences using standard methods known in the art. These BamHI fragments can be cloned, in frame, into the vector pIN-III-ompA1, A2 or A3 (J. Ghrayeb, H. Kimura, M. Takahara, H. Hsiung, Y. Masui and M. Inouye, EMBO J., 3:2437–2442 (1984)) thereby creating ompA:VIP fusion gene which is secreted into the periplasmic space. The other restriction sites in the polylinker of pIN-III-ompA can be eliminated by standard methods known in the art so that the VIP3 amino-terminal amino acid coding sequence is directly after the ompA signal peptide cleavage site. Thus, the secreted VIP3 sequence in *E. coli* would then be identical to the native VIP3 sequence.

When the VIP3 native signal peptide is not needed for proper folding of the mature protein, such signal sequences can be removed and replaced with the ompA signal sequence. Unique BamHI restriction sites can be introduced at the amino-termini of the proprotein coding sequences directly after the signal peptide coding sequences of VIP3 and at the carboxy-termini of VIP3 coding sequence. These BamHI fragments can then be cloned into the pIN-III-ompA vectors as described above.

General methods for employing the strains of the invention in pesticide control or in engineering other organisms as pesticidal agents are known in the art. See, for example U.S. Pat. No. 5,039,523 and EP 0480762A2.

VIP3 can be fermented in a bacterial host and the resulting bacteria processed and used as a microbial spray in the same manner that *Bacillus thuringiensis* strains have been used as insecticidal sprays. In the case of a VIP3 which is secreted from Bacillus, the secretion signal is removed or mutated using procedures known In the art. Such mutations and/or deletions prevent secretion of the VIP3 protein(s) into the growth medium during the fermentation process. The VIP3 proteins are retained within the cell and the cells are then processed to yield the encapsulated VIP3 protein. Any suitable microorganism can be used for this purpose. Psuedomonas has been used to express *Bacillus thuringiensis* endotoxins as encapsulated proteins and the resulting cells processed and sprayed as an insecticide. (H. Gaertner et al. 1993, In Advanced Engineered Pesticides, L. Kim ed.)

Various strains of *Bacillus thuringiensis* are used in this manner. Such Bt strains produce endotoxin protein(s) as well as VIPS. Alternatively, such strains can produce only VIP3. A sporulation deficient strain of *Bacillus subtilis* has been shown to produce high levels of the Cry3A endotoxin from *Bacillus thuringiensis* (Agaisse, H. and Lereclus, D., "Expression in *Bacillus subtilis* of the *Bacillus thuringiensis* CryIIIA toxin gene is not dependent on a sporulation-specific sigma factor and is increased in a spoOA mutant", J. Bacteriol., 176:4734–4741 (1994)). A similar spoOA mutant can be prepared in *Bacillus thuringiensis* and used to produce encapsulated VIP3 which are not secreted into the medium but are retained within the cell.

Target crops to be protected within the scope of the present invention comprise, e.g., the following species of plants:

cereals (wheat, barley, rye, oats, rice, sorghum and related crops), beet (sugar beet and fodder beet), forage grasses (orchardgrass, fescue, and the like), drupes, pomes and soft fruit (apples, pears, plums, peaches, almonds, cherries, strawberries, raspberries and blackberries), leguminous plants (beans, lentils, peas, soybeans), oil plants (rape, mustard, poppy, olives, sunflowers, coconuts, castor oil plants, cocoa beans, groundnuts), cucumber plants (cucumber, marrows, melons) fiber plants (cotton, flax, hemp, jute), citrus fruit (oranges, lemons, grapefruit, mandarins), vegetables (spinach, lettuce, asparagus, cabbages and other Brassicae, onions, tomatoes, potatoes, paprika), lauraceae (avocados, carrots, cinnamon, camphor), deciduous trees and conifers (e.g. linden-trees, yew-trees, oak-trees, alders, poplars, birch-trees, firs, larches, pines), or plants such as maize, tobacco, nuts, coffee, sugar cane, tea, vines, hops, bananas and natural rubber plants, as well as ornamentals (including composites).

The microorganisms which have been genetically altered to contain the pestcidal gene and protein may be used for protecting agricultural crops and products from pests. In one aspect of the invention, whole, i.e., unlysed, cells of a toxin (pesticide)-producing organism are treated with reagents that prolong the activity of the toxin produced in the cell when the cell is applied to the environment of target pest(s).

Alternatively, the pesticides are produced by introducing a heterologous gene into a cellular host. Expression of the heterologous gene results, directly or indirectly, in the intracellular production and maintenance of the pesticide. These cells are then treated under conditions that prolong the activity of the toxin produced in the cell when the cell is applied to the environment of target pest(s). The resulting product retains the toxicity of the toxin. These naturally encapsulated pesticides may then be formulated in accordance with conventional techniques for application to the environment hosting a target pest, e.g., soil, water, and foliage of plants. See, for example EPA 0192319, and the references cited therein.

The active ingredients of the present invention are normally applied in the form of compositions and can be applied to the crop area or plant to be treated, simultaneously or in succession, with other compounds. These compounds can be both fertilizers or micronutrient donors or other preparations that influence plant growth. They can also be selective herbicides, insecticides, fungicides, bactericides, nematicides, mollusicides or mixtures of several of these preparations, if desired, together with further agriculturally acceptable carriers, surfactants or application-promoting adjuvants customarily employed In the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers.

Preferred methods of applying an active ingredient of the present invention or an agrochemical composition of the present invention which contains at least one of the pesticidal proteins produced by the bacterial strains of the present invention are leaf application, seed coating and soil application. The number of applications and the rate of application depend on the intensity of infestation by the corresponding pest.

Entomocidal Compositions Comprising a Recombinant Bacillus thuringiensis Strain

The present invention further provides an entomocidal composition comprising a recombinant *Bacillus thuringiensis* strain containing at least one of the novel toxin genes in recombinant form, or derivatives or mutants thereof, together with an agricultural adjuvant such as a carrier, diluent, surfactant or application-promoting adjuvant. The composition may also contain a further biologically active compound selected from fertilizers, micronutrient donors, plant growth preparations, herbicides, insecticides, fungicides, bactericides, nematicides and molluscicides and mixtures thereof. The composition may comprise from 0.1 to 99% by weight of a recombinant *Bacillus thuringiensis* strain containing at least one of the novel genes in recombinant form, or the derivatives or mutants thereof, from 1 to 99.9% by weight of a solid or liquid adjuvant, and from 0 to 25% by weight of a surfactant. The recombinant *Bacillus thuringiensis* strain containing at least one of the novel genes in recombinant form, or the composition containing it, may be administered to the plants or crops to be protected together with certain other insecticides or chemicals (1993 Crop Protection Chemicals Reference, Chemical and Pharmaceutical Press, Canada) without loss of potency. It is compatible with most other commonly used agricultural spray materials but should not be used in extremely alkaline spray solutions. It may be administered as a dust, a suspension, a wettable powder or in any other material form suitable for agricultural application.

A recombinant *Bacillus thuringiensis* strain containing at least one of the novel genes in recombinant form is normally applied in the form of entomocidal compositions and can be applied to the crop area or plant to be treated, simultaneously or in succession, with further biologically active compounds. These compounds may be both fertilizers or micronutrient donors or other preparations that influence plant growth. They may also be selective herbicides, insecticides, fungicides, bactericides, nematicides, molluscicides or mixtures of several of these preparations, if desired together with further carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. The formulations, i.e. the entomocidal compositions, preparations or mixtures containing the recombinant *Bacillus thuringiensis* strain containing the novel gene in recombinant form as an active ingredient or combinations thereof with other active ingredients, and, where appropriate, a solid or liquid adjuvant, are prepared in known manner, e.g., by homogeneously mixing and/or grinding the active ingredients with extenders, e.g., solvents, solid carriers, and in some cases surface-active compounds (surfactants).

Solvents, carriers, surfactants, surface active compounds, etc that are customarily employed in the art of formulation and can be suitably used within the present invention are disclosed, for example, in WO 96/10083.

Another particularly preferred characteristic of an entomocidal composition of the present invention is the persistence of the active ingredient when applied to plants and soil. Possible causes for loss of activity include inactivation by ultra-violet light, heat, leaf exudates and pH. For example, at high pH, particularly in the presence of reductant, δ-endotoxin crystals are solubilized and thus become more accessible to proteolytic inactivation. High leaf pH might also be important, particularly where the leaf surface can be in the range of pH 8–10. Formulation of an entomocidal composition of the present invention can address these problems by either including additives to help prevent loss of the active ingredient or encapsulating the material in such a way that the active ingredient is protected from inactivation. Encapsulation can be accomplished chemically (McGuire and Shasha, 1992) or biologically (Barnes and Cummings, 1986). Chemical encapsulation involves a process in which the active ingredient is coated with a polymer while biological encapsulation involves the expression of the δ-endotoxin genes in a microbe. For biological encapsulation, the intact microbe containing the δ-endotoxin protein is used as the active ingredient in the formulation. the addition of UV protectants might effectively reduce irradiation damage. Inactivation due to heat could also be controlled by including an appropriate additive.

The entomocidal compositions usually contain 0.1 to 99%, preferably 0.1 to 95%, of a recombinant *Bacillus thuringiensis* strain containing at least one of the novel genes in recombinant form, or combination thereof with other active ingredients, 1 to 99.9% of a solid or liquid adjuvant, and 0 to 25%, preferably 0.1 to 20%, of a surfactant. Whereas commercial products are preferably formulated as concentrates, the end user will normally employ dilute formulations of substantially lower concentration. The entomocidal compositions may also contain further ingredients, such as stabilizers, antifoams, viscosity regulators, binders, tackifiers as well as fertilizers or other active ingredients in order to obtain special effects.

Methods of Controlling Insects

In view of the above description of the invention, it is apparent that there are several methods by which insects may be controlled using proteins of the VIP3 class as an insecticidal principle, either alone or in combination with supplementary insect control principles such as δ-endotoxins. Any method of delivering a VIP3 protein for ingestion by a susceptible insect will result in the control of that insect.

In one embodiment of the invention, plants are transformed with a gene encoding a protein of the VIP3 class. Expression of the protein may occur at any time during growth and development of the plant, depending on the nature of the insect to be controlled. For example, a protein of the VIP3 class can, according to the invention, be expressed in roots, stems, leaves, seeds, pollen, etc. This provides the advantage of expressing the protein only in those cells or tissues upon which the target insect feeds. Feeding the cells or tissues of a plant expressing VIP3 protein to a susceptible insect will result in the control of that insect. In one embodiment of the invention, a VIP3 protein is expressed in the stem or stalk of a plant in order to control black cutworm. The plants may be grown under either field or greenhouse conditions. Seed containing a VIP3 protein can also be protected against insect damage when in storage.

EXAMPLES

Examples 16 to 18 on pages 73 to 82 of WO 96/10083 describe the isolation and biological characterization of *Bacillus thuringiensis* strains AB88 and AB424, the purificatin and characterization of a VIP3A(a) protein, the cloning of vip3A(a) and vip3A(b) genes, and the identification of new vip genes by hybridization. Said Examples are incorporated herein in their entirety by reference. The following examples further describe the materials and methods used in carrying out the invention and the subsequent results. They are offered by way of illustration, and their recitation should not be considered as a limitation of the claimed invention.

Example 1

Presence of vip3-like Genes and VIP3-like Proteins in Bacillus Isolates

Bacillus isolates other than AB88 have demonstrated insecticidal activity against Lepidopteran larvae when spent culture supernatants were tested. Some isolates which were active against black cutworm were analyzed for the presence of vip3-like genes and for the production of VIP3-like proteins.

A standard PCR analysis was used to determine whether the black cutworm-active Bacillus isolates contained a vip3-like gene. Using the PCR primer pair GW110 (5'-CGA TTA ATG TTG GCC TC-3'; SEQ ID NO:17) and GW111 (5'-CAT TAG CAT CTC CGG ACA CAG-3'; SEQ ID NO:18) it was determined that all of the black cutworm active isolates produced a 728 bp vip3 gene product which was equal to the size produced by the type strain, AB88. One Bacillus isolate, AB51, which was not active against black cutworm, produced the same size vip3 product. None of the other non-black cutworm active Bacillus isolates produced a vip3 PCR product.

Analysis of VIP3 protein production was done using a standard western blot procedure. Antibodies raised against the VIP3A(a) protein described in the above example were used to detect immunoreactive proteins. Aliquots of cell free culture supernatants from sporulated cultures were run on SDS-PAGE gels using standard methods. Standard western blotting procedures were then carried out to determine the presence of VIP3-like proteins. All of the Bacillus isolates which had a 728 bp PCR product and were active against black cutworm produced an 80 kDa protein which was immunoreactive to the VIP3A(a) antibody. The AB51 isolate which had the correct size vip3 PCR product but was not active against black cutworm produced an immunoreactive protein which was truncated suggesting this may be the reason no biological activity against black cutworm was observed.

Example 2

Characterization of *Bacillus thuringiensis* Strain AB51 Containing a vip3-like Gene A *B. thuringiensis* strain, designated AB51, was shown to contain proteins of the VIP3 class by western analysis using rabbit polyclonal anti-Vip3A(a) antibodies. The vip3-like gene was cloned into pKS which created pCIB7112. This gene was given the designation vip3A(c). The DNA sequence for vip3A(c) is disclosed in SEQ ID NO:5 and the encoded protein sequence Is disclosed in SEQ ID NO:6. The VIP3A(c) protein is 746 amino acids long, 43 amino acids shorter than its VIP3A(a) and VIP3A(b) homologues.

Example 3

Development of Antibodies to VIP3A(a) Protein

Antiserum against purified Vip3A(a) insecticidal protein was produced in rabbits and goats. For rabbits, nitrocellulose-bound protein (50 μg) was dissolved in DMSO, emulsified with Freund's complete adjuvant (Difco) and injected subcutaneously twice a month for three months. For goats, active soluble pure Vip3A protein (300 μg) was injected intramuscularly twice a month for three month. They were bled 10 days after the second and third injection and the serum was recovered from the blood sample (Hadow, E. and Lane, D. Antibodies: A Manual Laboratory, Cold Spring Harbor Lab. Press, N.Y., 1988). The antiserums were then fractionated by affinity chromatography utilizing staphylococcal protein A, and the resulting IgG fraction was further purified by filtering through a column containing immobilized-*E coli* lysate (Yu, C. G. et al. Appl. Environ. Microbiol. 63:532–536 (1997)).

The rabbit and goat antiserums were characterized analyzing the Vip3A(a) protein by western blot. Proteins were separated by SDS/PAGE and transferred to nitrocellulose. Nitrocellulose blots were blocked in 20 mM Tris-HCl, pH 7.5/0.15 M NaCl/0.02% NaN$_3$/5% nonfat dry milk. Blots were developed by using either rabbit raised or goat-raised anti-Vip3A(a) antibodies at a concentration of 200 ng/ml or 100 ng/ml respectively. Alkaline phosphatase-conjugated goat antirabbit IgG or rabbit antigoat antiserum were used as secondary antibodies at a concentration of 1 μg/ml (Kirkegaard & Perry Laboratories, Inc.). Bromochloroindolyl-phosphate and nitroblue tetrazolium were used as substrate for the alkaline phosphatase reaction. Both anti-Vip3A(a) antibodies, the rabbit and the goat raised, are polyclonal. The anti-Vip3A(a) antibodies obtained from goat have a higher titer than the ones obtained from rabbits. In the experimental approach, anti-Vip3A(a) antibodies from rabbit should be used at a dilution 1/500 from the original serum (200 ng/ml). By comparison, the anti-Vip3A(a) antibodies obtained from goat can be diluted up to 1/2000 (100 ng/ml) from the original serum. While the rabbit raised antibodies only recognize the N-terminal portion of the Vip3A(a) protein, the antibodies obtained from goats react with epitopes present throughout the full length of the Vip3A(a) protein.

Example 4

Construction of Plant Expression Cassettes

Plant expression cassettes consist of promoters that can drive the expression of a coding sequence either constitutively or in a tissue-specific manner, the coding sequences to be expressed and the termination sequences which allow the polyadenylation of the mRNA and its proper translation.

The promoters selected in the DNA constructs of the present invention includes constitutive promoters such as the one from the maize ubiquitin gene (Christensen et al. Plant Mol. Biol. 12:619–632, 1989) (pCIB8029, FIG. 4; pCIB8055, FIG. 5; pCIB9806, FIG. 6), and tissue specific promoters such as those from the maize methalothionein-like gene (de Framond, A. FEBS 290:103–106, 1991) (pCIB8030, FIG. 7; pCIB8056, pCIB9805) which provides a root-preferred expression, from the maize PEPC gene (Hudspeth, R. L. and Grula, J. W. Plant Mol. Boil. 12:579–589,1989) (pCIB5535, FIG. 8; pCIB9807) which provides a green-tissue specific expression, and from the barley non-specific lipid transfer protein LTP4 (pCIB9819, FIG. 9)(Molina, A. and Garcia-Olmedo, F. Plant J. 4:983–991, 1993) which provides a stem-preferred expression. All constructs used in the present invention contain the terminator sequence derived from the 35S CaMV and the intron 9 derived from the maize PEPC gene for enhancing gene expression purposes. The plasmids pCIB8029, pCIB8055, and pCIB9806 contain the intron#1 of the maize ubiquitin gene placed between the maize ubiquitin promoter and the vip3A(a) gene. The construct comprising the encoding sequence of the vip3A(a) gene, the intron#9 and the 35S terminator sequence was engineered into the recipient plasmid bearing the different promoters as double digests BamHI-EcoRI.

The plant expression cassettes were used as such in the plant transformation experiments, or they were linearised by using restriction enzymes that cut in the $Amp^R$ gene of the backbone plasmid. In some experiments, fragments comprising the promoter, gene of interest, intron and terminator were isolated from the rest of the plasmid backbone by restriction digestion and fragment purification. In these cases fragment purification proceeded as follows: 500 ug of DNA is digested with the appropriate enzyme and separated on a 0.8% agarose gel. The fragment of interest is identified, cut out from the gel and purified using a Durapore Millipore filter (0.45 micron). The filtrate containing the fragment is precipitated with sodium acetate and ethanol. The fragment is resuspended in TE and used in transformation experiments.

Example 5

Insecticidal Activity of Maize Plants Expressing VIP3A(a)

Maize plants expressing VIP3A(a) protein were tested for insecticidal effects on the insect species listed in the table below by the following procedure. One to four 4 cm sections were cut from leaves of transgenic and control maize plants. Each leaf piece was placed on a moistened filter disc in a 50×9 mm petri dish. Five neonates of the species being tested were placed on each leaf piece giving a total of 5–20 larvae tested for each plant. The Petri dishes were incubated at 30° C. in the dark. Mortality was scored after 48–72 hours. Results are shown in Table 16.

TABLE 16

| | Percent mortality | |
|---|---|---|
| Insect species tested | VIP3A(a) | Control |
| Maize Pests | | |
| Black cutworm (Agrotis ipsilon) | 100 | 0 |
| Fall armyworm (Spodoptera frugiperda) | 100 | 0 |
| Sugarcane borer (Diatrea saccharalis) | 100 | 0 |
| Southwestern corn borer (Diatraea grandiosella) | 100 | 0 |
| Corn earworm (Helicoverpa zea) | 100 | 10 |
| Mediterranean corn borer (Sesamia nonagroides) | 100 | 15 |

TABLE 16-continued

| | Percent mortality | |
|---|---|---|
| Insect species tested | VIP3A(a) | Control |
| Other Lepidopteran Pests | | |
| Beet armyworm (S. exigua) | 100 | 0 |
| Yellow striped armyworm (S. omithogalli) | 100 | 0 |
| Cabbage looper (Trichoplusia ni) | 100 | 20 |

Example 6

Expression of vip3A(a) in Maize Plants

Transformation of maize elite Ciba inbred lines CG00526 and 2154 with the Vip3 gene was achieved using particle bombardment of Type I callus tissue. For transformation using Type I embryogenic callus, the callus was obtained from zygotic embryos using standard culture techniques and subcultured 1–2 days prior to bombardment. Callus tissue was prepared for bombardment by placing ~20, 3–5 mm diameter pieces arranged in a ring shape onto culture medium containing 12% sucrose. Callus tissue was placed onto this media for four hours prior to bombardment. DNA used for transformation of maize callus was either circular plasmid DNA, linear plasmid DNA, or purified DNA fragments containing the Vip3 gene under control of various plant promoters. In experiments where a selectable agent was used, the gene allowed resistance to phosphinothricin or allowed for growth in the presence of mannose. Plasmids or DNA fragments isolated by filtration were precipitated onto 0.3 um gold particles according to published procedures from BioRad Laboratories, Hercules, Calif. Gold particles were delivered using a burst pressure of 650 psi of helium. Each target plate was shot twice with the DNA coated particles. Sixteen to twenty hours after bombardment the CG00526 callus was transferred to standard culture maintenance media. Seven days post-bombardment the tissue was transferred to media containing the selection agent, Basta at a concentration of 100 mg/L. Basta is a commercial formulation of glufosinate ammonium produced by Hoechst. Callus of 2154 was kept on 12% sucrose for 1–7 days after bombardment and transferred to standard culture media containing 20–30 mg/L Basta at day 7. The 2154 and CG00526 callus was subcultured in the presence of 30 or 100 mg/L Basta, respectively, for eight weeks. Tissue surviving selection was subcultured onto lower levels of Basta (5–40 mg/L) for a period of approximately five to ten weeks to allow for tissue bulk-up and then transferred to a standard regeneration media with no selection for the production of plants. Commonly, 12% of the callus pieces bombarded produced transformed callus that survived Basta selection. Individual transformed calli would typically be regenerated to produce 20–30 plants.

Events were generated from experiments where no selection was used. In these experiments the callus was grown for a period of 9–10 weeks on maintenance media prior to transferring to regeneration media. Event 1337 is an example of a transformed VIP3 event derived from a transformation experiment with no selectable or scorable marker by screening plants for insecticidal activity.

Transformed calli were also generated from experiments where mannose selection was used. In these transformations the phosphomannose isomerase gene under control of the maize ubiquitin promoter of pCIB9818 was bombarded with the Vip3 gene. Mannose at 0.5–1.5% was included in the maintenance media for a period of twelve weeks and not included in the regeneration media.

Transgenic plants were evaluated for VIP3A(a) protein expression by insect bioassay and ELISA assay. Leaf pieces were removed from 2–4 leaf stage plants for evaluation using both black cutworm and fall army worm bioassays. Bioassays were done using ten newly hatched larvae placed in dishes with leaf pieces. Percent mortality was calculated at 72 hours. Tissues from transgenic plants were also assayed by ELISA using standard protocols to quantitate Vip3 protein levels in different plant tissues. Plant tissue was extracted and Table 17 provides representative events generated and their corresponding of insect bioassay results.

Transgenic maize plants were transformed with various plasmids containing the Vip3 gene under control of various promoters such as the maize PEP-carboxylase promoter (PEPC), the maize ubiquitin promoter (Ubi), and the maize metallothionein-like promoter (MTL). The selectable marker gene was the PAT gene under control of the maize ubiquitin promoter in pUBIAC. Representative events listed in Table 17 show the events produced with different plasmids or DNA fragments derived from plasmids. DNA fragments were generated using restriction enyzme digestions and size fractionated using electrophoresis in 0.8% agarose gels. The DNA fragments were excised from the gels, frozen, crushed and purified by filtration through 0.45 micron DuraPore Millipore filters followed by ethanol precipitation. Transformed maize events were generated with circular plasmid DNA of pCIB5535 containing the Vip3 gene under control of the maize PEPC promoter. Events were also transformed with linear plasmid DNA of pCIB5535 and pCIB8029 containing the Vip3 gene under control of the maize ubiquitin promoter. Additional events were produced by bombarding purified DNA restriction enzyme fragments containing just the Vip3 gene with promoter. Fragments corresponding to the Vip3 gene include: a 4906 bp EcoRI/HindIII fragment from pCIB5535 with the maize PEPC promoter; a 5142 bp KpnI/HindIII fragment from pCIB8030 with the MTL promoter; a 4597 bp KpnI/HindIII fragment of pCIB8029 with the maize ubiquitin promoter; a 4818 bp HindIII fragment of pCIB8055 with the maize ubiqutin promoter; a 5364 HindIII fragment of pCIB8056 with the MTL promoter; a 5964 AscI fragment of pCIB9805 with the MTL promoter; a 5418 bp AscI fragment of pCIB9806 with the maize ubiqutin promoter; and a 5727 bp AscI fragment of pCIB9807 with the maize PEPC promoter.

TABLE 17

| | | | Mortality (%) | |
|---|---|---|---|---|
| Event No. | Plasmid Used | Chimeric Gene | Fall Armyworm | Black Cutworm |
| 891 | pCIB5535 | PEPC:vip3A(a) | 100 | 100 |
| 906 | pCIB5535 and pCIB8029 | PEPC:vip3A(a) and Ubi:vip3A(a) | 100 | 100 |
| 946 | pCIB5535 and pCIB8030 | PEPC:vip3A(a) and MTL:vip3A(a) | 100 | 100 |

Example 7

Insecticidal Activity of Maize Plants Containing Vip3 and Bt δ-endotoxins

VIP3A(a) has little activity against European corn borer (ECB). To make plants with broad spectrum lepidopteran control, maize plants containing a vip3A(a) gene were crossed with maize plants containing a cry1B, which is active against ECB. Progeny from the crosses were bioassayed against ECB and fall armyworm (FAW) as described in Example 1. Results are shown in Table 18. Approximately 34% of the progeny were not active against either species, 15.4 % were active only on ECB, 23.1% were active only on FAW and 27.9% were active against both species. Plants active against both species contained both VIP3A(a) and Cry1 B protein. Similar results are obtained using other Bt δ-endotoxins, particularly Cry1Ab or Cry9C.

TABLE 18

| Cross | % ECB active | % FAW active | % ECB & FAW active | % not active |
|---|---|---|---|---|
| VIP3A(a) X Cry1B | 15.4 | 23.1 | 27.9 | 34.6 |

Example 8

VIP3A(a) Lyses the Midgut Epithelial Cells of Susceptible Insects

Feeding and Gut Clearance Studies. The temporal sequence of symptoms following the ingestion of VIP3A(a)-containing diet by second-instar black cutworm (BCW) larvae, a susceptible insect, were recorded from the time of initial administration until larval death. Larvae exposed to control diet showed active feeding followed by uninterrupted gut parastalsis. In contrast, the addition of VIP3A(a) protein in the diet had a significant effect on feeding behavior. When added at concentrations as low as 4 ng per $cm^2$, the larvae ted on and off during periods of 10–20 min. The presence of blue color in their guts indicated feeding but the clearance of the gut content was dramatically affected as judged by the deceased number of frass. With 4 ng of VIP3A(a) per $cm^2$ added to the diet, larval development was significantly impaired after a 48 h incubation period but no mortality was observed. At concentrations of 40 ng of Vip3A(a) per $cm^2$, the larvae suffered gut paralysis upon ingestion of minute amounts of diet and no frass could be seen indicating an almost complete lack of gut clearance. Under this condition, ca. 50% mortality was recorded after 48 hr. When concentrations higher than 40 ng of VIP3A(a) per $cm^2$ were used, the larvae were moribund after only a few bites, with no frass and mortality rates approaching 100%. When similar experiments were conducted with fall armyworm, also a susceptible insect, similar behavioral patterns were observed. In contrast, European corn borer did not alter its feeding behavior when VIP3A(a) protein was added to the diet even at concentrations as high as 400 ng of VIP3A(a) per $cm^2$.

Histological observations of the effects of the Vip3A(a) protein. Histopathological observations on the effects of the VIP3A(a) protein on BCW were conducted on second and third instar larvae which had been fed a diet containing VIP3A(a). Analysis of BCW gut cross-sections showed extensive damage to the midgut epithelium indicating that the midgut tissue is a primary site of action of the Vip3A(a) protein. No damage was discernible in the foregut and hindgut. Midgut epithelial cells from untreated larvae were closely associated with one another showing no evidence of damage. Sections from larvae that had been fed for 24 h with diet containing Vip3A(a) showed that distal ends of the epithelium columnar cells had become distended and bulbous. Although the goblet cells exhibited some morphological alterations, they did not show signs of damage at this stage. Degeneration of the epithelium columnar cells continued such that, after 48 h of ingesting Vip3A(a)-containing diet, the lumen was filled with debris of disrupted cells. The goblet cells also exhibited signs of damage after 48 h, but both types of cells were still attached to the basement membrane. Black cutworm larvae were dead at 72 h and desquamation of the epithelial layer was complete. While a similar histopathology was observed for fall armyworm, European corn borer did not exhibit any tissue damage under similar experimental conditions.

In vivo immunolocalization of the Vip3A(a) protein. Third instar larvae of black cutworm and European corn borer fed on artificial diet supplemented with 100–200 ng of VIP3A(a) per $cm^2$ were used for immunocytochemical characterization of the VIP3A(a) binding to midgut sections. The bound VIP3A(a) was visualized using rabbit anti-VIP3A(a) antibodies previously purified through protein A sepharose and E. coli immobilized columns (Yu, C. G. et al. Appl. Environ. Microbiol. 63:532–536, 1997). VIP3A(a) binding was detected in midgut epithelium of black cutworm, while showing no binding to European corn borer midguts. Midgut sections from black cutworm larvae fed with control diet showed no VIP3A(a) binding. The VIP3A (a) binding seems to be specifically associated to the apical microvilli and it is mostly associated to the columnar cells, with no detectable signal in the goblet cells.

Example 9

VIP3A(a) and VIP3A(b) Induce Apoptosis in Insect Cells

VIP3A(a) and VIP3A(b) were shown to be a apoptosis inducing protein arose by the characterization of its insecticidal effects towards an insect cell line (Sf-9) derived from Spodoptera frugiperda, an insect susceptible to VIP3A(a). VIP3A(a) showed insecticidal activity towards the insect cell line when kept present throughout the experiment. When SF-9 insect cells are transiently exposed to VIP3A(a) and VIP3A(b), their cell viability was significantly reduced even with exposure times as short as 5 min. Once the incubation time exceeded 10 min, the effects of the VIP3A (a) and VIP3A(b) on insect cell viability over a period of 6 hours were maximal showing a reduction of 90% in cell viability. The cytological changes occurring in SF-9 cells transiently exposed to VIP3A(a) were monitored by microscopy. Small protrusions appeared on the surface of the treated cells some time between 10 and 15 min after their exposure to the VIP3A(a) protein. At this stage, the mitochondria of the cells remained functionally intact as revealed by staining with rhodamine 123, a dye that accumulates in mitochondria with active membrane potential (Johnson, L. V. et al. Proc. Natl. Acad. Sci. USA 77:990–994, 1980). These protrusions eventually disappeared and the cells entered a phase of profuse vacuolization lasting an additional 30 to 60 min. During the final stages, the insect cells are seen to swell before disintegration. For an individual cell, the entire process required 1 to 2 hours. All these cellular events are consistent with previous studies on cells undergoing apoptosis particularly considering that programmed cell death during metamorphosis of certain insects is accompanied by cellular vacuolization and swelling (Schwartz, L. M. et al. Proc. Natl. Acad. Sci. USA 90:980–984 (1993)).

Recent studies have shown that the distribution of phospholipids in the plasma membrane is affected in very early stages of animal cells undergoing apoptosis (Martin, S. J., et al. J. Exp. Med.:182, 1545–1556, 1995) particularly the externalization of the phosphatidyiserine (PS). This process can be visualized by using Annexin V, an anticoagulant protein with high affinity for phosphatidyiserine (PS). When VIP3A(a)-treated SF-9 cells were incubated with Annexin V, an externalization of PS was revealed in insect cell membranes as early as 5–10 min after the exposure to VIP3A(a) probably marking the onset of apoptosis.

One of the key molecular events that is the hallmark of apoptosis is endonucleolysis resulting in a double strand DNA break freeing oligonucleosome-sized fragments of 200 base pair and multiples. We examined the occurrence of endonucleolysis in SF-9 cells treated with VIP3A(a) using an in situ detection method and analysing the DNA by agarose gel electrophoresis. Based on the ability of the Klenow enzyme to incorporated modified nucleotides using the DNA ends generated by DNA fragmentation, SF-9 insect cells showed signs of endonucleolysis as early as 30 min upon their exposure to the VIP3A(a) protein. This stage will coincide with the appearance of membrane-bound subcellular apoptotic bodies visualized in the microscopical observations. These early indications of endonucleolytic activity were confirmed by the detection of DNA fragments in agarose gels characteristic of a chromatin ladder slightly latter in the process. These results corroborated the indications obtained from cytological observations, that the SF-9 cells initiate an apoptotic-type of programmed cell death upon their exposure to the VIP3A(a) protein.

The VIP3A(a) and VIP3A(b) proteins were discovered on the basis of their insecticidal properties against some lepidopteran insects. Therefore, we were interested in knowing whether the VIP3A(a) protein would induce an apoptotic pathway in gut cells of susceptible insects upon its ingestion and thus, it could exert its insecticidal properties by triggering an active process of cell death. Histological and histochemical studies have shown that the VIP3A(a) protein specifically targets the columnar cells of the midgut epithelium of susceptible insects provoking cell changes characterized by membrane protrusions and extensive vacuolization leading to cell death. These cytological changes Induced by VIP3A(a) in insect gut cells resemble those described above for SF-9 cells. We then examined whether midgut epithelium cells of susceptible insects undergo endonucleolysis upon ingesting diet containing VIP3A(a) by in situ detection (Cuvillier, O., et al. Nature 381:800–803 (1996)) of DNA fragmentation. When sections of midgut tissue from black cutworm larvae fed with diet either containing VIP3A (a) or control diet, nuclei staining indicative of DNA fragmentaton was only detectable in the columnar cells of the midgut epithelium exposed to the VIP3A(a) protein. This result indicates that the VIP3A(a) protein induces an endonucleolysis process in the midgut epithelium cells concurrently with the cytological changes reported previously. It is our conclusion that the VIP3A(a) protein likely exerts its insecticidal properties by activating an apoptosis-type of programmed cell death of the midgut epithelium cells of susceptible insects.

Example 10

Isolation of the Receptor for VIP3A(a) from Black Cutworm

Black cutworm is sensitive to VIP3A(a) and therefore this insect was used for the isolation of the VIP3A(a) receptor. Midgut of third instar black cutworm larvae were collected by dissection and immediately frozen in liquid nitrogen. One gram of midgut tissue was used to isolate mRNA by following the protocol described in the two-hybrid cDNA library construction kit provided by Clontech (1997). Ten micrograms of poly A$^+$ RNA were used as starting material. In first strand synthesis, both random and lock-docking oligo(dT)$_{25}$d(A/C/G) primers are used in separate synthesis with MML reverse transcriptase. The second strand cDNA was achieved by an optimal ratio of DNA polymerase to Rnase H activity in the second-strand-enzyme cocktail. The newly synthesized double stranded cDNA is then ligated to EcoRI-NotI-SalI adaptors. The cDNAs were ligated into pGAD10 (Vijaychander, S. et al. CLONTECHniques IX-3:8–10,1994) which provides the activation domain. The vip3A(a) gene was engineered into the polylinker site of the plasmid pGBT9 in frame with the GAL4-DNA binding domain (Bartel, P. L. et al. Cellular Interactions in Development: A Practical Approach, pp. 153–179, Oxford University Press, 1993). The recombinant pGBT9-vip3A(a) was transformed into the yeast strain GGY1::171 (Gill, G. and Ptashne, M. Cell51:121–126, 1987) by electroporation (Estruch, J. J. et al. BioTechniques 16:610–612, 1994). The transformed yeast was selected in minimal media without tryptophan (Bartel, P. L. et al. Cellular Interactions in Development: A Practical Approach, pp. 153–179, Oxford University Press, 1993). The expression of the VIP3A(a) protein in the recombinant yeast was confirmed by western analysis. The yeast strain GGY1::171- VIP3A(a) was transformed with the black cutworm cDNA library represented in pGAD10. GGY1::171 possess the HIS3 marker under the control of GAL4 recognition sites. The HIS3 gene allows a positive growth selection for clones that are transformed by two interacting hybrid constructs. After plating more than 200,000 recombinant clones, only one was able to grow in minimal media without histidine. The plasmid DNA of the positive yeast colony was isolated by the yeast lysis buffer method (Kaiser, P. and Auer, B. BioTechniques 14:552 (1993)) and electroporated into E. coli. The insert containing the cDNA was subcloned into the EcoRI site of the pBluescript (Stratagene) and sequenced by the dideoxy termination method of Sanger et al., Proc. Natl. Acad. Sci. USA, 74: 5463–5467 (1977), using PRISM Ready Reaction Dye Deoxy Terminator Cycle Sequencing Kits and PRISM Sequenase® Terminator Double-Stranded DNA Sequencing Kit and analysed on an ABI 373 automatic sequencer.

An alternative approach to identify clones encoding for protein(s) that interact with Vip3A consisted of plating yeast transformed with the black cutworm cDNA library represented in pGAD10. After transferring said transformed yeast population to nitrocellulose filters, they were screened with a biotin-labelled Vip3A protein followed by an incubation with a solution containing streptavidin coupled to alkaline phosphatase (AP). After extensive washes, the clone or clones expressing a protein with the ability to bind to Vip3A were visualized by using the substrate 5-bromo-4-chloro-3-indolyl phosphate (BCIP) in combination with nitro blue tetrazolium (NBT). AP catalizes the formafion of insoluble precipitates which developed in dark spots on the nitrocellulose filters. The experimental procedures are described in detail by Sambrook, J. et al. in Molecular Cloning: A Laboratory Manual, pp. 12–21–12.24, Cold Spring Harbor Laboratory, 1989. After re-growing the yeast plates overnight, the developed spots in the filters were matched to yeast colonies in the original plates. These colonies were grown, their plasmids isolated, and their Inserts characterized as described above.

Example 11

Insect Cells Transformed with the Gene for the Receptor Exhibit Apoptosis when Exposed to the VIP3A(a) Protein The receptor in black cutworm midgut cells for the VIP3A(a) protein was cloned into the XhoI-BamHI site of the Smart 2 cosmid vector (Speek, M. et al. Gene 64: 173–177 (1988)), and the recombinant construct was used to transform the Schneider 2 (S2) Drosophila cell line using the calcium phosphate co-precipitation Method (Clem, R. J. and Miller. L. K. Mol. Cel. Biol.14: 5212–5222 (1994)). Smart 2 carries the selectable marker let (tetracycline) for bacterial transformation and the neo (neomycin) for Drosophila celn transformation. The neo selectable marker is expressed under the control of the Drosophila hsp70 promoter. The transformed S2 cells were selected in S2 Drosophila medium supplemented with 10% of Fetal Seroalbumin and with G418 (1 mg/ml) at 30° C. (see GIBCO catalogue 1997). Several stably transformed S2 cell lines were established after 45 days of selection in the medium described above.

The sensitivity of the S2 transformed cells to the VIP3A (a) was tested by adding VIP3A(a) protein (at a final concentration of 1,7 micrograms per ml) to the media containing the transformed S2 cells that have been previously heat shocked at 42° C. 30 min. The induction of apoptosis in transformed S2 cells was confirmed by both microscopical observations and by the TACS Kit, and in situ Apoptosis Detection kit (for detailed description, see Trevigen catalogue 1996).

Example 12

Isolating Homologues to the Receptor from Other Insects

The cells of the midgut epithelium of black cutworm larvae possess a receptor that is recognized by the VIP3A(a) protein. Receptors from other insects known to be susceptible to VIP3A(a) are isolated by identifying the DNA sequences in Southern analysis. DNA is prepared, enzyme restricted, run in agarose gels and blotted onto nitrocellulose and/or nylon filters. These filters are probed with the cDNA encoding the receptor from black cutworm using low stringency conditions of hybridization and washing. Genes with a similarity to the black cutworm receptor to VIP3A(a) lower than 50% were identified. The Southern analysis can also be probed against partial sequences of the cDNA which encode specific domains such as death domain or EGF-like motifs with the intention of isolating genes that contain similar domains even though they are functionally different to the black cutworm receptor to VIP3A(a).

The isolation of homologues to the black cutworm receptor to VIP3A(a) is be accomplished by the two hybrid system described in Fields, S. and Song, O.-K. Nature 340:245–246 (1989). Isolated mRNA is obtained from an organisms of interest, synthesize cDNAs and clone them into pGAD10 or equivalent plasmids. The cDNA library is co-transformed with the pGB9-bearing the vip3A(a) gene (or homologues of this gene) and rescued putative receptors in yeast by means of activating a marker based upon protein-protein interaction between the VIP3A(a) protein (or homologues) and the putative receptor.

Homologues to the black cutworm receptor to VIP3A(a) are isolated by expressing cDNAs libraries isolated from organisms of interests, cloned into appropriate expression vectors and transformed into host cells such as yeast or insect cells which are known not to have the ability to bind and/or be sensitive to VIP3A(a). The transformed cells are screened based on their gained property of binding VIP3A (a) or undergoing apoptotic responses when incubated with VIP3A(a).In this case, the protein VIP3A(a) is used as probe and its binding will be monitored either by antibodies against VIP3A(a) or by labels such as biotin attached to VIP3A(a).

Example 13

Screening for Novel Compounds that Induce Apoptosis in Insect Cells

Model cell lines for different orders of insects (some examples include Sf-9 cells for lepidopteran, Colorado potato beetle for coleopterans, 82 from Drosophila for dipterans) is used to screen for novel compounds whose mode of action is induction of apoptosis. The cells are grown in multi-well plates which are used for a high-throughput assay screening for thousands of compounds (both of large and small molecular weight). The compound(s) are added as single component or as mixtures. Compound(s) Inducing apoptosis are identified as follows: 1) membrane protrusions are visible in the cell membrane, 2) a reorganization of the phosphatidylserine containing membrane lipids is detectable by using specific proteins with high affinity for phosphatidylserine such as Annexin-V linked to a visual marker, 3) cytoplasmic blabbing is visible in the cell cytoplasm, 4) active mitochondria can be visualized by using vital dyes such as rhodamine 123 that accumulate in mitochondria, 5) DNA fragmentation is detected either by DNA analysis in agarose gels, by ELISA detection of nucleosomal release or by in vivo detection of DNA nicking. All these cytological and molecular features are indicative of apoptosis.

The black cutworm receptor to VIP3A(a) is transformed into S2 cell line. Therefore, isogenic S2 lines are available with and without the said receptor. These cell lines are used to screen compounds that provide a differential response due to the presence of the said receptor. Transformed S2 cells undergoing apoptosis upon exposure to certain compounds are identified as indicated above. The differential response of the transformed versus the non-transformed cell is indicative that the action of the compound is mediated by the cloned receptor. Similar approaches are undertaken with insect cells transformed with receptors homologue to the black cutworm receptor to VIP3A(a).

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, It will be obvious that certain changes and modifications may be practiced within the scope of the appended claims.

What is claimed is:

1. A method of controlling a hemipteran insect, comprising contacting said hemipteran insect with a transgenic plant comprising a heterologous DNA sequence which encodes an insecticidal protein comprising an amino acid sequence that is the translation product of a nucleotide sequence whose complement hybridizes to SEQ ID NO:1, SEQ ID NO:3, or SEQ ID NO:5 under hybridization conditions of 68° C. followed by washing at 68° C. in 2×SSC containing 0.1% SDS.

2. A method according to claim 1, wherein said protein comprises an amino acid sequence selected from the group consisting of SEQ ID NO:2, SEQ ID NO:4, and SEQ ID NO:6.

3. A method according to claim 1, wherein said heterologous DNA sequence comprises a nucleic acid sequence whose complement hybridizes to a nucleic acid sequence selected from the group consisting of SEQ ID NO:1, SEQ ID NO:3, and SEQ ID NO:5 under hybridization conditions of 68° C. followed by washing at 68° C. in 2×SSC containing 0.1% SDS.

4. A method according to claim 1, wherein said hemipteran insect is a lygus bug.

5. A method of controlling a hemipteran insect comprising, contacting said hemipteran insect with a VIP protein encoded by a nucleotide sequence having a complement that hybridizes to a sequence selected from the group consisting of SEQ ID NO:1, SEQ ID NO:3, and SEQ ID NO:5, under hybridization conditions of 68° C. followed by washing at 68° C. in 2×SSC containing 0.1% SDS.

6. A method according to claim 5, wherein said protein comprises an amino acid sequence selected from the group consisting of SEQ ID NO:2, SEQ ID NO:4, and SEQ ID NO:6.

7. A method according to claim 5, wherein contacting said hemipteran insect with a VIP protein is carried out with a transgenic plant comprising said nucleotide sequence.

8. A method according to claim 5, wherein said hemipteran insect is a lygus bug.

* * * * *

SEQUENCE LISTING

```
<160> NUMBER OF SEQ ID NOS: 22

<210> SEQ ID NO 1
<211> LENGTH: 2378
<212> TYPE: DNA
<213> ORGANISM: Bacillus thuringiensis
<220> FEATURE:
<221> NAME/KEY: CDS
<222> LOCATION: (9)..(2375)
<223> OTHER INFORMATION: Native DNA sequence encoding VIP3A(a) protein
      from AB88 as contained in pCIB7104

<400> SEQUENCE: 1 agatgaac atg aac aag aat aat act aaa tta agc aca aga gcc tta cca        50
         Met Asn Lys Asn Asn Thr Lys Leu Ser Thr Arg Ala Leu Pro
           1               5                  10 agt ttt att gat tat ttt aat ggc att tat gga ttt gcc act ggt atc        98
Ser Phe Ile Asp Tyr Phe Asn Gly Ile Tyr Gly Phe Ala Thr Gly Ile
 15              20                  25                  30 aaa gac att atg aac atg att ttt aaa acg gat aca ggt ggt gat cta       146
Lys Asp Ile Met Asn Met Ile Phe Lys Thr Asp Thr Gly Gly Asp Leu
                 35                  40                  45 acc cta gac gaa att tta aag aat cag cag tta cta aat gat att tct       194
Thr Leu Asp Glu Ile Leu Lys Asn Gln Gln Leu Leu Asn Asp Ile Ser
             50                  55                  60 ggt aaa ttg gat ggg gtg aat gga agc tta aat gat ctt atc gca cag       242
Gly Lys Leu Asp Gly Val Asn Gly Ser Leu Asn Asp Leu Ile Ala Gln
         65                  70                  75 gga aac tta aat aca gaa tta tct aag gaa ata tta aaa att gca aat       290
Gly Asn Leu Asn Thr Glu Leu Ser Lys Glu Ile Leu Lys Ile Ala Asn
     80                  85                  90 gaa caa aat caa gtt tta aat gat gtt aat aac aaa ctc gat gcg ata       338
Glu Gln Asn Gln Val Leu Asn Asp Val Asn Asn Lys Leu Asp Ala Ile
 95                 100                 105                 110 aat acg atg ctt cgg gta tat cta cct aaa att acc tct atg ttg agt       386
```

```
                                                              -continued

Asn Thr Met Leu Arg Val Tyr Leu Pro Lys Ile Thr Ser Met Leu Ser
            115                 120                 125 gat gta atg aaa caa aat tat gcg cta agt ctg caa ata gaa tac tta       434
Asp Val Met Lys Gln Asn Tyr Ala Leu Ser Leu Gln Ile Glu Tyr Leu
        130                 135                 140 agt aaa caa ttg caa gag att tct gat aag ttg gat att att aat gta       482
Ser Lys Gln Leu Gln Glu Ile Ser Asp Lys Leu Asp Ile Ile Asn Val
            145                 150                 155 aat gta ctt att aac tct aca ctt act gaa att aca cct gcg tat caa       530
Asn Val Leu Ile Asn Ser Thr Leu Thr Glu Ile Thr Pro Ala Tyr Gln
160                 165                 170 agg att aaa tat gtg aac gaa aaa ttt gag gaa tta act ttt gct aca       578
Arg Ile Lys Tyr Val Asn Glu Lys Phe Glu Glu Leu Thr Phe Ala Thr
175                 180                 185                 190 gaa act agt tca aaa gta aaa aag gat ggc tct cct gca gat att ctt       626
Glu Thr Ser Ser Lys Val Lys Lys Asp Gly Ser Pro Ala Asp Ile Leu
                195                 200                 205 gat gag tta act gag tta act gaa cta gcg aaa agt gta aca aaa aat       674
Asp Glu Leu Thr Glu Leu Thr Glu Leu Ala Lys Ser Val Thr Lys Asn
            210                 215                 220 gat gtg gat ggt ttt gaa ttt tac ctt aat aca ttc cac gat gta atg       722
Asp Val Asp Gly Phe Glu Phe Tyr Leu Asn Thr Phe His Asp Val Met
        225                 230                 235 gta gga aat aat tta ttc ggg cgt tca gct tta aaa act gca tcg gaa       770
Val Gly Asn Asn Leu Phe Gly Arg Ser Ala Leu Lys Thr Ala Ser Glu
    240                 245                 250 tta att act aaa gaa aat gtg aaa aca agt ggc agt gag gtc gga aat       818
Leu Ile Thr Lys Glu Asn Val Lys Thr Ser Gly Ser Glu Val Gly Asn
255                 260                 265                 270 gtt tat aac ttc tta att gta tta aca gct ctg caa gcc caa gct ttt       866
Val Tyr Asn Phe Leu Ile Val Leu Thr Ala Leu Gln Ala Gln Ala Phe
                275                 280                 285 ctt act tta aca aca tgc cga aaa tta tta ggc tta gca gat att gat       914
Leu Thr Leu Thr Thr Cys Arg Lys Leu Leu Gly Leu Ala Asp Ile Asp
            290                 295                 300 tat act tct att atg aat gaa cat tta aat aag gaa aaa gag gaa ttt       962
Tyr Thr Ser Ile Met Asn Glu His Leu Asn Lys Glu Lys Glu Glu Phe
        305                 310                 315 aga gta aac atc ctc cct aca ctt tct aat act ttt tct aat cct aat      1010
Arg Val Asn Ile Leu Pro Thr Leu Ser Asn Thr Phe Ser Asn Pro Asn
    320                 325                 330 tat gca aaa gtt aaa gga agt gat gaa gat gca aag atg att gtg gaa      1058
Tyr Ala Lys Val Lys Gly Ser Asp Glu Asp Ala Lys Met Ile Val Glu
335                 340                 345                 350 gct aaa cca gga cat gca ttg att ggg ttt gaa att agt aat gat tca      1106
Ala Lys Pro Gly His Ala Leu Ile Gly Phe Glu Ile Ser Asn Asp Ser
                355                 360                 365 att aca gta tta aaa gta tat gag gct aag cta aaa caa aat tat caa      1154
Ile Thr Val Leu Lys Val Tyr Glu Ala Lys Leu Lys Gln Asn Tyr Gln
            370                 375                 380 gtc gat aag gat tcc tta tcg gaa gtt att tat ggt gat atg gat aaa      1202
Val Asp Lys Asp Ser Leu Ser Glu Val Ile Tyr Gly Asp Met Asp Lys
        385                 390                 395 tta ttg tgc cca gat caa tct gaa caa atc tat tat aca aat aac ata      1250
Leu Leu Cys Pro Asp Gln Ser Glu Gln Ile Tyr Tyr Thr Asn Asn Ile
    400                 405                 410 gta ttt cca aat gaa tat gta att act aaa att gat ttc act aaa aaa      1298
Val Phe Pro Asn Glu Tyr Val Ile Thr Lys Ile Asp Phe Thr Lys Lys
415                 420                 425                 430
```

```
atg aaa act tta aga tat gag gta aca gcg aat ttt tat gat tct tct    1346
Met Lys Thr Leu Arg Tyr Glu Val Thr Ala Asn Phe Tyr Asp Ser Ser
            435                 440                 445 aca gga gaa att gac tta aat aag aaa aaa gta gaa tca agt gaa gcg    1394
Thr Gly Glu Ile Asp Leu Asn Lys Lys Lys Val Glu Ser Ser Glu Ala
                450                 455                 460 gag tat aga acg tta agt gct aat gat gat ggg gtg tat atg ccg tta    1442
Glu Tyr Arg Thr Leu Ser Ala Asn Asp Asp Gly Val Tyr Met Pro Leu
            465                 470                 475 ggt gtc atc agt gaa aca ttt ttg act ccg att aat ggg ttt ggc ctc    1490
Gly Val Ile Ser Glu Thr Phe Leu Thr Pro Ile Asn Gly Phe Gly Leu
        480                 485                 490 caa gct gat gaa aat tca aga tta att act tta aca tgt aaa tca tat    1538
Gln Ala Asp Glu Asn Ser Arg Leu Ile Thr Leu Thr Cys Lys Ser Tyr
495                 500                 505                 510 tta aga gaa cta ctg cta gca aca gac tta agc aat aaa gaa act aaa    1586
Leu Arg Glu Leu Leu Leu Ala Thr Asp Leu Ser Asn Lys Glu Thr Lys
                515                 520                 525 ttg atc gtc ccg cca agt ggt ttt att agc aat att gta gag aac ggg    1634
Leu Ile Val Pro Pro Ser Gly Phe Ile Ser Asn Ile Val Glu Asn Gly
            530                 535                 540 tcc ata gaa gag gac aat tta gag ccg tgg aaa gca aat aat aag aat    1682
Ser Ile Glu Glu Asp Asn Leu Glu Pro Trp Lys Ala Asn Asn Lys Asn
        545                 550                 555 gcg tat gta gat cat aca ggc gga gtg aat gga act aaa gct tta tat    1730
Ala Tyr Val Asp His Thr Gly Gly Val Asn Gly Thr Lys Ala Leu Tyr
    560                 565                 570 gtt cat aag gac gga gga att tca caa ttt att gga gat aag tta aaa    1778
Val His Lys Asp Gly Gly Ile Ser Gln Phe Ile Gly Asp Lys Leu Lys
575                 580                 585                 590 ccg aaa act gag tat gta atc caa tat act gtt aaa gga aaa cct tct    1826
Pro Lys Thr Glu Tyr Val Ile Gln Tyr Thr Val Lys Gly Lys Pro Ser
                595                 600                 605 att cat tta aaa gat gaa aat act gga tat att cat tat gaa gat aca    1874
Ile His Leu Lys Asp Glu Asn Thr Gly Tyr Ile His Tyr Glu Asp Thr
            610                 615                 620 aat aat aat tta gaa gat tat caa act att aat aaa cgt ttt act aca    1922
Asn Asn Asn Leu Glu Asp Tyr Gln Thr Ile Asn Lys Arg Phe Thr Thr
        625                 630                 635 gga act gat tta aag gga gtg tat tta att tta aaa agt caa aat gga    1970
Gly Thr Asp Leu Lys Gly Val Tyr Leu Ile Leu Lys Ser Gln Asn Gly
    640                 645                 650 gat gaa gct tgg gga gat aac ttt att att ttg gaa att agt cct tct    2018
Asp Glu Ala Trp Gly Asp Asn Phe Ile Ile Leu Glu Ile Ser Pro Ser
655                 660                 665                 670 gaa aag tta tta agt cca gaa tta att aat aca aat aat tgg acg agt    2066
Glu Lys Leu Leu Ser Pro Glu Leu Ile Asn Thr Asn Asn Trp Thr Ser
                675                 680                 685 acg gga tca act aat att agc ggt aat aca ctc act ctt tat cag gga    2114
Thr Gly Ser Thr Asn Ile Ser Gly Asn Thr Leu Thr Leu Tyr Gln Gly
            690                 695                 700 gga cga ggg att cta aaa caa aac ctt caa tta gat agt ttt tca act    2162
Gly Arg Gly Ile Leu Lys Gln Asn Leu Gln Leu Asp Ser Phe Ser Thr
        705                 710                 715 tat aga gtg tat ttt tct gtg tcc gga gat gct aat gta agg att aga    2210
Tyr Arg Val Tyr Phe Ser Val Ser Gly Asp Ala Asn Val Arg Ile Arg
    720                 725                 730 aat tct agg gaa gtg tta ttt gaa aaa aga tat atg agc ggt gct aaa    2258
Asn Ser Arg Glu Val Leu Phe Glu Lys Arg Tyr Met Ser Gly Ala Lys
735                 740                 745                 750
```

-continued

```
gat gtt tct gaa atg ttc act aca aaa ttt gag aaa gat aac ttt tat    2306
Asp Val Ser Glu Met Phe Thr Thr Lys Phe Glu Lys Asp Asn Phe Tyr
            755                 760                 765 ata gag ctt tct caa ggg aat aat tta tat ggt ggt cct att gta cat    2354
Ile Glu Leu Ser Gln Gly Asn Asn Leu Tyr Gly Gly Pro Ile Val His
        770                 775                 780 ttt tac gat gtc tct att aag taa                                    2378
Phe Tyr Asp Val Ser Ile Lys
    785
```

<210> SEQ ID NO 2
<211> LENGTH: 789
<212> TYPE: PRT
<213> ORGANISM: Bacillus thuringiensis

<400> SEQUENCE: 2

```
Met Asn Lys Asn Asn Thr Lys Leu Ser Thr Arg Ala Leu Pro Ser Phe
 1               5                  10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asp Leu Thr Leu
        35                  40                  45

Asp Glu Ile Leu Lys Asn Gln Gln Leu Leu Asn Asp Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu Arg Val Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Lys
    130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Ser Ser Lys Val Lys Lys Asp Gly Ser Pro Ala Asp Ile Leu Asp Glu
        195                 200                 205

Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Thr Lys Glu Asn Val Lys Thr Ser Gly Ser Glu Val Gly Asn Val Tyr
            260                 265                 270

Asn Phe Leu Ile Val Leu Thr Ala Leu Gln Ala Gln Ala Phe Leu Thr
        275                 280                 285

Leu Thr Thr Cys Arg Lys Leu Leu Gly Leu Ala Asp Ile Asp Tyr Thr
    290                 295                 300

Ser Ile Met Asn Glu His Leu Asn Lys Glu Lys Glu Glu Phe Arg Val
```

-continued

```
305                 310                 315                 320
Asn Ile Leu Pro Thr Leu Ser Asn Thr Phe Ser Asn Pro Asn Tyr Ala
                325                 330                 335
Lys Val Lys Gly Ser Asp Glu Asp Ala Lys Met Ile Val Glu Ala Lys
                340                 345                 350
Pro Gly His Ala Leu Ile Gly Phe Glu Ile Ser Asn Asp Ser Ile Thr
                355                 360                 365
Val Leu Lys Val Tyr Glu Ala Lys Leu Lys Gln Asn Tyr Gln Val Asp
            370                 375                 380
Lys Asp Ser Leu Ser Glu Val Ile Tyr Gly Asp Met Asp Lys Leu Leu
385                 390                 395                 400
Cys Pro Asp Gln Ser Glu Gln Ile Tyr Tyr Thr Asn Asn Ile Val Phe
                405                 410                 415
Pro Asn Glu Tyr Val Ile Thr Lys Ile Asp Phe Thr Lys Lys Met Lys
                420                 425                 430
Thr Leu Arg Tyr Glu Val Thr Ala Asn Phe Tyr Asp Ser Ser Thr Gly
            435                 440                 445
Glu Ile Asp Leu Asn Lys Lys Val Glu Ser Glu Ala Glu Tyr
            450                 455                 460
Arg Thr Leu Ser Ala Asn Asp Asp Gly Val Tyr Met Pro Leu Gly Val
465                 470                 475                 480
Ile Ser Glu Thr Phe Leu Thr Pro Ile Asn Gly Phe Gly Leu Gln Ala
                485                 490                 495
Asp Glu Asn Ser Arg Leu Ile Thr Leu Thr Cys Lys Ser Tyr Leu Arg
                500                 505                 510
Glu Leu Leu Leu Ala Thr Asp Leu Ser Asn Lys Glu Thr Lys Leu Ile
            515                 520                 525
Val Pro Pro Ser Gly Phe Ile Ser Asn Ile Val Glu Asn Gly Ser Ile
            530                 535                 540
Glu Glu Asp Asn Leu Glu Pro Trp Lys Ala Asn Asn Lys Asn Ala Tyr
545                 550                 555                 560
Val Asp His Thr Gly Gly Val Asn Gly Thr Lys Ala Leu Tyr Val His
                565                 570                 575
Lys Asp Gly Gly Ile Ser Gln Phe Ile Gly Asp Lys Leu Lys Pro Lys
                580                 585                 590
Thr Glu Tyr Val Ile Gln Tyr Thr Val Lys Gly Lys Pro Ser Ile His
            595                 600                 605
Leu Lys Asp Glu Asn Thr Gly Tyr Ile His Tyr Glu Asp Thr Asn Asn
            610                 615                 620
Asn Leu Glu Asp Tyr Gln Thr Ile Asn Lys Arg Phe Thr Thr Gly Thr
625                 630                 635                 640
Asp Leu Lys Gly Val Tyr Leu Ile Leu Lys Ser Gln Asn Gly Asp Glu
                645                 650                 655
Ala Trp Gly Asp Asn Phe Ile Ile Leu Glu Ile Ser Pro Ser Glu Lys
                660                 665                 670
Leu Leu Ser Pro Glu Leu Ile Asn Thr Asn Asn Trp Thr Ser Thr Gly
            675                 680                 685
Ser Thr Asn Ile Ser Gly Asn Thr Leu Thr Leu Tyr Gln Gly Gly Arg
            690                 695                 700
Gly Ile Leu Lys Gln Asn Leu Gln Leu Asp Ser Phe Ser Thr Tyr Arg
705                 710                 715                 720
Val Tyr Phe Ser Val Ser Gly Asp Ala Asn Val Arg Ile Arg Asn Ser
                725                 730                 735
```

```
Arg Glu Val Leu Phe Glu Lys Arg Tyr Met Ser Gly Ala Lys Asp Val
            740                 745                 750
Ser Glu Met Phe Thr Thr Lys Phe Glu Lys Asp Asn Phe Tyr Ile Glu
        755                 760                 765
Leu Ser Gln Gly Asn Asn Leu Tyr Gly Gly Pro Ile Val His Phe Tyr
    770                 775                 780
Asp Val Ser Ile Lys
785

<210> SEQ ID NO 3
<211> LENGTH: 2612
<212> TYPE: DNA
<213> ORGANISM: Bacillus thuringiensis
<220> FEATURE:
<221> NAME/KEY: CDS
<222> LOCATION: (118)..(2484)
<223> OTHER INFORMATION: Native DNA sequence encoding VIP3A(b) from
      AB424

<400> SEQUENCE: 3
attgaaattg ataaaaagtt atgagtgttt aataatcagt aattaccaat aaagaattaa      60
gaatacaagt ttacaagaaa taagtgttac aaaaaatagc tgaaaaggaa gatgaac        117 atg aac aag aat aat act aaa tta agc aca aga gcc tta cca agt ttt       165
Met Asn Lys Asn Asn Thr Lys Leu Ser Thr Arg Ala Leu Pro Ser Phe
 1               5                   10                  15 att gat tat ttc aat ggc att tat gga ttt gcc act ggt atc aaa gac       213
Ile Asp Tyr Phe Asn Gly Ile Tyr Gly Phe Ala Thr Gly Ile Lys Asp
                20                  25                  30 att atg aac atg att ttt aaa acg gat aca ggt ggt gat cta acc cta       261
Ile Met Asn Met Ile Phe Lys Thr Asp Thr Gly Gly Asp Leu Thr Leu
            35                  40                  45 gac gaa att tta aag aat cag cag cta cta aat gat att tct ggt aaa       309
Asp Glu Ile Leu Lys Asn Gln Gln Leu Leu Asn Asp Ile Ser Gly Lys
        50                  55                  60 ttg gat ggg gtg aat gga agc tta aat gat ctt atc gca cag gga aac       357
Leu Asp Gly Val Asn Gly Ser Leu Asn Asp Leu Ile Ala Gln Gly Asn
 65                  70                  75                  80 tta aat aca gaa tta tct aag gaa ata tta aaa att gca aat gaa caa       405
Leu Asn Thr Glu Leu Ser Lys Glu Ile Leu Lys Ile Ala Asn Glu Gln
                 85                  90                  95 aat caa gtt tta aat gat gtt aat aac aaa ctc gat gcg ata aat acg       453
Asn Gln Val Leu Asn Asp Val Asn Asn Lys Leu Asp Ala Ile Asn Thr
                100                 105                 110 atg ctt cgg gta tat cta cct aaa att acc tct atg ttg agt gat gta       501
Met Leu Arg Val Tyr Leu Pro Lys Ile Thr Ser Met Leu Ser Asp Val
            115                 120                 125 atg aaa caa aat tat gcg cta agt ctg caa ata gaa tac tta agt aaa       549
Met Lys Gln Asn Tyr Ala Leu Ser Leu Gln Ile Glu Tyr Leu Ser Lys
        130                 135                 140 caa ttg caa gag att tct gat aag ttg gat att att aat gta aat gta       597
Gln Leu Gln Glu Ile Ser Asp Lys Leu Asp Ile Ile Asn Val Asn Val
145                 150                 155                 160 ctt att aac tct aca ctt act gaa att aca cct gcg tat caa agg att       645
Leu Ile Asn Ser Thr Leu Thr Glu Ile Thr Pro Ala Tyr Gln Arg Ile
                165                 170                 175 aaa tat gtg aac gaa aaa ttt gag gaa tta act ttt gct aca gaa act       693
Lys Tyr Val Asn Glu Lys Phe Glu Glu Leu Thr Phe Ala Thr Glu Thr
                180                 185                 190 agt tca aaa gta aaa aag gat ggc tct cct gca gat att cgt gat gag       741
```

```
                                              -continued

Ser Ser Lys Val Lys Asp Gly Ser Pro Ala Asp Ile Arg Asp Glu
        195                 200                 205 tta act gag tta act gaa cta gcg aaa agt gta aca aaa aat gat gtg     789
Leu Thr Glu Leu Thr Glu Leu Ala Lys Ser Val Thr Lys Asn Asp Val
    210                 215                 220 gat ggt ttt gaa ttt tac ctt aat aca ttc cac gat gta atg gta gga     837
Asp Gly Phe Glu Phe Tyr Leu Asn Thr Phe His Asp Val Met Val Gly
225                 230                 235                 240 aat aat tta ttc ggg cgt tca gct tta aaa act gca tcg gaa tta att     885
Asn Asn Leu Phe Gly Arg Ser Ala Leu Lys Thr Ala Ser Glu Leu Ile
                245                 250                 255 act aaa gaa aat gtg aaa aca agt ggc agt gag gtc gga aat gtt tat     933
Thr Lys Glu Asn Val Lys Thr Ser Gly Ser Glu Val Gly Asn Val Tyr
            260                 265                 270 aac ttc cta att gta tta aca gct ctg caa gca aaa gct ttt ctt act     981
Asn Phe Leu Ile Val Leu Thr Ala Leu Gln Ala Lys Ala Phe Leu Thr
        275                 280                 285 tta aca cca tgc cga aaa tta tta ggc tta gca gat att gat tat act    1029
Leu Thr Pro Cys Arg Lys Leu Leu Gly Leu Ala Asp Ile Asp Tyr Thr
    290                 295                 300 tct att atg aat gaa cat tta aat aag gaa aaa gag gaa ttt aga gta    1077
Ser Ile Met Asn Glu His Leu Asn Lys Glu Lys Glu Glu Phe Arg Val
305                 310                 315                 320 aac atc ctc cct aca ctt tct aat act ttt tct aat cct aat tat gca    1125
Asn Ile Leu Pro Thr Leu Ser Asn Thr Phe Ser Asn Pro Asn Tyr Ala
                325                 330                 335 aaa gtt aaa gga agt gat gaa gat gca aag atg att gtg gaa gct aaa    1173
Lys Val Lys Gly Ser Asp Glu Asp Ala Lys Met Ile Val Glu Ala Lys
            340                 345                 350 cca gga cat gca ttg att ggg ttt gaa att agt aat gat tca att aca    1221
Pro Gly His Ala Leu Ile Gly Phe Glu Ile Ser Asn Asp Ser Ile Thr
        355                 360                 365 gta tta aaa gta tat gag gct aag cta aaa caa aat tat caa gtc gat    1269
Val Leu Lys Val Tyr Glu Ala Lys Leu Lys Gln Asn Tyr Gln Val Asp
    370                 375                 380 aag gat tcc tta tcg gaa gtt att tat ggc gat atg gat aaa tta ttg    1317
Lys Asp Ser Leu Ser Glu Val Ile Tyr Gly Asp Met Asp Lys Leu Leu
385                 390                 395                 400 tgc cca gat caa tct gga caa atc tat tat aca aat aac ata gta ttt    1365
Cys Pro Asp Gln Ser Gly Gln Ile Tyr Tyr Thr Asn Asn Ile Val Phe
                405                 410                 415 cca aat gaa tat gta att act aaa att gat ttc act aaa aaa atg aaa    1413
Pro Asn Glu Tyr Val Ile Thr Lys Ile Asp Phe Thr Lys Lys Met Lys
            420                 425                 430 act tta aga tat gag gta aca gcg aat ttt tat gat tct tct aca gga    1461
Thr Leu Arg Tyr Glu Val Thr Ala Asn Phe Tyr Asp Ser Ser Thr Gly
        435                 440                 445 gaa att gac tta aat aag aaa aaa gta gaa tca agt gaa gcg gag tat    1509
Glu Ile Asp Leu Asn Lys Lys Lys Val Glu Ser Ser Glu Ala Glu Tyr
    450                 455                 460 aga acg tta agt gct aat gat gat ggg gtg tat atg ccg tta ggt gtc    1557
Arg Thr Leu Ser Ala Asn Asp Asp Gly Val Tyr Met Pro Leu Gly Val
465                 470                 475                 480 atc agt gaa aca ttt ttg act ccg att aat ggg ttt ggc ctc caa gct    1605
Ile Ser Glu Thr Phe Leu Thr Pro Ile Asn Gly Phe Gly Leu Gln Ala
                485                 490                 495 gat gaa aat tca aga tta att act tta aca tgt aaa tca tat tta aga    1653
Asp Glu Asn Ser Arg Leu Ile Thr Leu Thr Cys Lys Ser Tyr Leu Arg
            500                 505                 510
```

```
gaa cta ctg cta gca aca gac tta agc aat aaa gaa act aaa ttg atc    1701
Glu Leu Leu Leu Ala Thr Asp Leu Ser Asn Lys Glu Thr Lys Leu Ile
        515                 520                 525 gtc ccg cca agt ggt ttt att agc aat att gta gag aac ggg tcc ata    1749
Val Pro Pro Ser Gly Phe Ile Ser Asn Ile Val Glu Asn Gly Ser Ile
530                 535                 540 gaa gag gac aat tta gag ccg tgg aaa gca aat aat aag aat gcg tat    1797
Glu Glu Asp Asn Leu Glu Pro Trp Lys Ala Asn Asn Lys Asn Ala Tyr
545                 550                 555                 560 gta gat cat aca ggc gga gtg aat gga act aaa gct tta tat gtt cat    1845
Val Asp His Thr Gly Gly Val Asn Gly Thr Lys Ala Leu Tyr Val His
            565                 570                 575 aag gac gga gga att tca caa ttt att gga gat aag tta aaa ccg aaa    1893
Lys Asp Gly Gly Ile Ser Gln Phe Ile Gly Asp Lys Leu Lys Pro Lys
        580                 585                 590 act gag tat gta atc caa tat act gtt aaa gga aaa cct tct att cat    1941
Thr Glu Tyr Val Ile Gln Tyr Thr Val Lys Gly Lys Pro Ser Ile His
    595                 600                 605 tta aaa gat gaa aat act gga tat att cat tat gaa gat aca aat aat    1989
Leu Lys Asp Glu Asn Thr Gly Tyr Ile His Tyr Glu Asp Thr Asn Asn
610                 615                 620 aat tta gaa gat tat caa act att aat aaa cgt ttt act aca gga act    2037
Asn Leu Glu Asp Tyr Gln Thr Ile Asn Lys Arg Phe Thr Thr Gly Thr
625                 630                 635                 640 gat tta aag gga gtg tat tta att tta aaa agt caa aat gga gat gaa    2085
Asp Leu Lys Gly Val Tyr Leu Ile Leu Lys Ser Gln Asn Gly Asp Glu
            645                 650                 655 gct tgg gga gat aac ttt att att ttg gaa att agt cct tct gaa aag    2133
Ala Trp Gly Asp Asn Phe Ile Ile Leu Glu Ile Ser Pro Ser Glu Lys
        660                 665                 670 tta tta agt cca gaa tta att aat aca aat aat tgg acg agt acg gga    2181
Leu Leu Ser Pro Glu Leu Ile Asn Thr Asn Asn Trp Thr Ser Thr Gly
    675                 680                 685 tca act aat att agc ggt aat aca ctc act ctt tat cag gga gga cga    2229
Ser Thr Asn Ile Ser Gly Asn Thr Leu Thr Leu Tyr Gln Gly Gly Arg
690                 695                 700 ggg att cta aaa caa aac ctt caa tta gat agt ttt tca act tat aga    2277
Gly Ile Leu Lys Gln Asn Leu Gln Leu Asp Ser Phe Ser Thr Tyr Arg
705                 710                 715                 720 gtg tat ttc tct gtg tcc gga gat gct aat gta agg att aga aat tct    2325
Val Tyr Phe Ser Val Ser Gly Asp Ala Asn Val Arg Ile Arg Asn Ser
            725                 730                 735 agg gaa gtg tta ttt gaa aaa aga tat atg agc ggt gct aaa gat gtt    2373
Arg Glu Val Leu Phe Glu Lys Arg Tyr Met Ser Gly Ala Lys Asp Val
        740                 745                 750 tct gaa atg ttc act aca aaa ttt gag aaa gat aac ttc tat ata gag    2421
Ser Glu Met Phe Thr Thr Lys Phe Glu Lys Asp Asn Phe Tyr Ile Glu
    755                 760                 765 ctt tct caa ggg aat aat tta tat ggt ggt cct att gta cat ttt tac    2469
Leu Ser Gln Gly Asn Asn Leu Tyr Gly Gly Pro Ile Val His Phe Tyr
770                 775                 780 gat gtc tct att aag taagatcggg atctaatatt aacagttttt agaagctaat    2524
Asp Val Ser Ile Lys
785 tcttgtataa tgtccttgat tatggaaaaa cacaattttg tttgctaaga tgtatatata    2584 gctcactcat taaaaggcaa tcaagctt                                        2612

<210> SEQ ID NO 4
<211> LENGTH: 789
```

```
<212> TYPE: PRT
<213> ORGANISM: Bacillus thuringiensis

<400> SEQUENCE: 4

Met Asn Lys Asn Asn Thr Lys Leu Ser Thr Arg Ala Leu Pro Ser Phe
 1               5                  10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asp Leu Thr Leu
        35                  40                  45

Asp Glu Ile Leu Lys Asn Gln Gln Leu Leu Asn Asp Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu Arg Val Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Lys
    130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Ser Ser Lys Val Lys Lys Asp Gly Ser Pro Ala Asp Ile Arg Asp Glu
        195                 200                 205

Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Thr Lys Glu Asn Val Lys Thr Ser Gly Ser Glu Val Gly Asn Val Tyr
            260                 265                 270

Asn Phe Leu Ile Val Leu Thr Ala Leu Gln Ala Lys Ala Phe Leu Thr
        275                 280                 285

Leu Thr Pro Cys Arg Lys Leu Leu Gly Leu Ala Asp Ile Asp Tyr Thr
    290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
            340                 345                 350

Pro Gly His Ala Leu Ile Gly Phe Glu Ile Ser Asn Asp Ser Ile Thr
        355                 360                 365

Val Leu Lys Val Tyr Glu Ala Lys Leu Lys Gln Asn Tyr Gln Val Asp
    370                 375                 380

Lys Asp Ser Leu Ser Glu Val Ile Tyr Gly Asp Met Asp Lys Leu Leu
385                 390                 395                 400
```

```
Cys Pro Asp Gln Ser Gly Gln Ile Tyr Tyr Thr Asn Asn Ile Val Phe
            405                 410                 415

Pro Asn Glu Tyr Val Ile Thr Lys Ile Asp Phe Thr Lys Lys Met Lys
            420                 425                 430

Thr Leu Arg Tyr Glu Val Thr Ala Asn Phe Tyr Asp Ser Ser Thr Gly
            435                 440                 445

Glu Ile Asp Leu Asn Lys Lys Lys Val Glu Ser Ser Glu Ala Glu Tyr
            450                 455                 460

Arg Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
            485                 490                 495

Asp Glu Asn Ser Arg Leu Ile Thr Leu Thr Cys Lys Ser Tyr Leu Arg
            500                 505                 510

Glu Leu Leu Ala Thr Asp Leu Ser Asn Lys Glu Thr Lys Leu Ile
            515                 520                 525

Val Pro Pro Ser Gly Phe Ile Ser Asn Ile Val Glu Asn Gly Ser Ile
            530                 535                 540

Glu Glu Asp Asn Leu Glu Pro Trp Lys Ala Asn Asn Lys Asn Ala Tyr
545                 550                 555                 560

Val Asp His Thr Gly Gly Val Asn Gly Thr Lys Ala Leu Tyr Val His
            565                 570                 575

Lys Asp Gly Gly Ile Ser Gln Phe Ile Gly Asp Lys Leu Lys Pro Lys
            580                 585                 590

Thr Glu Tyr Val Ile Gln Tyr Thr Val Lys Gly Lys Pro Ser Ile His
            595                 600                 605

Leu Lys Asp Glu Asn Thr Gly Tyr Ile His Tyr Glu Asp Thr Asn Asn
            610                 615                 620

Asn Leu Glu Asp Tyr Gln Thr Ile Asn Lys Arg Phe Thr Thr Gly Thr
625                 630                 635                 640

Asp Leu Lys Gly Val Tyr Leu Ile Leu Lys Ser Gln Asn Gly Asp Glu
            645                 650                 655

Ala Trp Gly Asp Asn Phe Ile Ile Leu Glu Ile Ser Pro Ser Glu Lys
            660                 665                 670

Leu Leu Ser Pro Glu Leu Ile Asn Thr Asn Asn Trp Thr Ser Thr Gly
            675                 680                 685

Ser Thr Asn Ile Ser Gly Asn Thr Leu Thr Leu Tyr Gln Gly Gly Arg
            690                 695                 700

Gly Ile Leu Lys Gln Asn Leu Gln Leu Asp Ser Phe Ser Thr Tyr Arg
705                 710                 715                 720

Val Tyr Phe Ser Val Ser Gly Asp Ala Asn Val Arg Ile Arg Asn Ser
            725                 730                 735

Arg Glu Val Leu Phe Glu Lys Arg Tyr Met Ser Gly Ala Lys Asp Val
            740                 745                 750

Ser Glu Met Phe Thr Thr Lys Phe Glu Lys Asp Asn Phe Tyr Ile Glu
            755                 760                 765

Leu Ser Gln Gly Asn Asn Leu Tyr Gly Gly Pro Ile Val His Phe Tyr
            770                 775                 780

Asp Val Ser Ile Lys
785

<210> SEQ ID NO 5
<211> LENGTH: 2364
```

-continued

```
<212> TYPE: DNA
<213> ORGANISM: Bacillus thuringiensis
<220> FEATURE:
<221> NAME/KEY: CDS
<222> LOCATION: (56)..(2293)
<223> OTHER INFORMATION: Native DNA sequence encoding VIP3A(c) from AB51

<400> SEQUENCE: 5
aatacaattt acgagggata agtgttacaa agaatagctg aggagggaga tgaac atg      58
                                                             Met
                                                               1 aac aag aat aat gct aaa tta agc aca aga gcc tta cca agt ttt att      106
Asn Lys Asn Asn Ala Lys Leu Ser Thr Arg Ala Leu Pro Ser Phe Ile
            5                  10                  15 gat tat ttc aat ggc att tat gga ttt gcc act ggt atc aaa gac att      154
Asp Tyr Phe Asn Gly Ile Tyr Gly Phe Ala Thr Gly Ile Lys Asp Ile
        20                  25                  30 atg aac atg att ttt aaa acg gat aca ggt ggt gat cta gcc cta gac      202
Met Asn Met Ile Phe Lys Thr Asp Thr Gly Gly Asp Leu Ala Leu Asp
    35                  40                  45 gaa att tta gag aat cag cag cta cta aat gat att tct ggt aaa ttg      250
Glu Ile Leu Glu Asn Gln Gln Leu Leu Asn Asp Ile Ser Gly Lys Leu
 50                  55                  60                  65 gat ggg gtg aat gga agc tta aat gat ctt atc gca cag gga aac tta      298
Asp Gly Val Asn Gly Ser Leu Asn Asp Leu Ile Ala Gln Gly Asn Leu
                 70                  75                  80 aat aca gaa tta tct aag gaa ata tta aaa att gca aat gaa caa aat      346
Asn Thr Glu Leu Ser Lys Glu Ile Leu Lys Ile Ala Asn Glu Gln Asn
            85                  90                  95 caa gtt tta aat gat gtt aat aac aaa ctc gat gcg ata aat acg atg      394
Gln Val Leu Asn Asp Val Asn Asn Lys Leu Asp Ala Ile Asn Thr Met
        100                 105                 110 ctt cgg gta tat cta cct aaa att acc tct atg ttg agt gat gta atg      442
Leu Arg Val Tyr Leu Pro Lys Ile Thr Ser Met Leu Ser Asp Val Met
    115                 120                 125 aaa caa aat tat gcg cta agt ctg caa ata gaa tac tta agt aaa caa      490
Lys Gln Asn Tyr Ala Leu Ser Leu Gln Ile Glu Tyr Leu Ser Lys Gln
130                 135                 140                 145 ttg caa gag att tct gat aag ttg gat att att aat gta aat gta ctt      538
Leu Gln Glu Ile Ser Asp Lys Leu Asp Ile Ile Asn Val Asn Val Leu
                150                 155                 160 att aac tct aca ctt act gaa att aca cct gcg tat caa agg att aaa      586
Ile Asn Ser Thr Leu Thr Glu Ile Thr Pro Ala Tyr Gln Arg Ile Lys
            165                 170                 175 tat gtg aac gaa aaa ttt gag gaa tta act ttt gct aca gaa act agt      634
Tyr Val Asn Glu Lys Phe Glu Glu Leu Thr Phe Ala Thr Glu Thr Ser
        180                 185                 190 tca aaa gta aaa aag gat ggc tct cct gca gat att cgt gat gag tta      682
Ser Lys Val Lys Lys Asp Gly Ser Pro Ala Asp Ile Arg Asp Glu Leu
    195                 200                 205 agt gag tta act gaa cta gcg aaa agt gta aca caa aat gat gtg gat      730
Ser Glu Leu Thr Glu Leu Ala Lys Ser Val Thr Gln Asn Asp Val Asp
210                 215                 220                 225 ggt ttt gaa ttt tac ctt aat aca ttc cac gat gta atg gta gga aat      778
Gly Phe Glu Phe Tyr Leu Asn Thr Phe His Asp Val Met Val Gly Asn
                230                 235                 240 aat tta ttc ggg cgt tca gct tta aaa act gca tcg gaa tta att act      826
Asn Leu Phe Gly Arg Ser Ala Leu Lys Thr Ala Ser Glu Leu Ile Thr
            245                 250                 255 aaa gaa aat gtg aaa aca agt ggc agt gag gtc gga aat gtt tat aac      874
Lys Glu Asn Val Lys Thr Ser Gly Ser Glu Val Gly Asn Val Tyr Asn
```

|  |  |
|---|---|
| ttc cta att gta tta aca gct ctg caa gca caa gct ttt ctt act tta<br>Phe Leu Ile Val Leu Thr Ala Leu Gln Ala Gln Ala Phe Leu Thr Leu<br>275                       280                   285 | 922 |
| aca cca tgc cga aaa tta tta ggc tta gca gat att gat tat act tct<br>Thr Pro Cys Arg Lys Leu Leu Gly Leu Ala Asp Ile Asp Tyr Thr Ser<br>290               295                   300                 305 | 970 |
| att atg aat gaa cat tta aat aag gaa aaa gag gaa ttt aga gta aac<br>Ile Met Asn Glu His Leu Asn Lys Glu Lys Glu Glu Phe Arg Val Asn<br>                  310                   315                320 | 1018 |
| atc ctc cct aca ctt tct aat act ttt tct aat cct aat tat gca aaa<br>Ile Leu Pro Thr Leu Ser Asn Thr Phe Ser Asn Pro Asn Tyr Ala Lys<br>              325                   330                335 | 1066 |
| gtt aaa gga agt gat gaa gat gca aag atg att gtg gaa gct aaa cca<br>Val Lys Gly Ser Asp Glu Asp Ala Lys Met Ile Val Glu Ala Lys Pro<br>340                       345                   350 | 1114 |
| gga cat gca ttg att ggg ttt gaa att agt aat gat tca att aca gta<br>Gly His Ala Leu Ile Gly Phe Glu Ile Ser Asn Asp Ser Ile Thr Val<br>      355                   360                   365 | 1162 |
| tta aaa gta tat gag gct aag cta aaa caa aat tat caa gtc gat aag<br>Leu Lys Val Tyr Glu Ala Lys Leu Lys Gln Asn Tyr Gln Val Asp Lys<br>370                       375                   380                385 | 1210 |
| gat tcc tta tcg gaa gtt att tat ggc gat atg gat aaa tta ttg tgc<br>Asp Ser Leu Ser Glu Val Ile Tyr Gly Asp Met Asp Lys Leu Leu Cys<br>                  390                   395                400 | 1258 |
| cca gat caa tct gga caa atc tat tat aca aat aac ata gta ttt cca<br>Pro Asp Gln Ser Gly Gln Ile Tyr Tyr Thr Asn Asn Ile Val Phe Pro<br>              405                   410                415 | 1306 |
| aat gaa tat gta att act aaa att gat ttc act aaa aaa atg aaa act<br>Asn Glu Tyr Val Ile Thr Lys Ile Asp Phe Thr Lys Lys Met Lys Thr<br>      420                   425                   430 | 1354 |
| tta aga tat gag gta aca gcg aat ttt tat gat tct tct aca gga gaa<br>Leu Arg Tyr Glu Val Thr Ala Asn Phe Tyr Asp Ser Ser Thr Gly Glu<br>435                       440                   445 | 1402 |
| att gac tta aat aag aaa aaa gta gaa tca agt gaa gcg gag tat aga<br>Ile Asp Leu Asn Lys Lys Lys Val Glu Ser Ser Glu Ala Glu Tyr Arg<br>450                       455                   460                465 | 1450 |
| acg tta agt gct aat gat gat ggg gtg tat atg ccg tta ggt gtc atc<br>Thr Leu Ser Ala Asn Asp Asp Gly Val Tyr Met Pro Leu Gly Val Ile<br>                  470                   475                480 | 1498 |
| agt gaa aca ttt ttg act ccg att aat ggg ttt ggc ctc caa gct gat<br>Ser Glu Thr Phe Leu Thr Pro Ile Asn Gly Phe Gly Leu Gln Ala Asp<br>              485                   490                495 | 1546 |
| gaa aat tca aga tta att act tta aca tgt aaa tca tat tta aga gaa<br>Glu Asn Ser Arg Leu Ile Thr Leu Thr Cys Lys Ser Tyr Leu Arg Glu<br>500                       505                   510 | 1594 |
| cta ctg cta gca aca gac tta agc aat aaa gaa act aaa ttg atc gtc<br>Leu Leu Leu Ala Thr Asp Leu Ser Asn Lys Glu Thr Lys Leu Ile Val<br>      515                   520                   525 | 1642 |
| ccg cca agt ggt ttt att agc aat att gta gag aac ggg tcc ata gaa<br>Pro Pro Ser Gly Phe Ile Ser Asn Ile Val Glu Asn Gly Ser Ile Glu<br>530                       535                   540                545 | 1690 |
| gag gac aat tta gag ccg tgg aaa gca aat aat aag aat gcg tat gta<br>Glu Asp Asn Leu Glu Pro Trp Lys Ala Asn Asn Lys Asn Ala Tyr Val<br>                  550                   555                560 | 1738 |
| gat cat aca ggc gga gtg aat gga act aaa gct tta tat gtt cat aag<br>Asp His Thr Gly Gly Val Asn Gly Thr Lys Ala Leu Tyr Val His Lys<br>              565                   570                575 | 1786 |
| gac gga gga att tca caa ttt att gga gat aag tta aaa ccg aaa act | 1834 |

```
Asp Gly Gly Ile Ser Gln Phe Ile Gly Asp Lys Leu Lys Pro Lys Thr
            580                 585                 590 gag tat gta atc caa tat act gtt aaa gga aaa cct tct att cat tta    1882
Glu Tyr Val Ile Gln Tyr Thr Val Lys Gly Lys Pro Ser Ile His Leu
595                 600                 605 aaa gat gaa aat act gga tat att cat tat gaa gat aca aat aat aat    1930
Lys Asp Glu Asn Thr Gly Tyr Ile His Tyr Glu Asp Thr Asn Asn Asn
610                 615                 620                 625 tta gaa gat tat caa act att aat aaa cgt ttt act aca gga act gat    1978
Leu Glu Asp Tyr Gln Thr Ile Asn Lys Arg Phe Thr Thr Gly Thr Asp
                630                 635                 640 tta aag gga gtg tat tta att tta aaa agt caa aat gga gat gaa gct    2026
Leu Lys Gly Val Tyr Leu Ile Leu Lys Ser Gln Asn Gly Asp Glu Ala
            645                 650                 655 tgg gga gat aac ttt att att ttg gaa att agt cct tct gaa aag tta    2074
Trp Gly Asp Asn Phe Ile Ile Leu Glu Ile Ser Pro Ser Glu Lys Leu
        660                 665                 670 tta agt cca gaa tta att aat aca aat aat tgg acg agt acg gga tca    2122
Leu Ser Pro Glu Leu Ile Asn Thr Asn Asn Trp Thr Ser Thr Gly Ser
675                 680                 685 act aat att agc ggt aat aca ctc act ctt tat cag gga gga cga ggg    2170
Thr Asn Ile Ser Gly Asn Thr Leu Thr Leu Tyr Gln Gly Gly Arg Gly
690                 695                 700                 705 att cta aaa caa aac ctt caa tta gat agt ttt tca act tat aga gtg    2218
Ile Leu Lys Gln Asn Leu Gln Leu Asp Ser Phe Ser Thr Tyr Arg Val
                710                 715                 720 tat ttc tct gtg tcc gga gat gct aat gta agg att aga aat tct agg    2266
Tyr Phe Ser Val Ser Gly Asp Ala Asn Val Arg Ile Arg Asn Ser Arg
            725                 730                 735 gaa gtg tta ttt gaa aaa aag gat ata tgagcggcgc taaagatgtt          2313
Glu Val Leu Phe Glu Lys Lys Asp Ile
        740                 745 tctgaaatgt tcactacaaa attgaaagat aacttctata tagctttc t             2364

<210> SEQ ID NO 6
<211> LENGTH: 746
<212> TYPE: PRT
<213> ORGANISM: Bacillus thuringiensis

<400> SEQUENCE: 6

Met Asn Lys Asn Asn Ala Lys Le

-continued

```
Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Leu Thr Phe Ala Thr Glu Thr
            180                 185                 190

Ser Ser Lys Val Lys Lys Asp Gly Ser Pro Ala Asp Ile Arg Asp Glu
        195                 200                 205

Leu Ser Glu Leu Thr Glu Leu Ala Lys Ser Val Thr Gln Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Thr Lys Glu Asn Val Lys Thr Ser Gly Ser Glu Val Gly Asn Val Tyr
                260                 265                 270

Asn Phe Leu Ile Val Leu Thr Ala Leu Gln Ala Gln Ala Phe Leu Thr
                275                 280                 285

Leu Thr Pro Cys Arg Lys Leu Leu Gly Leu Ala Asp Ile Asp Tyr Thr
    290                 295                 300

Ser Ile Met Asn Glu His Leu Asn Lys Glu Lys Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
                340                 345                 350

Pro Gly His Ala Leu Ile Gly Phe Glu Ile Ser Asn Asp Ser Ile Thr
            355                 360                 365

Val Leu Lys Val Tyr Glu Ala Lys Leu Lys Gln Asn Tyr Gln Val Asp
                370                 375                 380

Lys Asp Ser Leu Ser Glu Val Ile Tyr Gly Asp Met Asp Lys Leu Leu
385                 390                 395                 400

Cys Pro Asp Gln Ser Gly Gln Ile Tyr Tyr Thr Asn Asn Ile Val Phe
                405                 410                 415

Pro Asn Glu Tyr Val Ile Thr Lys Ile Asp Phe Thr Lys Lys Met Lys
                420                 425                 430

Thr Leu Arg Tyr Glu Val Thr Ala Asn Phe Tyr Asp Ser Ser Thr Gly
                435                 440                 445

Glu Ile Asp Leu Asn Lys Lys Val Glu Ser Ser Glu Ala Glu Tyr
    450                 455                 460

Arg Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
                500                 505                 510

Glu Leu Leu Leu Ala Thr Asp Leu Ser Asn Lys Glu Thr Lys Leu Ile
                515                 520                 525

Val Pro Pro Ser Gly Phe Ile Ser Asn Ile Val Glu Asn Gly Ser Ile
                530                 535                 540

Glu Glu Asp Asn Leu Glu Pro Trp Lys Ala Asn Asn Lys Asn Ala Tyr
545                 550                 555                 560
```

```
Val Asp His Thr Gly Gly Val Asn Gly Thr Lys Ala Leu Tyr Val His
                565                 570                 575

Lys Asp Gly Gly Ile Ser Gln Phe Ile Gly Asp Lys Leu Lys Pro Lys
            580                 585                 590

Thr Glu Tyr Val Ile Gln Tyr Thr Val Lys Gly Lys Pro Ser Ile His
        595                 600                 605

Leu Lys Asp Glu Asn Thr Gly Tyr Ile His Tyr Glu Asp Thr Asn Asn
    610                 615                 620

Asn Leu Glu Asp Tyr Gln Thr Ile Asn Lys Arg Phe Thr Thr Gly Thr
625                 630                 635                 640

Asp Leu Lys Gly Val Tyr Leu Ile Leu Lys Ser Gln Asn Gly Asp Glu
                645                 650                 655

Ala Trp Gly Asp Asn Phe Ile Ile Leu Glu Ile Ser Pro Ser Glu Lys
            660                 665                 670

Leu Leu Ser Pro Glu Leu Ile Asn Thr Asn Asn Trp Thr Ser Thr Gly
        675                 680                 685

Ser Thr Asn Ile Ser Gly Asn Thr Leu Thr Leu Tyr Gln Gly Gly Arg
    690                 695                 700

Gly Ile Leu Lys Gln Asn Leu Gln Leu Asp Ser Phe Ser Thr Tyr Arg
705                 710                 715                 720

Val Tyr Phe Ser Val Ser Gly Asp Ala Asn Val Arg Ile Arg Asn Ser
                725                 730                 735

Arg Glu Val Leu Phe Glu Lys Lys Asp Ile
            740                 745
```

<210> SEQ ID NO 7
<211> LENGTH: 2403
<212> TYPE: DNA
<213> ORGANISM: Artificial Sequence
<220> FEATURE:
<223> OTHER INFORMATION: Description of Artificial Sequence: maize
      optimized sequence encoding VIP3A(a)
<221> NAME/KEY: misc_feature
<222> LOCATION: (11)..(2389)
<223> OTHER INFORMATION: maize optimized sequence encoding VIP3A(a)

<400> SEQUENCE: 7

```
ggatccacca atgaacatga acaagaacaa caccaagctg agcacccgcg ccctgccgag      60
cttcatcgac tacttcaacg gcatctacgg cttcgccacc ggcatcaagg acatcatgaa     120
catgatcttc aagaccgaca ccggcggcga cctgaccctg gacgagatcc tgaagaacca     180
gcagctgctg aacgacatca gcggcaagct ggacggcgtg aacggcagcc tgaacgacct     240
gatcgcccag gcaacctga acaccgagct gagcaaggag atccttaaga tcgccaacga     300
gcagaaccag gtgctgaacg acgtgaacaa caagctggac gccatcaaca ccatgctgcg     360
cgtgtacctg ccgaagatca ccagcatgct gagcgacgtg atgaagcaga actacgccct     420
gagcctgcag atcgagtacc tgagcaagca gctgcaggag atcagcgaca gctggacat      480
catcaacgtg aacgtcctga tcaacagcac cctgaccgag atcaccccgg cctaccagcg     540
catcaagtac gtgaacgaga gttcgaaga gctgaccttc gccaccgaga ccagcagcaa     600
ggtgaagaag gacggcagcc cggccgacat cctggacgag ctgaccgagc tgaccgagct     660
ggccaagagc gtgaccaaga cgacgtgga cggcttcgag ttctacctga cacccttcca     720
cgacgtgatg gtgggcaaca acctgttcgg ccgcagcgcc ctgaagaccg ccagcgagct     780
gatcaccaag gagaacgtga agaccagcgg cagcgaggtg ggcaacgtgt acaacttcct     840
gatcgtgctg accgccctgc aggcccaggc cttcctgacc ctgaccacct gtcgcaagct     900
```

-continued

```
gctgggcctg gccgacatcg actacaccag catcatgaac gagcacttga acaaggagaa    960
ggaggagttc cgcgtgaaca tcctgccgac cctgagcaac accttcagca acccgaacta   1020
cgccaaggtg aagggcagcg acgaggacgc caagatgatc gtggaggcta agccgggcca   1080
cgcgttgatc ggcttcgaga tcagcaacga cagcatcacc gtgctgaagg tgtacgaggc   1140
caagctgaag cagaactacc aggtggacaa ggacagcttg agcgaggtga tctacggcga   1200
catggacaag ctgctgtgtc cggaccagag cgagcaaatc tactacacca acaacatcgt   1260
gttcccgaac gagtacgtga tcaccaagat cgacttcacc aagaagatga agaccctgcg   1320
ctacgaggtg accgccaact tctacgacag cagcaccggc gagatcgacc tgaacaagaa   1380
gaaggtggag agcagcgagg ccgagtaccg caccctgagc gcgaacgacg acggcgtcta   1440
catgccactg ggcgtgatca gcgagacctt cctgaccccg atcaacggct ttggcctgca   1500
ggccgacgag aacagccgcc tgatcaccct gacctgtaag agctacctgc gcgagctgct   1560
gctagccacc gacctgagca acaaggagac caagctgatc gtgccaccga gcggcttcat   1620
cagcaacatc gtggagaacg cagcatcga ggaggacaac ctggagccgt ggaaggccaa   1680
caacaagaac gcctacgtgg accacaccgg cggcgtgaac ggcaccaagg ccctgtacgt   1740
gcacaaggac ggcggcatca gccagttcat cggcgacaag ctgaagccga agaccgagta   1800
cgtgatccag tacaccgtga agggcaagcc atcgattcac ctgaaggacg agaacaccgg   1860
ctacatccac tacgaggaca ccaacaacaa cctggaggac taccagacca tcaacaagcg   1920
cttcaccacc ggcaccgacc tgaagggcgt gtacctgatc ctgaagagcc agaacggcga   1980
cgaggcctgg ggcgacaact tcatcatcct ggagatcagc ccgagcgaga gctgctgag    2040
cccggagctg atcaacacca caactggac cagcaccggc agcaccaaca tcagcggcaa   2100
caccctgacc ctgtaccagg cggccgcgg catcctgaag cagaacctgc agctggacag   2160
cttcagcacc taccgcgtgt acttcagcgt gagcggcgac gccaacgtgc gcatccgcaa   2220
cagccgcgag gtgctgttcg agaagaggta catgagcggc gccaaggacg tgagcgagat   2280
gttcaccacc aagttcgaga aggacaactt ctacatcgag ctgagccagg gcaacaacct   2340
gtacggcggc ccgatcgtgc acttctacga cgtgagcatc aagttaacgt agagctcaga   2400
tct                                                                2403
```

<210> SEQ ID NO 8
<211> LENGTH: 1638
<212> TYPE: DNA
<213> ORGANISM: Agrotis ipsilon
<220> FEATURE:
<221> NAME/KEY: CDS
<222> LOCATION: (2)..(1189)
<223> OTHER INFORMATION: Translation of cDNA encoding VIP3A(a) receptor
      from Black cutworm

<400> SEQUENCE: 8

```
t agt gga tcc ccc ggg ctg cag gaa ttc gcg gcc gcg tcg acc atg tac    49
  Ser Gly Ser Pro Gly Leu Gln Glu Phe Ala Ala Ala Ser Thr Met Tyr
   1               5                  10                  15 tct aga ata ttt ttc ctc ctt gtg ata gtg tgt gct gtt aag gct tct     97
Ser Arg Ile Phe Phe Leu Leu Val Ile Val Cys Ala Val Lys Ala Ser
             20                  25                  30 ctg ttt act gta aat gtg tat gat gat aac ccc gaa act gaa att gcg    145
Leu Phe Thr Val Asn Val Tyr Asp Asp Asn Pro Glu Thr Glu Ile Ala
         35                  40                  45 agt agt cta aaa ggc tgt aac ccc caa gag tgt gac cag cgg tgt cgt    193
```

```
Ser Ser Leu Lys Gly Cys Asn Pro Gln Glu Cys Asp Gln Arg Cys Arg
    50                  55                  60 aga ctg aag ttt ccc ggt ggc gcc tgt gtc aat ggt cgc tgc aag tgt        241
Arg Leu Lys Phe Pro Gly Gly Ala Cys Val Asn Gly Arg Cys Lys Cys
 65                  70                  75                  80 gac aac ttc ctc agt gta aaa gat gac gtg tct gtt gaa gag cct gcg        289
Asp Asn Phe Leu Ser Val Lys Asp Asp Val Ser Val Glu Glu Pro Ala
                 85                  90                  95 att ctc aaa gat ttg gtg tca tta gaa gct gaa cag gca gcg aaa agt        337
Ile Leu Lys Asp Leu Val Ser Leu Glu Ala Glu Gln Ala Ala Lys Ser
                100                 105                 110 aga tgc aga aac aga gtg tgt gac gcg gtg tgc cgt gcc cta cac aac        385
Arg Cys Arg Asn Arg Val Cys Asp Ala Val Cys Arg Ala Leu His Asn
            115                 120                 125 acc agt ggt gcc tgt gtt gat gga caa tgc aag tgt act aat aag atc        433
Thr Ser Gly Ala Cys Val Asp Gly Gln Cys Lys Cys Thr Asn Lys Ile
        130                 135                 140 agt gca gga gat att gtg tct gat cct gct gaa tcg cta cgc act tgt        481
Ser Ala Gly Asp Ile Val Ser Asp Pro Ala Glu Ser Leu Arg Thr Cys
145                 150                 155                 160 aac cct ata agg tgt gac gaa caa tgt aga aga aat ggc cat gaa ttt        529
Asn Pro Ile Arg Cys Asp Glu Gln Cys Arg Arg Asn Gly His Glu Phe
                165                 170                 175 ggt gtt tgc ttc aaa gga caa tgc aag tgt gat tac ttc ctc aag gaa        577
Gly Val Cys Phe Lys Gly Gln Cys Lys Cys Asp Tyr Phe Leu Lys Glu
                180                 185                 190 gaa gtc gat gaa cct gaa gtt aca agc ctt cca aaa aac tgc aac ccc        625
Glu Val Asp Glu Pro Glu Val Thr Ser Leu Pro Lys Asn Cys Asn Pro
            195                 200                 205 caa gag tgt gac cag cgt tgt cgt aga ctg aag ttc ccc ggt ggc gcc        673
Gln Glu Cys Asp Gln Arg Cys Arg Arg Leu Lys Phe Pro Gly Gly Ala
        210                 215                 220 tgt gtc aac ggg cgc tgc aag tgt gac aac ttc ttc agt gca gga gat        721
Cys Val Asn Gly Arg Cys Lys Cys Asp Asn Phe Phe Ser Ala Gly Asp
225                 230                 235                 240 att gtg tct gat cct gcc gaa tcg cta cgc tct tgt aac cct ata agg        769
Ile Val Ser Asp Pro Ala Glu Ser Leu Arg Ser Cys Asn Pro Ile Arg
                245                 250                 255 tgt gac gaa caa tgt aga aga aat ggc cat gaa ttt ggt gtt tgc ttc        817
Cys Asp Glu Gln Cys Arg Arg Asn Gly His Glu Phe Gly Val Cys Phe
                260                 265                 270 aaa gga caa tgc aag tgt gat tac ttc ctc aac tca gaa gta gac gct        865
Lys Gly Gln Cys Lys Cys Asp Tyr Phe Leu Asn Ser Glu Val Asp Ala
            275                 280                 285 gtt aat gag ttt cct caa gcg ggc tca aaa cgc tac tgc aac tta acg        913
Val Asn Glu Phe Pro Gln Ala Gly Ser Lys Arg Tyr Cys Asn Leu Thr
        290                 295                 300 caa tgc aac cag acg tgc gcc aat cgt ttc tat gat agt gct aga gtg        961
Gln Cys Asn Gln Thr Cys Ala Asn Arg Phe Tyr Asp Ser Ala Arg Val
305                 310                 315                 320 atc cac ggc tgg tgc aaa tgc tac agt aag atg gaa aga cag gat gca       1009
Ile His Gly Trp Cys Lys Cys Tyr Ser Lys Met Glu Arg Gln Asp Ala
                325                 330                 335 tct cca tta aac gat gtg act gag gat gaa aat gaa gtt tct aac gat       1057
Ser Pro Leu Asn Asp Val Thr Glu Asp Glu Asn Glu Val Ser Asn Asp
                340                 345                 350 atc ctg agg act gtt gca gag gag ctg tct gat gtg tca cct agg gcc       1105
Ile Leu Arg Thr Val Ala Glu Glu Leu Ser Asp Val Ser Pro Arg Ala
            355                 360                 365
```

-continued

```
tgc aaa tca gcg agc tgc aat caa gca tgt cgc gcc ttc tac ttt aaa     1153
Cys Lys Ser Ala Ser Cys Asn Gln Ala Cys Arg Ala Phe Tyr Phe Lys
370                 375                 380 gga ggg tgg tgt cgc ttt gga cga tgc caa tgc ttc taaaattagt          1199
Gly Gly Trp Cys Arg Phe Gly Arg Cys Gln Cys Phe
385                 390                 395 atgatatatg aattttgtat tattcggtta attgtgttat gtttaaaaaa cataatgtct   1259
tcattttaga aaaaagtacc ttcactaaag cgcaacaatt aactagtagt taattattaa   1319
ctagtagtta aattattgat gattatgatt atcttagtag tagttaatta taatcatcaa   1379
ctattaacta gtagttaatt attaactagt agttaaatta ttgatgatta tgattatctt   1439
agtagtagtt aattattgtt tcttataata atctagtatg ttggtaggta cttaataata   1499
acgcttctga caaaaaattt aaaattaaat aattctatca aacataaata ataactgaaa   1559
taaaaattta aagagaaaaa aaaaaagtc gacgcggccg cgaattcgat atcaagctta    1619
tcgataccgt cgacctcga                                                1638
```

<210> SEQ ID NO 9
<211> LENGTH: 396
<212> TYPE: PRT
<213> ORGANISM: Agrotis ipsilon

<400> SEQUENCE: 9

```
Ser Gly Ser Pro Gly Leu Gln Glu Phe Ala Ala Ser Thr Met Tyr
 1               5                  10                  15

Ser Arg Ile Phe Phe Leu Leu Val Ile Val Cys Ala Val Lys Ala Ser
                20                  25                  30

Leu Phe Thr Val Asn Val Tyr Asp Asp Asn Pro Glu Thr Glu Ile Ala
            35                  40                  45

Ser Ser Leu Lys Gly Cys Asn Pro Gln Glu Cys Asp Gln Arg Cys Arg
        50                  55                  60

Arg Leu Lys Phe Pro Gly Gly Ala Cys Val Asn Gly Arg Cys Lys Cys
 65                  70                  75                  80

Asp Asn Phe Leu Ser Val Lys Asp Val Ser Val Glu Glu Pro Ala
                85                  90                  95

Ile Leu Lys Asp Leu Val Ser Leu Glu Ala Glu Gln Ala Ala Lys Ser
            100                 105                 110

Arg Cys Arg Asn Arg Val Cys Asp Ala Val Cys Arg Ala Leu His Asn
        115                 120                 125

Thr Ser Gly Ala Cys Val Asp Gly Gln Cys Lys Cys Thr Asn Lys Ile
    130                 135                 140

Ser Ala Gly Asp Ile Val Ser Asp Pro Ala Glu Ser Leu Arg Thr Cys
145                 150                 155                 160

Asn Pro Ile Arg Cys Asp Glu Gln Cys Arg Arg Asn Gly His Glu Phe
                165                 170                 175

Gly Val Cys Phe Lys Gly Gln Cys Lys Cys Asp Tyr Phe Leu Lys Glu
            180                 185                 190

Glu Val Asp Glu Pro Glu Val Thr Ser Leu Pro Lys Asn Cys Asn Pro
        195                 200                 205

Gln Glu Cys Asp Gln Arg Cys Arg Arg Leu Lys Phe Pro Gly Gly Ala
    210                 215                 220

Cys Val Asn Gly Arg Cys Lys Cys Asp Asn Phe Phe Ser Ala Gly Asp
225                 230                 235                 240

Ile Val Ser Asp Pro Ala Glu Ser Leu Arg Ser Cys Asn Pro Ile Arg
                245                 250                 255
```

-continued

```
Cys Asp Glu Gln Cys Arg Arg Asn Gly His Glu Phe Gly Val Cys Phe
            260                 265                 270

Lys Gly Gln Cys Lys Cys Asp Tyr Phe Leu Asn Ser Glu Val Asp Ala
        275                 280                 285

Val Asn Glu Phe Pro Gln Ala Gly Ser Lys Arg Tyr Cys Asn Leu Thr
    290                 295                 300

Gln Cys Asn Gln Thr Cys Ala Asn Arg Phe Tyr Asp Ser Ala Arg Val
305                 310                 315                 320

Ile His Gly Trp Cys Lys Cys Tyr Ser Lys Met Glu Arg Gln Asp Ala
                325                 330                 335

Ser Pro Leu Asn Asp Val Thr Glu Asp Glu Asn Glu Val Ser Asn Asp
            340                 345                 350

Ile Leu Arg Thr Val Ala Glu Glu Leu Ser Asp Val Ser Pro Arg Ala
        355                 360                 365

Cys Lys Ser Ala Ser Cys Asn Gln Ala Cys Arg Ala Phe Tyr Phe Lys
    370                 375                 380

Gly Gly Trp Cys Arg Phe Gly Arg Cys Gln Cys Phe
385                 390                 395

<210> SEQ ID NO 10
<211> LENGTH: 14
<212> TYPE: PRT
<213> ORGANISM: Bacillus thuringiensis
<220> FEATURE:
<223> OTHER INFORMATION: N-terminal amino acid sequence of protein known
      as anion exchange fraction 23 (smaller)

<400> SEQUENCE: 10

Xaa Glu Pro Phe Val Ser Ala Xaa Xaa Xaa Gln Xaa Xaa Xaa
  1               5                  10

<210> SEQ ID NO 11
<211> LENGTH: 13
<212> TYPE: PRT
<213> ORGANISM: Bacillus thuringiensis
<220> FEATURE: <221>  SITE<222>  (1)..(13)<223>  Xaa represents any
      amino acid

<400> SEQUENCE: 11

Xaa Glu Tyr Glu Asn Val Glu Pro Phe Val Ser Ala Xaa
  1               5                  10

<210> SEQ ID NO 12
<211> LENGTH: 14
<212> TYPE: PRT
<213> ORGANISM: Bacillus thuringiensis

<400> SEQUENCE: 12

Met Asn Lys Asn Asn Thr Lys Leu Pro Thr Arg Ala Leu Pro
  1               5                  10

<210> SEQ ID NO 13
<211> LENGTH: 15
<212> TYPE: PRT
<213> ORGANISM: Bacillus thuringiensis

<400> SEQUENCE: 13

Ala Leu Ser Glu Asn Thr Gly Lys Asp Gly Gly Tyr Ile Val Pro
  1               5                  10                  15

<210> SEQ ID NO 14
```

-continued

<211> LENGTH: 9
<212> TYPE: PRT
<213> ORGANISM: Bacillus thuringiensis

<400> SEQUENCE: 14

Met Asp Asn Asn Pro Asn Ile Asn Glu
1 5

<210> SEQ ID NO 15
<211> LENGTH: 9
<212> TYPE: PRT
<213> ORGANISM: Bacillus thuringiensis

<400> SEQUENCE: 15

Met Asp Asn Asn Pro Asn Ile Asn Glu
1 5

<210> SEQ ID NO 16
<211> LENGTH: 11
<212> TYPE: PRT
<213> ORGANISM: Bacillus thuringiensis

<400> SEQUENCE: 16

Met Asn Val Leu Asn Ser Gly Arg Thr Thr Ile
1 5 10

<210> SEQ ID NO 17
<211> LENGTH: 17
<212> TYPE: DNA
<213> ORGANISM: Artificial Sequence
<220> FEATURE:
<223> OTHER INFORMATION: Description of Artificial Sequence: primer sequence

<400> SEQUENCE: 17
cgattaatgt tggcctc 17

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: primer sequence

<400> SEQUENCE: 18
cattagcatc tccggacaca g 21

<210> SEQ ID NO 19
<211> LENGTH: 2370
<212> TYPE: DNA
<213> ORGANISM: Artificial Sequence
<220> FEATURE:
<223> OTHER INFORMATION: Description of Artificial Sequence: Synthetic DNA encoding VIP3A(b)

<400> SEQUENCE: 19
atgaacaaga acaacaccaa gctgagcacc cgcgccctgc cgagcttcat cgactacttc 60
aacggcatct acggcttcgc caccggcatc aaggacatca tgaacatgat cttcaagacc 120
gacaccggcg gcgacctgac cctggacgag atcctgaaga accagcagct gctgaacgac 180
atcagcggca agctggacgg cgtgaacggc agcctgaacg acctgatcgc ccagggcaac 240
ctgaacaccg agctgagcaa ggagatcctt aagatcgcca acgagcagaa ccaggtgctg 300
aacgacgtga acaacaagct ggacgccatc aacaccatgc tgcgcgtgta cctgccgaag 360

```
atcaccagca tgctgagcga cgtgatgaag cagaactacg ccctgagcct gcagatcgag    420
tacctgagca agcagctgca ggagatcagc gacaagctgg acatcatcaa cgtgaacgtc    480
ctgatcaaca gcaccctgac cgagatcacc ccggcctacc agcgcatcaa gtacgtgaac    540
gagaagttcg aagagctgac cttcgccacc gagaccagca gcaaggtgaa gaaggacggc    600
agcccggccg acatcctgga cgagctgacc gagctgaccg agctggcgaa gagcgtgacc    660
aagaacgacg tggacggctt cgagttctac ctgaacaccc tccacgacgt gatggtgggc    720
aacaacctgt tcggccgcag cgccctgaag accgccagcg agctgatcac caaggagaac    780
gtgaagacca gcggcagcga ggtgggcaac gtgtacaact tcctgatcgt gctgaccgcc    840
ctgcaggcca aggccttcct gaccctgacc ccctgtcgca agctgctggg cctggccgac    900
atcgactaca ccagcatcat gaacgagcac ttgaacaagg agaaggagga gttccgcgtg    960
aacatcctgc cgaccctgag caacaccttc agcaacccga actacgccaa ggtgaagggc   1020
agcgacgagg acgccaagat gatcgtggag gctaagccgg ccacgcgtt gatcggcttc   1080 gagatcagca cgacagcat caccgtgctg aaggtgtacg aggccaagct gaagcagaac   1140
taccaggtgg acaaggacag cttgagcgag gtgatctacg gcgacatgga caagctgctg   1200
tgtccggacc agagcgggca aatctactac accaacaaca tcgtgttccc gaacgagtac   1260
gtgatcacca agatcgactt caccaagaag atgaagaccc tgcgctacga ggtgaccgcc   1320
aacttctacg acagcagcac cggcgagatc gacctgaaca agaagaaggt ggagagcagc   1380
gaggccgagt accgcaccct gagcgcgaac gacgacggcg tctacatgcc actgggcgtg   1440
atcagcgaga ccttcctgac cccgatcaac ggctttggcc tgcaggccga cgagaacagc   1500
cgcctgatca ccctgacctg taagagctac ctgcgcgagc tgctgctagc caccgacctg   1560
agcaacaagg agaccaagct gatcgtgcca ccgagcggct tcatcagcaa catcgtggag   1620
aacggcagca tcgaggagga caacctggag ccgtggaagg ccaacaacaa gaacgcctac   1680
gtggaccaca ccggcggcgt gaacggcacc aaggccctgt acgtgcacaa ggacggcggc   1740
atcagccagt tcatcggcga caagctgaag ccgaagaccg agtacgtgat ccagtacacc   1800
gtgaagggca gccatcgat tcacctgaag gacgagaaca ccggctacat ccactacgag   1860
gacaccaaca caaacctgga ggactaccag accatcaaca agcgcttcac caccggcacc   1920
gacctgaagg gcgtgtacct gatcctgaag agccagaacg gcgacgaggc ctggggcgac   1980
aacttcatca tcctggagat cagcccgagc gagaagctgc tgagcccgga gctgatcaac   2040
accaacaact ggaccagcac cggcagcacc aacatcagcg gcaacaccct gaccctgtac   2100
cagggcggcc gcggcatcct gaagcagaac ctgcagctgg acagcttcag cacctaccgc   2160
gtgtacttca gcgtgagcgg cgacgccaac gtgcgcatcc gcaactcccg cgaggtgctg   2220
ttcaagaaga ggtacatgag cggcgccaag gacgtgagcg agatgttcac caccaagttc   2280
gagaaggaca acttctacat cgagctgagc cagggcaaca acctgtacgg cggcccgatc   2340
gtgcacttct acgacgtgag catcaagtag                                    2370
```

<210> SEQ ID NO 20
<211> LENGTH: 2241
<212> TYPE: DNA
<213> ORGANISM: Artificial Sequence
<220> FEATURE:
<223> OTHER INFORMATION: Description of Artificial Sequence: Synthetic
      DNA encoding VIP3A(c)

<400> SEQUENCE: 20

-continued

```
atgaacaaga caacgccaa gctgagcacc cgcgccctgc cgagcttcat cgactacttc      60
aacggcatct acggcttcgc caccggcatc aaggacatca tgaacatgat cttcaagacc    120
gacaccggcg cgacctggc cctggacgag atcctggaga ccagcagct gctgaacgac      180
atcagcggca agctggacgg cgtgaacggc agcctgaacg acctgatcgc ccagggcaac    240
ctgaacaccg agctgagcaa ggagatcctt aagatcgcca cgagcagaa ccaggtgctg     300
aacgacgtga caacaagct ggacgccatc aacaccatgc tgcgcgtgta cctgccgaag    360
atcaccagca tgctgagcga cgtgatgaag cagaactacg ccctgagcct gcagatcgag    420
tacctgagca gcagctgca ggagatcagc gacaagctgg acatcatcaa cgtgaacgtc    480
ctgatcaaca gcaccctgac cgagatcacc ccggcctacc agcgcatcaa gtacgtgaac    540
gagaagttcg aagagctgac cttcgccacc gagaccagca gcaaggtgaa gaaggacggc    600
agcccggccg acatccggga cgagctgagc gagctgaccg agctggcgaa gagcgtgacc    660
cagaacgacg tggacggctt cgagttctac ctgaacacct ccacgacgt gatggtgggc    720
aacaacctgt tcggccgcag cgccctgaag accgccagcg agctgatcac caaggagaac    780
gtgaagacca gcggcagcga ggtgggcaac gtgtacaact tcctgatcgt gctgaccgcc    840
ctgcaggccc aggccttcct gaccctgacc ccctgtcgca gctgctgggg cctggccgac    900
atcgactaca ccagcatcat gaacgagcac ttgaacaagg agaaggagga gttccgcgtg    960
aacatcctgc cgaccctgag caacaccttc agcaacccga actacgccaa ggtgaagggc   1020
gagatcagca cgacagcat caccgtgctg aaggtgtacg aggccaagct gaagcagaac   1140
taccaggtgg acaaggacag cttgagcgag gtgatctacg cgacatgga caagctgctg   1200
tgtccggacc agagcgggca aatctactac accaacaaca tcgtgttccc gaacgagtac   1260
gtgatcacca agatcgactt caccaagaag atgaagaccc tgcgctacga ggtgaccgcc   1320
aacttctacg acagcagcac cggcgagatc gacctgaaca agaagaaggt ggagagcagc   1380
gaggccgagt accgcaccct gagcgcgaac gacgacggcg tctacatgcc actgggcgtg   1440
atcagcgaga ccttcctgac cccgatcaac ggctttggcc tgcaggccga cgagaacagc   1500
cgcctgatca ccctgacctg taagagctac ctgcgcgagc tgctgctagc caccgacctg   1560
agcaacaagg agaccaagct gatcgtgcca ccgagcggct tcatcagcaa catcgtggag   1620
aacggcagca tcgaggagga caacctggag ccgtggaagg ccaacaacaa gaacgcctac   1680
gtggaccaca ccggcggcgt gaacggcacc aaggccctgt acgtgcacaa ggacggcggc   1740
atcagccagt tcatcggcga caagctgaag ccgaagaccg agtacgtgat ccagtacacc   1800
gtgaagggca agccatcgat tcacctgaag gacgagaaca ccggctacat ccactacgag   1860
gacaccaaca caacctgga ggactaccag accatcaaca gcgcttcac caccggcacc   1920
gacctgaagg gcgtgtacct gatcctgaag gccagaacg cgacgaggc ctggggcgac   1980
aacttcatca tcctggagat cagcccgagc gagaagctgc tgagcccgga gctgatcaac    2040
accaacaact ggaccagcac cggcagcacc aacatcagcg gcaacaccct gaccctgtac    2100
cagggcggcc gcggcatcct gaagcagaac ctgcagctgg acagcttcag cacctaccgc    2220
ttcgagaaga aggacaagta g                                              2241
```

<210> SEQ ID NO 21
<211> LENGTH: 13
<212> TYPE: DNA
<213> ORGANISM: Artificial Sequence
<220> FEATURE:

-continued

```
<223> OTHER INFORMATION: Description of Artificial Sequence: Clontech
      sequence

<400> SEQUENCE: 21
gtcgaccatg gtc                                                        13

<210> SEQ ID NO 22
<211> LENGTH: 12
<212> TYPE: DNA
<213> ORGANISM: Artificial Sequence
<220> FEATURE:
<223> OTHER INFORMATION: Description of Artificial Sequence: Joshi
      sequence

<400> SEQUENCE: 22
taaacaatgg ct                                                         12
```